(12) United States Patent
Kung Sutherland et al.

(10) Patent No.: US 8,227,441 B2
(45) Date of Patent: Jul. 24, 2012

(54) METHODS TO INCREASE OR DECREASE BONE DENSITY

(75) Inventors: Mary S. Kung Sutherland, Bothell, WA (US); James Charles Geoghegan, Seattle, WA (US); John Latham, Seattle, WA (US); Changpu Yu, Mill Creek, WA (US)

(73) Assignee: Celltech R & D, Inc., Thousand Oaks, CA (US)

( * ) Notice: Subject to any disclaimer, the term of this patent is extended or adjusted under 35 U.S.C. 154(b) by 0 days.

(21) Appl. No.: 12/698,462

(22) Filed: Feb. 2, 2010

(65) Prior Publication Data
US 2011/0009467 A1   Jan. 13, 2011

Related U.S. Application Data

(60) Continuation of application No. 11/960,509, filed on Dec. 19, 2007, now Pat. No. 7,655,420, which is a division of application No. 10/377,315, filed on Feb. 28, 2003, now Pat. No. 7,332,276.

(60) Provisional application No. 60/361,258, filed on Mar. 1, 2002, provisional application No. 60/406,171, filed on Aug. 27, 2002, provisional application No. 60/447,393, filed on Feb. 13, 2003.

(51) Int. Cl.
*C12N 15/11* (2006.01)
*C07H 21/02* (2006.01)

(52) U.S. Cl. ..................... 514/44 A; 536/24.5

(58) Field of Classification Search .......... None
See application file for complete search history.

(56) References Cited

U.S. PATENT DOCUMENTS

| | | |
|---|---|---|
| 3,561,444 A | 2/1971 | Boucher |
| 3,703,173 A | 11/1972 | Dixon |
| 4,036,945 A | 7/1977 | Haber |
| 4,051,842 A | 10/1977 | Hazel et al. |
| 4,140,122 A | 2/1979 | Kuhl et al. |
| 4,331,647 A | 5/1982 | Goldenberg |
| 4,383,529 A | 5/1983 | Webster |
| 4,624,251 A | 11/1986 | Miller |
| 4,635,627 A | 1/1987 | Gam |
| 4,816,567 A | 3/1989 | Cabilly et al. |
| 4,946,778 A | 8/1990 | Ladner et al. |
| 4,960,432 A | 10/1990 | Junino et al. |
| 4,962,091 A | 10/1990 | Eppstein et al. |
| 5,073,174 A | 12/1991 | Vayssie et al. |
| 5,382,587 A | 1/1995 | Baldwin et al. |
| 5,622,856 A | 4/1997 | Natsoulis |
| 5,658,776 A | 8/1997 | Flotte et al. |
| 5,658,785 A | 8/1997 | Johnson |
| 5,837,484 A | 11/1998 | Trempe et al. |
| 5,980,584 A | 11/1999 | Lim et al. |
| 6,258,595 B1 | 7/2001 | Gao et al. |
| 6,342,079 B1 | 1/2002 | Pan et al. |
| 6,365,403 B1 | 4/2002 | Natsoulis et al. |
| 6,395,511 B1 | 5/2002 | Brunkow et al. |
| 6,475,769 B1 | 11/2002 | Wilson et al. |
| 6,489,445 B1 * | 12/2002 | Brunkow et al. ............ 530/350 |
| 6,541,258 B2 | 4/2003 | Allen et al. |
| 7,056,704 B2 * | 6/2006 | Tuschl et al. ................. 435/91.1 |
| 2003/0186915 A1 | 10/2003 | Pan et al. |

FOREIGN PATENT DOCUMENTS

| | | |
|---|---|---|
| DE | 3441148 | 5/1986 |
| DE | 20013155 | 10/2000 |
| EP | 0182187 | 5/1986 |
| EP | 404097 | 12/1990 |
| WO | WO-93/11161 | 6/1993 |
| WO | WO-94/07529 | 4/1994 |
| WO | WO-99/41399 | 8/1999 |

OTHER PUBLICATIONS

Abe et al., "Essential Requirement of BMPs-2/4 for Both Osteoblast and Osteoclast Formation in Murine Bone Marrow Cultures from Adult Mice: Antagonism by Noggin," *J. Bone. Min. Res.*, 15(4): 663-673 (2000).
Aitken et al., "A phase I study of aerosolized administration of tgAAVCF to cystic fibrosis subjects with mild lung disease," *Hum. Gene Ther.* 12: 1907-1916 (2001).
Arenz et al., "Synthesis of the First Selective Irreversible Inhibitor of Neutral Sphingomyelinase," *Angewandte Chemie Intl. Ed.*, 39(8): 1440-2 (2000).
Balemans et al., Extracellular regulation of BMP signaling in vertebrates: A cocktail of modulators. *Dev. Biol.* 250: 231-50 (2002).
Baines et al., "Purification of Immunoglobulin G (IgG)," *Methods in Molecular Biology*, 10: 79-104 (1992).
Beighton et al., The clinical features of sclerosteosis, A review of the manifestations in twenty-five affected individuals. *Ann. Int. Med.* 84: 393-7 (1976).
Beresford et al., "Marrow Stromal Cell Culture," *Handbooks in Practical Animal Cell Biology*, (1997).
Bird et al., "Single-chain antigen-binding proteins," *Science*, 242(4877): 423-6 (1988).
Boden et al., Glucocorticoid-induced differentiation of fetal rat calvarial osteoblasts is mediated by bone morphogenetic protein-6. *Endocrinol.* 138: 2820-8 (1997).
Bostrom et al., Immunolocalization and expression of bone morphogenetic proteins 2 and 4 in fracture healing. *J. Orthopaedic Res.* 13: 357-67 (1995).
Brunkow et al., Bone dysplasia scleroteosis results from loss of the SOST gene product, a novel cystine knot-containing protein. *Am. J. Hum. Genet.* 68: 577-89 (2001).
Budd et al., "Death receptors couple to both cell proliferation and apoptosis," *J. Clin. Invest,.* 109: 437-442 (2002).
Carter et al., "Adeno-associated Virus and AAV vectors for Gene Therapy," *Gene and Cell Therapy: Therapeutic Mechanisms and Strategies*, 2nd Edition,. 71-101 (2004).
Clackson et al., "Making antibody fragments using phage display libraries," *Nature*, 352: 624-8 (1991).
Clark et al., "Cell lines for the production of recombinant adeno-associated virus," *Hum. Gene Ther.*, 9: 1329-1341 (1995).

(Continued)

*Primary Examiner* — Richard Schnizer

(74) *Attorney, Agent, or Firm* — Marshall, Gerstein & Borun LLP

(57) ABSTRACT

The SOST gene gives rise to sclerostin, a protein that leads to apoptosis of bone progenitor cells. The invention provides antagonists to the sclerostin protein, and methods for identifying new sclerostin antagonists. The invention also provides molecules that can depress expression of the SOST gene, as well as methods for identifying such molecules. Such molecules and antagonists are useful for increasing bone mineralization in mammals, for example, in the treatment of osteoporosis.

8 Claims, 28 Drawing Sheets

OTHER PUBLICATIONS

Clark et al., "A stable cell line carrying adenovirus-inducible rep and cap genes allows for infectivity titration of adeno-associated virus vectors", *Gene Therapy*, 3:1124-1132 (1996).

Clark et al., "Highly Purified Recombinant Adeno-Associated Virus Vectors Are Biologically Active and Free of Detectable Helper and Wild-Type Viruses", Hum Gene Therapy, 10(6):1031-1039 (1999).

Clark et al., "Recombinant Adeno-Associated Viral Vectors Mediate Long-Term Transgene Expression in Muscle", *Hum Gene Therapy*, 8(6):659-669 (1997).

Clothia et al., "Domain Association in Immunoglobulin Molecules," *J. Mol. Biol.*, 186: 651-663 (1985).

Coligan et al., Current Protocols in Immunology, Wiley Interscience, Unit 9 (1991).

Coligan et al., Production of Polyclonal Antisera in Rabbits, Rats, Mice and Hamsters. Current Protocols in Immunology. Section 2.5. 1-2.6.7 (1992).

Coligan et al., Production of Polyclonal Antisera in Rabbits, Rats, Mice and Hamsters. Current Protocols in Immunology. Section 2.7. 1-2.7.12 (1992).

Coligan et al., Production of Polyclonal Antisera in Rabbits, Rats, Mice and Hamsters. Current Protocols in Immunology. Section 2.9. 1-2.9.3 (1992).

Coligan et al., Production of Polyclonal Antisera in Rabbits, Rats, Mice and Hamsters. Current Protocols in Immunology. Section 2.4.1 (1992).

Epstein et al., "Endocrine function in sclerosteosis," *S. Afr. Med. J.*, 55: 1105-10 (1979).

Fan and Dong, "Replication of rep-cap Genes Is Essential for the High-Efficiency Production of Recombinant AAV", *Human Gene Therapy*, 8:87-98 (1997).

Fang et al., "Stimulation of new bone formation by direct transfer of osteogenic plasmid genes," *Proc. Natl. Acad. Sci. USA*, 93: 5753-5758 (1996).

Gao et al., Molecular Therapy, "Rep/Cap Gene Amplification and High-Yield Production of AAV in an A549 Cell Line Expressing Rep/Cap", 5(5):644-649 (2002).

Gazit et al., "Modulation of Expression and Cell Surface Binding of Members of the Transforming Growth Factor-β Superfamily druing Retinoic Acid-Induced Osteoblastic Differentiation of Multipotential Mesenchymal Cells," *Mol. Endocrinol*, 7(2): 189-198 (1999).

Gitelman et al., Vgr-1/BMP-6 induces osteoblastic differentiation of pluripotential mesenchymal cells. Cell Growth & Differentiation. 6: 827-36 (1995).

Graham and Prevec, "Methods for Construction of Adenovirus Vectors", *Mol. Biotechnol.*, 3:207-220 (1995).

Handbook of Parvoviruses, vol. I (P. Tjissen, ed.) CRC Press, Boca Raton, pp. 255-282 (1989).

Harlow et al., Antibodies: A Laboratory Manual. Cold Spring Harbor Publishers, Cold Spring Harbor, New York: (1988).

Hill et al., Multiple extracellular signals promote osteoblast survival and apoptosis. Endocrinology. 138: 3849-58 (1997).

Hock et al., Perspective, osteoblast apoptosis and bone turnover. J. Bone Miner. Res. 16: 975-84 (2001).

Hofmann et al., "Various glucocorticoids differ in their ability to induce gene expression, apoptosis and to repress NF-κB-dependent transcription," *FEBS Letters*, 441: 441-446 (1998).

Hollinger et al., "Diabodies: Small bivalent and bispecific antibody fragments," *Proc. Natl. Acad. Sci. USA*, 90: 6444-6448 (1993).

Holmes et al., "Structural Consequences of Humanizing an Antibody," *J. Immunol.*, 158: 2192-2201 (1997).

Jilka et al., Increased bone formation by prevention of osteoblast apoptosis with parathyroid hormone. J. Clin. Invest. 104: 439-46 (1999).

Jones et al., "Replacing the complementarity-determining regions in a human antibody with those from a mouse," *Nature*, 321: 522-5 (1986).

Katagiri et al., The non-osteogenic mouse pluripotent cell line, C3H10T1/2, is induced to differentiate into osteoblastic cells by recombinant human bone morphogenetic protein-2. Biochem. Biophys. Res. Comm. 172: 295-9 (1990).

Kelecsenyi-Dumesnil, Bulletin de la Societe Chimique de France, 815-6 (1955).

Kohler et al., "Continuous cultures of fused cells secreting antibody of predefined specificity," *Nature*, 256: 495-497 (1975).

Larrick et al., "PCR Amplification of Antibody Genes," *Methods*, 2(2):106-110 (1991).

Leonard and Berns, "Cloning, Expression, and Partial Purification of Rep78: An Adeno-Associated Virus Replication Protein", *Virology*,200:566-573 (1994).

Li et al., "Role for Highly Regulated rep Gene Expression in Adeno-Associated Virus Vector Production", *J. Virol.*, 71(7):5236-5243 (1997).

Lian et al., Bone formation: Osteoblast lineage cells, growth factors, matrix proteins, and mineralization process. Primer on the Metabolic Bone Diseases and Disorders of Mineral Metabolism. 4th Edition: 14-29 (1999).

Liu et al., "Selective Rep-Cap Gene Amplification as a Mechanism for High-Titer Recombinant AAV Production From Stable Cell Lines", *Molecular Therapy*, 2(4):394-403 (2000).

Lu et al., "Orphan Nuclear Receptors as eLiXiRs and FiXeRs of Sterol Metabolism," *J. Biol. Chem*, 276(41):37735-37738 (2001).

Manolagas, "Birth and Death of Bone Cells: Basic Regulatory Mechanisms and Implications for the Pathogenesis and Treatment of Osteoporosis," *Endocrine Rev*, 21(2):115-137 (2000).

Marks et al., "By-passing Immunization," *J. Mol. Biol.*, 222: 581-597 (1991).

Martinez et al., "Synthetic small inhibiting RNAs: Efficient tools to inactivate oncogenic mutations and restore p53 pathways," *PNAS*, 99(23):14849-14854 (2002).

Matsushita et al., "Adeno-associated virus vectors can be efficiently produced without helper virus", *Gene Therapy*, 5:938-945 (1998).

Miura et al., "Functional Modulation of the Glucocorticoid Receptor and Suppression of NF-κB-dependent Transcription by Ursodeoxycholic Acid," *J. Biol. Chem*, 276(50): 47371-47378 (2001).

Morrison et al., "Chimeric human antibody molecules: Mouse antigen-binding domains with human constant region domains," *Proc. Natl. Acad. Sci. USA*, 81: 6851-6855 (1984).

Muzyczka, "Use of Adeno-Associated Virus as a General Transduction Vector for Mammalian Cells", *Current Topics in Microbiology and Immunology*, 158:97-129 (1992).

Nakase et al., Transient and localized expression of bone morphogenetic protein 4 messenger RNA during fracture healing. 9(5): 651-9 (1994).

Newman, "Therapeutic aerosols," *Aeosols and the Lung: Clinical and Experimental Aspects*, 197-224 (1984).

Nifuji et al., Coordinated expression of noggin and bone morphogenetic proteins (BMPs) during early skeletogenesis and induction of noggin expression by BMP-7. J. Bone Miner. Res. 14: 2057-66 (1999).

Nony et al., "Novel *cis*-Acting Replication Element in the Adeno-Associated Virus Type 2 Genome is Involved in Amplification of Integrated rep-cap Sequences", *J. Virol.*, 75(20):9991-9994 (2001).

Novotny et al., "Structural invariants of antigen binding: Comparison of immunoglobulin $V_L$-$V_H$ and $V_L$-$V_L$ domain dimers," *Proc. Natl. Acad. Sci. USA*, 82: 4592-4596 (1985).

Oreffo et al., Human bone marrow osteoprogenitors express estrogen receptor-alpha and bone morphogenetic proteins 2 and 4 mRNA during osteoblastic differentiation. J. Cell. Biochem. 75: 382-92 (1999).

Pack et al., "Improved Bivalent Miniantibodies, with Identical Avidity as Whole Antibodies, Produced by High Cell Density Fermentation of *Escherichia coli*," *Bio/Technology*, 11:1271-1277 (1993).

Pelletier et al., "Modulation of the Expression of Glucocorticoid Receptors in Synovial Fibroblasts and Chondrocytes by Prostaglandins and NSAIDs," *Am. J. Ther.*, 3:115-119 (1996).

Pereira et al., "Bone Morphogenetic Proteins Induce Gremlin, a Protein that Limits Their Activity in Osteoblasts," *Endocrinology*, 141(12): 4558-4563 (2000).

Pereira et al., "The Adeno-Associated Virus (AAV) Rep Protein Acts as Both a Repressor and an Activator to Regulate AAV Transcription during a Productive Infection", *J. Virol.*, 71(2):1079-1088 (1997).

Pittenger et al., Multilineage potential of adult human mesenchymal stem cells. Science. 284: 143-7 (1999).

Plunkthun, The Pharmacology of Monoclonal Antibodies, Springer-Verlag, NY, 113: 269-315 (1994).

Pockwinse et al., "Expression of Cell Growth and Bone Specific Genes at Single Cell Resoultion During Development of Bone Tissue-Like Organization in Primary Osteoblast Cultures," *J. Cell. Biochem.*, 49: 310-323 (1992).

Postwinse et al., Expression of cell growth and bone specific genes at single cell resolutions during development of bone tissue-like organization in primary osteoblast cultures. J. Cell. Biochem. 49: 310-23 (1992).

Presta, "Antibody engineering," *Curr. Opin. Struct Biol.*, 2:593-596 (1992).

Reichman et al., "Reshaping human antibodies for therapy," Nature, 332: 323-329 (1988).

Roy et al., "Syntheses and Exploration of New Biological Activities in Ethyl 6/7-Substituted and 6, 7-Disubstituted Quinolin-4-One-3-Carboxylates #," Bioorganic & Med. Chem. Letters, 6(2):121-126 (1996).

Ruffing et al., J. Gen. Virol., "Mutations in the carboxy terminus of adeno-associated virus 2 capsid proteins affect viral infectivity: lack of an RGD integrin-binding motif", 75:3385-3392 (1994).

Sambrook et al., Molecular Cloning: A Laboratory Manual. 2nd Edition. Cold Spring Harbor Laboratory Press (1989).

Sambrook et al., Molecular Cloning: A Laboratory Manual. 3rd Edition. Cold Spring Harbor Laboratory Press (2001).

Scherr et al., "Gene Silencing Mediated by Small Interfering RNAs in Mammalian Cells," *Curr. Med. Chem.*, 10: 245-256 (2003).

Selegny, Bulletin de la Societe Chimique de France, 1275-82 (1959).

Song et al., "Glucocorticoid receptor inhibits transforming growth factor-β signaling by directly targeting the transcriptional activation function of Smad3," *Proc. Natl. Acad. Sci. USA.*, 96: 11776-11781 (1999).

Srivastava et al., "Nucleotide Sequence and Organization of the Adeno-Associated Virus 2 Genome", *J. Virol.*, 45(2):555-564 (1983).

Suzawa et al., Extracellular matrix-associated bone morphogenetic proteins are essential for differentiation of murine osteoblastic cells in vitro. Endocrinology. 140: 2125-33 (1999).

Takiguchi et al.,. "Effect of prostaglandin E2 on recombinant human bone morphogenetic protein-2-stimulated osteoblastic differentiation in human periodontal ligament cells," *Jour. of Periodontal Res.*, 34: 431-436 (1999).

Tanaka et al., "Ursodeoxycholic Acid-Dependent Activation of the Glucocorticoid Receptor," *Biochemical and Biophysical Research Communications*, 188(2): 942-948 (1992).

Thornberry et al., "Caspases: Enemies Within," *Science*, 281: 1312-1316 (1998).

Vaswani et al., "Humanized antibodies as potential therapeutic drugs," *Ann Allergy Asthma Immunol*, 81: 105-119 (1998).

Vaughan et al., "Surviving Apoptosis," *Apoptosis*, 7: 173-177 (2002).

Wang et al., Bone morphogenetic proteins (BMPs): therapeutic potential in healing body defects. TIBTECH. 11: 379-83 (1993).

Weston et al., "Regulation of Skeletal Progenitor Differentiation by the BMP and Retinoid Signaling Pathways," *J. Cell Biol.*, 148(4): 679-690 (2000).

Whitlow et al., "Single-Chain Fv Proteins and Their Fusion Proteins," *Methods: a Companion to Methods in Enzymology*, 2(2): 97-105 (1991).

Winkler et al., "Sclerostin, the Protein Product of the Sclerosteosis Gene (SOST) and a Key Regulator of Bone Matrix Formation, Binds to BMPs and Antagonizes Their Function," *J. Bone Min. Res.*, 16: Suppl. 1: S322 (2000).

* cited by examiner

*No bands for gremlin, noggin in absence of RT

DEX = dexamethasone
Triam = triamcinolone
Urso = ursodeoxycholic acid (2 concentrations tested)

DEX = dexamethasone
Tauro = tauroursodeoxycholic acid
Fluo = fluocinolone acetonide
Lova = lovastatin
ICI = ICI 182,780
Estogen = 17β-estradiol
PGE2 = prostaglandin E2

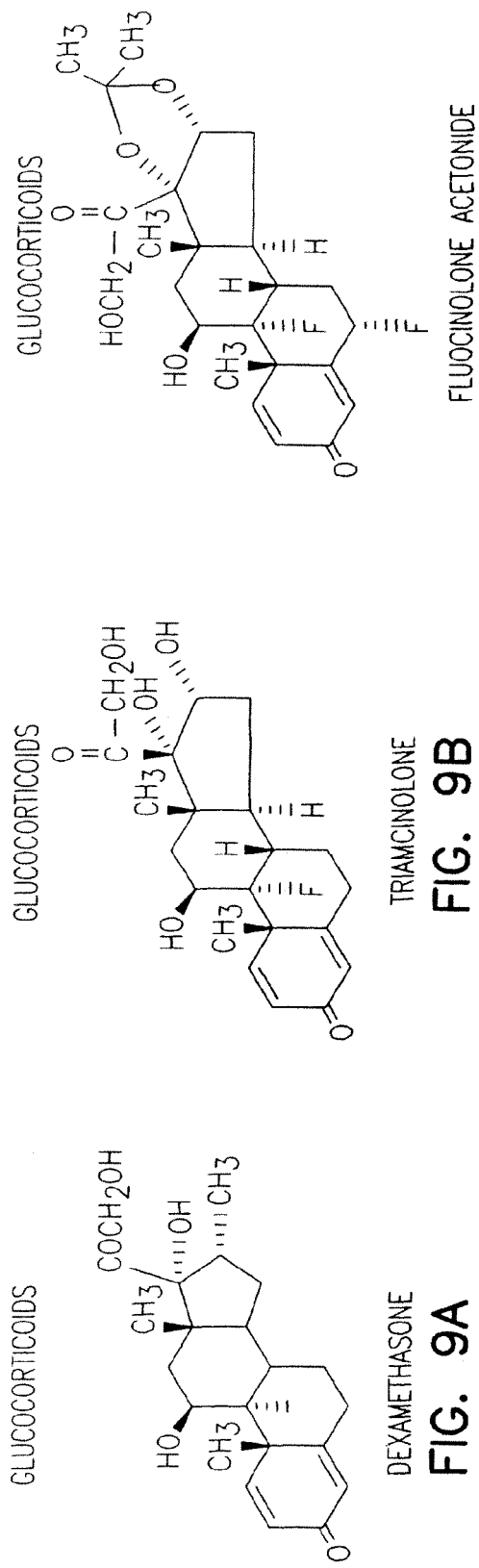
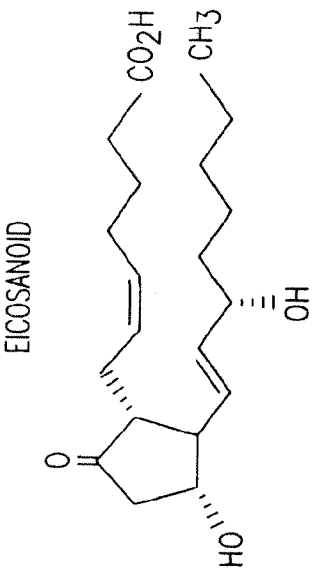
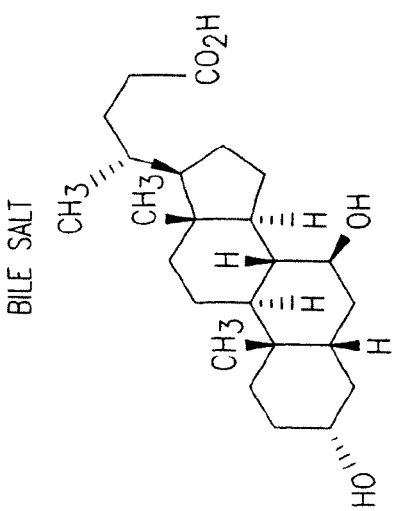
FIG. 9A DEXAMETHASONE (GLUCOCORTICOIDS)
FIG. 9B TRIAMCINOLONE (GLUCOCORTICOIDS)
FIG. 9C FLUOCINOLONE ACETONIDE (GLUCOCORTICOIDS)
FIG. 9D URSODEOXYCHOLIC ACID (BILE SALT)
FIG. 9E PROSTAGLANDIN E2 (EICOSANOID)

```
                              SEQUENCE LISTING

<160> NUMBER OF SEQ ID NOS: 44

<210> SEQ ID NO 1
<211> LENGTH: 21501
<212> TYPE: DNA
<213> ORGANISM: Homo sapiens

<400> SEQUENCE: 1 accccatcc ccagctccca gggcctctgc cacgcgggct tcttttttt tttgagacag      60 agtctcgctc tgtcacccag gctggagcac aatctcagca caatctcacc tcaccgcaac     120
ctctgcctcc tgggttcaag caattctctg gcctcagcct cctgagtagc tgggattata     180
ggctcgcgcc accacaccca gctatttttt tgtatcttta gtaaagacgg gatttcacta     240
tgttggccag tctggtctcg aactcctgac cttgtgatca agttgccttg gcctcccaaa     300
gtgctgggat tacaggcgtg agccactgtg cccagcccct tgcaggcttc tgacagcaca     360
gatggttttg cccgctttcc tactctgtgg gctcatccac ctcatatgtg tgtgctgcct     420
ccgtgttgct tctgctaagt ggcagtctgg tcattctttg tatttgtcct ttctactgtg     480
gatgggcctt tgggggtttc taactgtggg ccatgatgtg cagtgttgcc tgtgaacatt     540
ctggcccatg ttcgtgaatg tgaatgcgta tctctattgg acctgggcct gggagtggga     600
ttgctgggcc agaggggatg cacgtgttca gcttgaggag ataccgccgt gccgcacagc     660
tttccaaagt ggttgtgcca attcacgcct cacctccccc agccacgcag aagagttcca     720
gttgccccat atcttcacca gcactttggg ttttccatcc ttttcatttt agccattctg     780
acaggcacac agtggcgtga cattgtgctt ttaagtggca cttcacggaa gagtcttgac     840
caacgccatg gtgtgatggg acgccccag ctcaccacgt ctcccctgtt tcttacaggc     900
cgggtgctcg tccactgccg ggaaggttat agccgctccc caacgctagt tatcgcctac     960
ctcatgatgc ggcagaagat ggacgtcaag tctgccctga gcatcgtgag gcagaaccgt    1020
gagatcggcc ccaacgatgg cttcctggcc cagctctgcc agctcaatga cagactagcc    1080
aaggagggga agttgaaacc ctagggcacc ccaccgcct ctgctcgaga ggtccgtggg    1140
ggaggccgtg ggcaaaggtg tcccgagctg ccatgtttag gaaacacact gtaccctgct    1200
cccagcatca caaggcactt gtctacaagt gtgtcccaac acagtcctgg gccactttcc    1260
ccaccctggg gagcacataa agaagcttgc caaggggggc gtccttgctc cccagttgtc    1320
ctgtttctgt aacttatgat gtcttttccc tgagatgggg gctcagaggg ggaaggcctg    1380
tggcctgcat gcttcccgat ggcccacggc aggaggtgtg tggaagtgta aggcctaaga    1440
tgctcacaga ggtccctcat gacctcccct ccccaactcc cgaatcctct cttgagtgtg    1500
gacctcaaca ccttgagccc tagtaaagga actatgcaaa tgcaggccac tctccccacc    1560
acgtctgtgc ccgcactgt ccccacagcc ttccacaccc tgtgcatagg cagccctctc    1620
acgtcttgag gtccgaagct ggggtggggg tgtccgtcag ttattagtgg atggagattc    1680
ccacagcaag gctgcatttg aatgatttcc ttaggatgaa tggtccctac acaaagaggc    1740
cttgtgggca aacctggaga accctcctaa atccatagag ttttcaaaat gtgaatcttt    1800
ggaagccttg agttcagaat ctgctgctct ggaatatttc ccttcgatct tatctcagtc    1860
acttcgtttt tgagaagagt gatgccttgg gcatgctttt ttttttttct tttttagaaa    1920
```

```
acagggagtt gaagtccaac ctatttaaaa accccaccat ttggagaatt acaagggttt    1980
tgtcctgaat tgtagtgttg gcaagcccaa gccactcgtg ctaactgctt tttgtctcgg    2040
ttgctattcc aagaacagaa ggaggaagtt ggccaattac agcgtgtgtg catggatgtg    2100
tgtgggggc gtgcctctca gaaacgcggc cagaagacaa gcagggaagt gaaaggtccc    2160
aggcacacac cctgcccatt gcaggtggct cttacagctc tctggtgcca gcacgggatc    2220
cctgaagtga ctcagccagg cagacatgag acatggcgga gtgtccaaat ggatccttta    2280
ttggtggtag agcaaaaaaa cccaaacacg ataaaccttt caaaagactt tctaaggatg    2340
atattggaat gcaccagccc tcacatgtgt atgcacattt gccagaatat aagagttttg    2400
ttttaaatac agtcttgtta ggattttacg ttattgttat tatggaaagt gattgtgatg    2460
ctatttatct tcagggtcac tctgggcaaa gagaaggtcc tcagccatgc ccccagcacc    2520
ttgcacatag gtgtctgata aaagtttaag aaattaaaca cttttttgagc accaaatata   2580
tatagggcat tgttctggtg ggtgtgtcac gctcccagaa gactgaattt atggtaggat    2640
cactcgcaag gccttgtgaa ggagtcttac ctaaaacaaa agaaatatca gggacttttg    2700
ttgactattt acaactcagt tttacattta aattcaggca gtgttaatat gccaaggtag    2760
ggaatgtgcc ttttcagag ttggccagga gctcctggct gggacacgga gaggcaggtg    2820
tggcgtaagg cctcactccc ggctgtgaag gtctctgatc acacagaagc agccctgccc    2880
agcctggtca tttgctgtcc gcttttctct gtgaccacag cagccctgaa caaccagtat    2940
gtgtcttctt ctccagatag tgaaaaaggt gtccagataa acccacctaa gtgaaatggc    3000
catcctctaa actgggtacc tcactgcaca gcttctaggt agccttccaa cttaatctaa    3060
cttgagcctc acagtaaccc tgtaaagtta gtagagcttg ttcttgtatt gtgacctttt    3120
ttaaaaaaaa ggaactgagg ttcagaatga ttaagggcct ggcccccagg ttgtccagc    3180
tccataaggt ggagctgggc aagatttggg gtttgctgct ccctgaagct ggattctttc    3240
atacgatact ctttctcaag aaggggctc cctgggatct ccaggtgtac tgcacttacc    3300
ctcaatccag ccccggagaa gcaagtgaaa agggtgggtc cctcataggc tagaatgtgc    3360
agctcttct ccaggtggga tgtagcaccc caaagtagag ctttctgctc tgctcctgga    3420
aaaggctagg gagctgggc tggggctccc ctcccatgac caggcagtgg tcaccccatg    3480
ggacaggcac agctacttac gcgaacacag caggttggtg tggctggcta actaggacct    3540
ctcgaaagtc tctgtggggg catgagggag aaaaggccat tgggagaatt actgccttta    3600
ctttgggact acttttatgc tgataacttg ggatttcttg atagtccttc acccctgaaa    3660
ccccgtattt acttaacaag atttagctct tagttcttca agtaaaatta agtctcttg    3720
tgtaagagcc aacacatgcc cagctgcgga tgggagctgt tcctggacag ccttctactg    3780
cctgggaagt gatggaacag gaactcaggg tgcccttacc ccctccccag acctgttccc    3840
tttcttgac tgacagagca ccatccaggc aaaattagag cgccaaatgg ttttcttctc    3900
aatcttaaag cagtatacct ttccacaggc tcgtctgtgt ccctgccact ctgagttatc    3960
cagaaaccac cacctacaaa tgagggggact catctagaag acctctaagg tccccttttg   4020
gctctgaggg gtctctaata atccccactt ggaattcagc accgcaagga aattatgggt    4080
atgtgagcca taatatgatg gccagcaggt ggcgctgcct tccacccatg gtgatggatg    4140
gtttggaaag ggaatgttgg tgccttttgt gccacaagtt aagatgctac tgttttaaag    4200
gaaaaaaaaa aaaaaagta ctgatcttca atatgaagac atgagcttt ctcgcaggaa    4260
attttctttt tcacagaact ggtgtcagga atcactgaag ggctaaccgt gatagtcctt    4320
```

```
gcaagtaagt caaggtttta tcctgattgg aaatagaaga catttccggt tgagagaaca    4380
gattcgttgg aagcttaact tttgttgcct cttaacgcca ccaaatttta gggtaatttg    4440
attatgaaag agtgaatttt tctggacaga aaagggagag ctaccaaatt gttttttttct   4500 ttttaaaagg aagtttaatg tccgttgtat cacaaatcag tgttaaaaca ccagaacttt    4560
agccaaaata aatgtcttac attacaaagg tattgttttt ttgtccttct tatcacagtt    4620
ggtattcttt tacgtttta tgcttagctt tttttgtttg ggcttagctt ttatatttgc     4680
gatttctaac tttttaaaaa taatcatcta aaacatagcc gttctgagct agttataggt    4740
tccatgatgg cactgtttat gcagtagata ttgatgaaca cctttccagt accagaaatg    4800
ttctggtagg aatattctta ggtagaatgg ccataatggt cctgaatgaa ggaggtaagg    4860
tttgtgcttc taagaaagca ggggactagg gtgttcatct caaggtagcc tcacgtgatg    4920
actgggtgac attttgagat ttgagtgatc ctgcaaatga acagtcccta aacatatccc    4980
cttcccccag atgccttaaa ttccactatt ggtgctatgt cctttgaat aaaaaacctt     5040 agagaaagta ggtgcctttt cctcccagac agaagtctgg gcagagaaag cctctcgagg    5100
ttcccattcc ctctatcaca tgaagcaatt ggactcgctt cctatttgtc aagactctga    5160
caatgtaatc tttatggttc tacacaaaat cttaaggcag agcactaaaa tataaaacag    5220 gtaaagttt ttaagtataa ttttaaaaa atttttcatt aaaataata ctatatgtac       5280 atagtaatac acttaaacaa tgcaaaaggc ttatacggaa aagtgagtca cttgctcctt    5340
caatctatct ccccataagc gtcatatcct taaaggaaaa tgtcaagcat atataagcac    5400
acatatgtgc atacgtgtgt atatacagag atatctctgc tttgttgttt gttttgctta    5460
gcttatatta tggttattgt ttttattgct ctaccccctt catcttaaca gctacatagc    5520
attccattgt gtatggatgt gtaaataaag acaaggtgat ttggacatcc ctcaatgcag    5580
ggtactgcct aaaagcagaa gtttgccctc ctaatccaga tatttccttt ttaccaccta    5640
caagtgggag caaaatctgt tttaaaatgc agccaataag gagaatcctc agtttccatt    5700
aattagagat agggggcctcc tccagaacca agtagagaat gaaaccggat gacctttgag   5760
agtccttcca gatcaaagat tctatgatcc caaggagtca aaggagcata atatactttc    5820
caaatttggc ctgtcattca agtctggtc caaatgccac atcttaccat aaggatccca     5880
gatcctcccc aggggaaaga gattgttctc tcctttgaag gcccataaga aaattgtcct    5940
tttgaaaaaa tgcatctggt gaggatgtgg aacaacagga actctttgtt tcagtgggga    6000
atgcaaaatg gtacagccac tttggaggac agtttgcagt ttagtttctt gcaaaactac    6060
acatactttt attgcacaat ccagcagtca tgctccttgg tatttattca aatgatttga    6120
aaacttaacg ttcgtataaa aacctgcaca cagctgggca tggtggctca tgcctgtaat    6180
cccagcactt tgggaggctg aggtgggcag atcacttgag gttaggagtt tgagaccata    6240
ctggccaaca tggggaaacc ccttctctac taaaaataca aaaattagcc aggtgtggtg    6300
gtgctcacct gtaatcccac ctactcggga ggctgagcca ggagaatcac ttgaacccag    6360
gaggcggagg ttgcagtgag ctgagatcac ggcactgcac cccagcctgg gagacagagt    6420
aagactccgt cttaagacaa aacaaaacaa aaacctgta caaatgtttt ataccacctc     6480
tattaataat tgccagagct tgaaagcaac caagatgtcc ttcagtagat gacagtaggt    6540
gactagataa accgtgatac atcaagacga tggagtatta ctcagtgcta aaaaaaaaaa    6600
taagctgttc atgccatgaa aagacatgga ggaaccccaa atgaatatta ctaactgaaa    6660
gaagccaatc tgaaaagact atgtatgggt atattccaac tctatatgac atcctggaaa    6720
```

```
aggcaaaaat aaaggtacag taaaaagatc agtggttgcc aggggttggg gaaagtcggg    6780
gagggatgaa taggcagagc agatagtttt tttggacaat gaaaatactg cccatctgta    6840
tgatactata atggtagatg tatgtcatta tacatttgtc caaagccata ggatgtacaa    6900
cactagtgct gtgatgtaaa ccatggactt caggtgataa tgatgtgtca tgtaggctca    6960
tcaatcatag caaatgcacc actctggtgg cgggatgttg ataacggggg cagctgtaca    7020
tgtgtgggca caggacataa atgagaaatc tctgtaccat ccactcagtt ttgctgtgaa    7080
cctaaaagtg ctccagaaaa aaaataaagt ttttttaga aaaaagcatc tgaacctttt    7140
tttcagtggc attgatcacc ttccatctgg tagtggagtt gtttggatgc ggaaattatt    7200
tcttccatgg tatgcgagct cctggagagg gagtgcgtgt cccccttgct ttattaaacg    7260
tttggcgagt gaacatcaga agaagcaact cgacagaaac aaaagctggt aaataatcac    7320
atggaaaagc agcttttctg gaaattaagt ttcaactgtt aaattcaatg tttaaaaaaa    7380
tcggctgggt gcggtggctc ccgcctgcaa tcccagcact ttatgggatt gtgggaacac    7440
ctgatgtcag gagttcaaga ccagcctggc cgacatggcg aaaccccatc tctacaaaac    7500
aaacaaaaaa aaatgcaaaa attagctggg tgtggtggcg ggagtctgta gtcctagcta    7560
ctcgggaggc tgaggcagga gaactgcttg aacccaggag gtggaggtta tatgagccaa    7620
gatcacacca ctgcactccc gcctgggtga cagagcgaga ctctgtctca aaaaaaaaaa    7680
aaaaaatcaa catcccaaac ccagtgttga cagtcttatt tatgggttga actgcattcc    7740
tcccaaatgc atatattgaa gtcctaagtc acagtacctg agaatgtgac cttatttgga    7800
aatagggcta ttacagatgt aactcgttaa gatgaggtca ttaggctggg cctaatctaa    7860
tatgcctgac ctccttagaa aaagggaaa attcgaacac agagagaaca ccatgtgaag    7920
atgaaggcag ggattggggg tgacacttct gcaagccagt gaatgccaca gcttgtcagc    7980
agccagcaga aggcaggtaa aaggccttcc tcactgtcct cgaaggaacc aactctgcca    8040
atgtcttgaa cttgcactcc taacctccag ctctgtgaga cgacttctgt tgtttatgcc    8100
acccaatttg tggtacttag ttacggcagc ctcatcaaag taccacctat gggagcctct    8160
attttgcagg tgagggcggg gactgggctg agttttctgg aaaacagccc tgcaataccc    8220
tcatcagacc accaaactct tcacactccc tcagacacag cattcacttc cagaaataac    8280
tctaaagttt tgttttgttt ttttaaactt tgtggaatac tactcagcca aaaaaaaaaa    8340
aaaagaaaag aaaaaggaac atgttactga tatgtacaac ttggataatg gaaataatgc    8400
tgagtgaaaa aaaaatcccc aaaggctaca tactaattga ttccatttat ataacctttt    8460
tttttttttt ttgagacagt ctcactctgt cacccaggct ggagcacagt ggcgcgatct    8520
cagctcactg caacttccgc ctcctgagtt caagcgattc tcttgcctta gcttcccaag    8580
tagctgggat tacaggtgcg tgccaccatg cccagctaat ttttgtattt ttagtagaga    8640
cagggtttcg ccatgttggc caggctggtc tcgaactcct gacctcaagt gatctgcctg    8700
ccttggcttc ccaaagtgct gggattacat gagtgagcca ccgcacctgg tcgcatttat    8760
gtaacaattt tgaagtgaaa aaaaaatga cagaaatgga gattagatga gtagttgcca    8820
ggggttagtt gtgggaggga gggaaaagga gggaaggagg tgggcaacag gagaaagact    8880
tgtggtcaca gagctgtgct ttatcttgac tgtggtggat cccaaatttt acccgtgaca    8940
agattgcata gaactaagta tacacacacg tgaatgcgtg tgcacgcaca cagtagaggt    9000
taagccacgg gagatgtggg taagattggt aaattgtgtc aatatcaata tcctagttgt    9060
gatattgtcc tatagtttcg caaggtgtta ttgttgtggg aaactggata aaggatacac    9120
```

```
ggagtctgca tttctttttt tttatttta tttttgaga cggggtctca ctctgtcaac  9180
caggctggag tgcagtggcc caagtatggc tcactgcagc ctcgacctca acctcaagtg  9240
aacctcccac ctcagcctcc caagtagcta agaccacagg cgtgcgaccc catgcccagc  9300
taatttttaa atttttgta gagactaggc ctcaccatgt tgcccaggct tttatttctt  9360
ataagtatat ttaaatttat aattatatcc acattttaaa attttaattt aaaaaattac  9420
tctgaggccg ggcattgtgg ctcatgcctc taatcccag caccttggga ggccgagttg  9480
ggcagatcac ccgaggtcag aagttcgaga ccagcctgag taacatggag aaaccccgt  9540
ctctactaaa aatacaaaat tggccgggcg tggtggtgca ttcctgtaat cccagctact  9600
cgggaggctg aggcaggaga attgcttgaa cccaggaggt ggaggttgca gtgagccaag  9660
attgtgccac tgcactgcag cctgggccac agagagaatc tgccaaaaaa agaaaaaaaa  9720
aaaaatttca gccgtacaag gatgttcata gcaaccctgc tggaaatagg aaaaaaaatt  9780
ggaaataacc taaactactc acaataggaa tcagctaaaa ccctgggggt ttaattccag  9840
ggaatactgt gaacaatgac aagtttgtgg actgagtaaa aataaacagc tgtcaatgac  9900
ttaacattaa atgaaacagc agaagatgtc acagcaggtt ctcgctgagc cattcagagg  9960
ggtgtggatc atttagaggt tcaagtccac tggattcttc tttttccttt taatattact  10020
tcacttccaa ataaggaaag gaaggaaag gaaatcacgt ccagtcctga gacttgccat  10080
cctgcagtca cccctccttt tgtctccagc aggtggcaga cgcgttccag ggatgaatcc  10140
cactgcctct gtttaatgca gacggtccag ccgctcccaa cagcaggtgg ggctataagc  10200
atccatccta cctgctcaag gaacccaggc atcagaactg ctctctccca agtccattgc  10260
aagaaggcag tcgtctggtc atgagagggt taacagtcca cattccagag caagggaaaa  10320
ggaggctgga gggtcataga caaggggagg tggtgcggag ggccagcttc tcacaacact  10380
accggctctg ctgggagaga tagatacccc ccaacaatgg ccacagctgt tttcatctgc  10440
cctgaaggaa actgacttag gaagcaggta tcagagaggg cccttcctga ggggcttct  10500
gtctggcttg taaaactgtc agagcagctg cattcatgtg tcggatgatg gatgatggaa  10560
aggacagtcg gctgcagatg gacacagcga cttgcaagtt gaggcaggtg gcaaaggact  10620
tgcagaggct ctgcaggtgg ggcatgctga ttcattgccc agttaaaata ccagaggatc  10680
tgggcagcct cttcacagga gctgcttgtc ctcaaacaat ctgtcttcaa tgaaagattc  10740
ctctggcctt cctttctctt cttgcacctc aggtgtgaat ccttctcccc cacgcctcta  10800
cctgcgcccc cgccccccgc ccggccctg tgtggctcat tatatgcagg gccaaggcag  10860
cattttctct tagcttcttt gtgaccagtt ggtcctggga tggcttcatg gaacacatcc  10920
tgtggtgtgc accaatgaag ctttccatac aggactcaaa actgttttg aaaaatgtaa  10980
ccagctggaa gacaagaaaa taaaatgtca gcactaaaaa cgctggctgt ggcttttgct  11040
aaggaaagga atttggtgtt gtcttctcac acacacagac tggttgggga aatgactgtc  11100
ttcagcacat caccctgcga gccacagtga gtgccctggc tcagaagtgc ctgtcacagt  11160
gcacaggatc cctgaggagc atgagctggg atttcctctg tgctgtccat cacaggagcc  11220
tgagtgacca gcgcatcctc gatttgtaac cagaatcctg ccctctctcc caagcgggca  11280
cccttgctct gaccctctag ttctctctct tgccttccag agaataccaa gagaggcttt  11340
cttggttagg acaatgaatg ctgagacttg tggagttggg accaatggga tttcttaaa  11400
agcatctttt tgcctctggc tgggtctatg ggggtcaaac agaaacacct tgggccattt  11460
gttggtgggg tgacaaatga acttggcctg agaaatggaa taggccgggc tcagccccgc  11520
```

```
gaagcactca gaactgcaca ttttctttgt tgagcgggtc cacagtttgt tttgagaatg    11580
cccgagggcc cagggagaca gacaattaaa agccggagct cattttgata tctgaaaacc    11640
acagccgcca gcacgtggga ggtgccggag agcaggcttg ggccttgcct cacacgcccc    11700
ctctctctgg gtcacctggg agtgccagca gcaatttgga agtttgctga gctagaggag    11760
aagtctttgg ggagggtttg ctctgagcac acccctttcc ctccctccgg ggctgaggga    11820
aacatgggac cagccctgcc ccagcctgtc ctcattggct ggcatgaagc agagaggggc    11880
tttaaaaagg cgaccgtgtc tcggctggag accagagcct gtgctactgg aaggtggcgt    11940
gccctcctct ggctggtacc atgcagctcc cactggccct gtgtctcgtc tgcctgctgg    12000
tacacacagc cttccgtgta gtggagggcc aggggtggca ggcgttcaag aatgatgcca    12060
cggaaatcat ccccgagctc ggagagtacc ccgagcctcc accggagctg gagaacaaca    12120
agaccatgaa ccgggcggag aacggagggc ggcctcccca ccaccccttt gagaccaaag    12180
gtatggggtg gaggagagaa ttcttagtaa aagatcctgg ggaggtttta gaaacttctc    12240
tttgggaggc ttggaagact ggggtagacc cagtgaagat tgctggcctc tgccagcact    12300
ggtcgaggaa cagtcttgcc tggaggtggg ggaagaatgg ctcgctggtg cagccttcaa    12360
attcaggtgc agaggcatga ggcaacagac gctggtgaga gcccagggca gggaggacgc    12420
tggggtggtg agggtatggc atcagggcat cagaacaggc tcaggggctc agaaaagaaa    12480
aggtttcaaa gaatctcctc ctgggaatat aggagccacg tccagctgct ggtaccactg    12540
ggaagggaac aagtaaggg agcctcccat ccacagaaca gcacctgtgg ggcaccggac    12600
actctatgct ggtggtggct gtccccacca cacagaccca catcatggaa tccccaggag    12660
gtgaaccccc agctcgaagg ggaagaaaca ggttccaggc actcagtaac ttggtagtga    12720
gaagagctga ggtgtgaacc tggtttgatc caactgcaag atagccctgg tgtgtggggg    12780
ggtgtggggg acagatctcc acaaagcagt ggggaggaag gccagagagg cacccctgca    12840
gtgtgcattg cccatggcct gcccagggag ctggcacttg aaggaatggg agttttcggc    12900
acagttttag cccctgacat gggtgcagct gagtccaggc cctggagggg agagcagcat    12960
cctctgtgca ggagtaggga catctgtcct cagcagccac cccagtccca accttgcctc    13020
attccagggg agggagaagg aagaggaacc ctgggttcct ggtcaggcct gcacagagaa    13080
gcccaggtga cagtgtgcat ctggctctat aattggcagg aatcctgagg ccatgggggc    13140
gtctgaaatg acacttcaga ctaagagctt ccctgtcctc tggccattat ccaggtggca    13200
gagaagtcca ctgcccaggc tcctggaccc cagccctccc cgcctcacaa cctgttggga    13260
ctatggggtg ctaaaaaggg caactgcatg ggaggccagc caggaccctc cgtcttcaaa    13320
atggaggaca agggcgcctc cccccacagc tccccttcta ggcaaggtca gctgggctcc    13380
agcgactgcc tgaagggctg taaggaaccc aaacacaaaa tgtccacctt gctggactcc    13440
cacgagaggc cacagcccct gaggaagcca catgctcaaa acaaagtcat gatctgcaga    13500
ggaagtgcct ggcctagggg cgctattctc gaaaagccgc aaaatgcccc cttccctggg    13560
caaatgcccc cctgaccaca cacacattcc agccctgcag aggtgaggat gcaaccagc    13620 ccacagacca gaaagcagcc ccagacgatg gcagtggcca catctcccct gctgtgcttg    13680
ctcttcagag tgggggtggg gggtggcctt ctctgtcccc tctctggttt ggtcttaaga    13740
ctatttttca ttctttcttg tcacattgga actatcccca tgaaacctttt ggggtggac    13800 tggtactcac acgacgacca gctatttaaa aagctcccac ccatctaagt ccaccatagg    13860
agacatggtc aaggtgtgtg caggggatca ggccaggcct cggagcccaa tctctgcctg    13920
```

```
cccagggagt atcaccatga ggcgcccatt cagataacac agaacaagaa atgtgcccag   13980
cagagagcca ggtcaatgtt tgtggcagct gaacctgtag gttttgggtc agagctcagg   14040
gcccctatgg taggaaagta acgacagtaa aaagcagccc tcagctccat cccccagccc   14100
agcctcccat ggatgctcga acgcagagcc tccactcttg ccggagccaa aaggtgctgg   14160
gaccccaggg aagtggagtc cggagatgca gcccagcctt ttgggcaagt tcttttctct   14220
ggctgggcct cagtattctc attgataatg agggggttgg acacactgcc tttgattcct   14280
ttcaagtcta atgaattcct gtcctgatca cctccccttc agtccctcgc ctccacagca   14340
gctgccctga tttattacct tcaattaacc tctactcctt tctccatccc ctgtccaccc   14400
ctcccaagtg gctggaaaag gaatttggga gaagccagag ccaggcagaa ggtgtgctga   14460
gtacttaccc tgcccaggcc agggaccctg cggcacaagt gtggcttaaa tcataagaag   14520
accccagaag agaaatgata ataataatac ataacagccg acgctttcag ctatatgtgc   14580
caaatggtat tttctgcatt gcgtgtgtaa tggattaact cgcaatgctt ggggcggccc   14640
attttgcaga caggaagaag agagaggtta aggaacttgc ccaagatgac acctgcagtg   14700
agcgatggag ccctggtgtt tgaacccag cagtcatttg gctccgaggg gacagggtgc    14760
gcaggagagc tttccaccag ctctagagca tctgggacct tcctgcaata gatgttcagg   14820
ggcaaaagcc tctggagaca ggcttggcaa agcagggct ggggtggaga gagacgggcc    14880
ggtccagggc aggggtggcc aggcgggcgg ccaccctcac gcgcgcctct ctccacagac   14940
gtgtccgagt acagctgccg cgagctgcac ttcacccgct acgtgaccga tgggccgtgc   15000
cgcagcgcca agccggtcac cgagctggtg tgctccggcc agtgcggccc ggcgcgcctg   15060
ctgcccaacg ccatcggccg cggcaagtgg tggcgaccta gtgggcccga cttccgctgc   15120
atccccgacc gctaccgcgc gcagcgcgtg cagctgctgt gtcccggtgg tgaggcgccg   15180
cgcgcgcgca aggtgcgcct ggtggcctcg tgcaagtgca agcgcctcac ccgcttccac   15240
aaccagtcgg agctcaagga cttcgggacc gaggccgctc ggccgcagaa gggccggaag   15300
ccgcggcccc gcgcccggag cgccaaagcc aaccaggccg agctggagaa cgcctactag   15360
agcccgcccg cgcccctccc caccggcggg cgcccggcc ctgaacccgc gccccacatt     15420
tctgtcctct gcgcgtggtt tgattgttta tatttcattg taaatgcctg caacccaggg   15480 caggggggctg agaccttcca ggccctgagg aatcccgggc gccggcaagg cccccctcag   15540
cccgccagct gaggggtccc acggggcagg ggagggaatt gagagtcaca gacactgagc   15600
cacgcagccc cgcctctggg gccgcctacc tttgctggtc ccacttcaga ggaggcagaa   15660
atggaagcat tttcaccgcc ctggggtttt aagggagcgg tgtgggagtg ggaaagtcca   15720
gggactggtt aagaaagttg gataagattc ccccttgcac ctcgctgccc atcagaaagc   15780
ctgaggcgtg cccagagcac aagactgggg gcaactgtag atgtggtttc tagtcctggc   15840
tctgccacta acttgctgtg taaccttgaa ctacacaatt ctccttcggg acctcaattt   15900
ccactttgta aaatgagggt ggaggtggga ataggatctc gaggagacta ttggcatatg   15960
attccaagga ctccagtgcc ttttgaatgg gcagaggtga gagagagaga gagaaagaga   16020
gagaatgaat gcagttgcat tgattcagtg ccaaggtcac ttccagaatt cagagttgtg   16080
atgctctctt ctgacagcca aagatgaaaa acaaacagaa aaaaaaagt aaagagtcta    16140 tttatggctg acatatttac ggctgacaaa ctcctggaag aagctatgct gcttcccagc   16200
ctggcttccc cggatgtttg gctacctcca cccctccatc tcaaagaaat aacatcatcc   16260
attggggtag aaaaggagag ggtccgaggg tggtgggagg gatagaaatc acatccgccc   16320
```

```
caacttccca aagagcagca tccctccccc gacccatagc catgttttaa agtcaccttc    16380
cgaagagaag tgaaaggttc aaggacactg gccttgcagg cccgagggag cagccatcac    16440
aaactcacag accagcacat cccttttgag acaccgcctt ctgcccacca ctcacggaca    16500
catttctgcc tagaaaacag cttcttactg ctcttacatg tgatggcata tcttacacta    16560
aaagaatatt attggggggaa aaactacaag tgctgtacat atgctgagaa actgcagagc    16620
ataatagctg ccacccaaaa atcttttttga aaatcatttc cagacaacct cttactttct    16680
gtgtagtttt taattgttaa aaaaaaaaag ttttaaacag aagcacatga catatgaaag    16740
cctgcaggac tggtcgtttt tttggcaatt cttccacgtg ggacttgtcc acaagaatga    16800
aagtagtggt ttttaaagag ttaagttaca tatttatttt ctcacttaag ttatttatgc    16860
aaaagttttt cttgtagaga atgacaatgt taatattgct ttatgaatta acagtctgtt    16920
cttccagagt ccagagacat tgttaataaa gacaatgaat catgaccgaa aggatgtggt    16980
ctcattttgt caaccacaca tgacgtcatt tctgtcaaag ttgacaccct tctcttggtc    17040
actagagctc caaccttgga cacacctttg actgctctct ggtggccctt gtggcaatta    17100
tgtcttcctt tgaaaagtca tgtttatccc ttcctttcca aacccagacc gcatttcttc    17160
acccagggca tggtaataac ctcagccttg tatcctttta gcagcctccc ctccatgctg    17220
gcttccaaaa tgctgttctc attgtatcac tcccctgctc aaaagccttc catagctccc    17280
ccttgcccag gatcaagtgc agtttcccta tctgacatgg gaggccttct ctgcttgact    17340
cccacctccc actccaccaa gcttcctact gactccaaat ggtcatgcag atccctgctt    17400
ccttagtttg ccatccacac ttagcacccc caataactaa tcctcttcct ttaggattca    17460
cattacttgt catctcttcc cctaaccttc cagagatgtt ccaatctccc atgatccctc    17520
tctcctctga ggttccagcc cctttttgtct acaccactac tttggttcct aattctgttt    17580
tccatttgac agtcattcat ggaggaccag cctggccaag tcctgcttag tactggcata    17640
gacaacacaa agccaagtac aattcaggac cagctcacag gaaacttcat cttcttcgaa    17700
gtgtggattt gatgcctcct gggtagaaat gtaggatctt caaaagtggg ccagcctcct    17760
gcacttctct caaagtctcg cctccccaag gtgtcttaat agtgctggat gctagctgag    17820
ttagcatctt cagatgaaga gtaaccctaa agttactctt cagttgccct aaggtgggat    17880
ggtcaactgg aaagctttaa attaagtcca gcctaccttg ggggaaccca cccccacaaa    17940
gaaagctgag gtccctcctg atgacttgtc agtttaacta ccaataaccc acttgaatta    18000
atcatcatca tcaagtcttt gataggtgtg agtgggtatc agtggccggt cccttcctgg    18060
ggctccagcc cccgaggagg cctcagtgag cccctgcaga aaatccatgc atcatgagtg    18120
tctcagggcc cagaatatga gagcaggtag gaaacagaga catcttccat ccctgagagg    18180
cagtgcggtc cagtgggtgg ggacacgggc tctgggtcag gtttgtgttg tttgtttgtt    18240
tgttttgaga cagagtctcg ctctattgcc caggctggag tgcagtgtca caatctcggc    18300
ttactgcaac ttctgccttc ccggattcaa gtgattctcc tgcctcagcc tccagagtag    18360
ctgggattac aggtgcgtgc caccacgcct ggctaatttt tgtattttttg atagagacgg    18420 ggtttcacca tgttggccag gctagtctcg aactcttgac ctcaagtgat ctgcctgcct    18480
cggcctccca aagtgctggg attacaggcg tgagccacca cacccagccc caggttggtg    18540
tttgaatctg aggagactga agcaccaagg ggttaaatgt tttgcccaca gccatacttg    18600
ggctcagttc cttgccctac ccctcacttg agctgcttag aacctggtgg gcacatgggc    18660
aataaccagg tcacactgtt ttgtaccaag tgttatggga atccaagata ggagtaattt    18720
```

```
gctctgtgga ggggatgagg gatagtggtt agggaaagct tcacaaagtg ggtgttgctt    18780
agagattttc caggtggaga aggggggcttc taggcagaag gcatagccca agcaaagact    18840
gcaagtgcat ggctgctcat gggtagaaga gaatccacca ttcctcaaca tgtaccgagt    18900
ccttgccatg tgcaaggcaa catgggggta ccaggaattc caagcaatgt ccaaacctag    18960
ggtctgcttt ctgggacctg aagatacagg atggatcagc ccaggctgca atcccattac    19020
cacgaggggg aaaaaaacct gaaggctaaa ttgtaggtcg ggttagaggt tatttatgga    19080
aagttatatt ctacctacat ggggtctata agcctggcgc caatcagaaa aggaacaaac    19140
aacagaccta gctgggaggg gcagcatttt gttgtagggg gcggggcaca tgttctgggg    19200
gtacagccag actcagggct tgtattaata gtctgagagt aagacagaca gagggataga    19260
aggaaatagg tcccttctc tctctctctc tctctctctc tcactctctc tctctctcac    19320
acacacacac agacacacac acacgctctg tagggggtcta cttatgctcc aagtacaaat    19380
caggccacat ttacacaagg aggtaaagga aagaacgtt ggaggagcca caggacccca    19440
aaattccctg ttttccttga atcaggcagg acttacgcag ctgggagggt ggagagcctg    19500
cagaagccac ctgcgagtaa gccaagttca gagtcacaga caccaaaagc tggtgccatg    19560
tcccacaccc gcccacctcc cacctgctcc ttgacacagc cctgtgctcc acaacccggc    19620
tcccagatca ttgattatag ctctggggcc tgcaccgtcc ttcctgccac atccccaccc    19680
cattcttgga acctgccctc tgtcttctcc cttgtccaag ggcaggcaag ggctcagcta    19740
ttgggcagct ttgaccaaca gctgaggctc cttttgtggc tggagatgca ggaggcaggg    19800
gaatattcct cttagtcaat gcgaccatgt gcctggtttg cccagggtgg tctcgtttac    19860
acctgtaggc caagcgtaat tattaacagc tcccacttct actctaaaaa atgacccaat    19920
ctgggcagta aattatatgg tgcccatgct attaagagct gcaacttgct gggcgtggtg    19980
gctcacacct gtaatcccag tactttggga cgtcaaggcg ggtggatcac ctgaggtcac    20040
gagttagaga ctggcctggc cagcatggca aaaccccatc tttactaaaa atacaaaaat    20100
tagcaaggca tggtggcatg cacctgtaat cccaggtact cgggaggctg agacaggaga    20160
atggcttgaa cccaggaggc agaggttgca gtgagccaag attgtgccac tgccctccag    20220
ccctggcaac agagcaagac ttcatctcaa aagaaaaagg atactgtcaa tcactgcagg    20280
aagaacccag gtaatgaatg aggagaagag aggggctgag tcaccatagt ggcagcaccg    20340
actcctgcag gaaaggcgag acactgggtc atgggtactg aagggtgccc tgaatgacgt    20400
tctgctttag agaccgaacc tgagccctga aagtgcatgc ctgttcatgg gtgagagact    20460
aaattcatca ttccttggca ggtactgaat cctttcttac ggctgccctc caatgcccaa    20520
tttccctaca attgtctggg gtgcctaagc ttctgcccac caagagggcc agagctggca    20580
gcgagcagct gcaggtagga gagataggta cccataaggg aggtgggaaa gagagatgga    20640
aggagagggg tgcagagcac acacctcccc tgcctgacaa cttcctgagg gctggtcatg    20700
ccagcagatt taaggcggag gcaggggaga tggggcggga gaggaagtga aaaaggagag    20760
ggtgggggat gagaggaaga gagggtgatc attcattcat tccattgcta ctgactggat    20820
gccagctgtg agccaggcac cacccctagct ctgggcatgt ggttgtaatc ttggagcctc    20880
atggagctca caggggagtgc tggcaaggag atggataatg gacggataac aaataaacat    20940
ttagtacaat gtccgggaat ggaaagttct cgaaagaaaa ataaagctgg tgagcatata    21000
gacagccctg aaggcggcca ggccaggcat ttctgaggag gtggcatttg agctaagacc    21060
aaaatgtggt gggagaggga gccacacaag gatctggggg tgtgtgcact gggaggggga    21120
```

| | |
|---|---:|
| gcagcaagtg caaagggcct gaaggtatgt aggggggtgga gaagggacac cactaattgc | 21180 |
| cttgggtgcc tttcaggcgt ctccatgcca aggctctaac ccctgatgtg gaagccaaca | 21240 |
| tagtaattat aattatagtg aagaggggtg tgtgtgtgtg tgtgtgtgtg tgtgtgtgtg | 21300 |
| tgattgaaag agagagagaa tgagtctctg taccttctct tgggtctgta tgttgaaaac | 21360 |
| ctaagtgacc ctaaagaaga atatttgcat attattaatt atgtagctat acatgttttt | 21420 |
| tttgagacaa agtcttgctt tgtcacccag actggagtgc agtggcagca atcatggctc | 21480 |
| actgcagcct ctgcctccca g | 21501 |

<210> SEQ ID NO 2
<211> LENGTH: 2323
<212> TYPE: DNA
<213> ORGANISM: Homo sapiens
<400> SEQUENCE: 2

| | |
|---|---:|
| agagcctgtg ctactggaag gtggcgtgcc ctcctctggc tggtaccatg cagctcccac | 60 |
| tggccctgtg tctcgtctgc ctgctggtac acacagcctt ccgtgtagtg gagggccagg | 120 |
| ggtggcaggc gttcaagaat gatgccacgg aaatcatccc cgagctcgga gagtaccccg | 180 |
| agcctccacc ggagctggag aacaacaaga ccatgaaccg ggcggagaac ggagggcggc | 240 |
| ctcccccacca cccctttgag accaaagacg tgtccgagta cagctgccgc gagctgcact | 300 |
| tcacccgcta cgtgaccgat gggccgtgcc gcagcgccaa gccggtcacc gagctggtgt | 360 |
| gctccggcca gtgcggcccg gcgcgcctgc tgcccaacgc catcggccgc ggcaagtggt | 420 |
| ggcgacctag tgggcccgac ttccgctgca tccccgaccg ctaccgcgcg cagcgcgtgc | 480 |
| agctgctgtg tccggtggt gaggcgccgc gcgcgcgcaa ggtgcgcctg gtggcctcgt | 540 |
| gcaagtgcaa gcgcctcacc cgcttccaca accagtcgga gctcaaggac ttcgggaccg | 600 |
| aggccgctcg gccgcagaag ggccggaagc gcggcccccg cgcccggagc gccaaagcca | 660 |
| accaggccga gctggagaac gcctactaga gcccgcccgc gcccctcccc accggcgggc | 720 |
| gccccggccc tgaacccgcg ccccacattt ctgtcctctg cgcgtggttt gattgtttat | 780 |
| atttcattgt aaatgcctgc aacccagggc agggggctga gaccttccag gccctgagga | 840 |
| atcccgggcg ccggcaaggc cccctcagc ccgccagctg agggggtccca cggggcaggg | 900 |
| gagggaattg agagtcacag acactgagcc acgcagcccc gcctctgggg ccgcctacct | 960 |
| ttgctggtcc cacttcagag gaggcagaaa tggaagcatt ttcaccgccc tggggttttta | 1020 |
| agggagcggt gtgggagtgg gaaagtccag ggactggtta agaaagttgg ataagattcc | 1080 |
| cccttgcacc tcgctgccca tcagaaagcc tgaggcgtgc ccagagcaca agactggggg | 1140 |
| caactgtaga tgtggtttct agtcctggct ctgccactaa cttgctgtgt aaccttgaac | 1200 |
| tacacaattc tccttcggga cctcaatttc cactttgtaa aatgagggtg gaggtgggaa | 1260 |
| taggatctcg aggagactat tggcatatga ttccaaggac tccagtgcct tttgaatggg | 1320 |
| cagaggtgag agagagagag agaaagagag agaatgaatg cagttgcatt gattcagtgc | 1380 |
| caaggtcact tccagaattc agagttgtga tgctctcttc tgacagccaa agatgaaaaa | 1440 |
| caaacagaaa aaaaaagta aagagtctat ttatggctga catatttacg gctgacaaac | 1500 |
| tcctggaaga agctatgctg cttcccagcc tggcttcccc ggatgtttgg ctacctccac | 1560 |
| ccctccatct caaagaaata acatcatcca ttggggtaga aaggagaggg gtccgagggt | 1620 |
| ggtgggaggg atagaaaatca catccgcccc aacttcccaa agagcagcat ccctcccccg | 1680 |
| acccatagcc atgttttaaa gtcaccttcc gaagagaagt gaaaggttca aggacactgg | 1740 |

| | |
|---|---|
| ccttgcaggc ccgagggagc agccatcaca aactcacaga ccagcacatc ccttttgaga | 1800 |
| caccgccttc tgcccaccac tcacggacac atttctgcct agaaacagc ttcttactgc | 1860 |
| tcttacatgt gatggcatat cttacactaa aagaatatta ttgggggaaa aactacaagt | 1920 |
| gctgtacata tgctgagaaa ctgcagagca taatagctgc cacccaaaaa tcttttgaa | 1980 |
| aatcatttcc agacaacctc ttactttctg tgtagttttt aattgttaaa aaaaaaagt | 2040 |
| tttaaacaga agcacatgac atatgaaagc ctgcaggact ggtcgttttt ttggcaattc | 2100 |
| ttccacgtgg gacttgtcca caagaatgaa agtagtggtt tttaaagagt taagttacat | 2160 |
| atttattttc tcacttaagt tatttatgca aaagttttc ttgtagagaa tgacaatgtt | 2220 |
| aatattgctt tatgaattaa cagtctgttc ttccagagtc cagagacatt gttaataaag | 2280 |
| acaatgaatc atgaccgaaa gaaaaaaaaa aaaaaaaaa aaa | 2323 |

<210> SEQ ID NO 3
<211> LENGTH: 213
<212> TYPE: PRT
<213> ORGANISM: Homo sapiens

<400> SEQUENCE: 3

Met Gln Leu Pro Leu Ala Leu Cys Leu Val Cys Leu Leu Val His Thr
1               5                   10                  15

Ala Phe Arg Val Val Glu Gly Gln Gly Trp Gln Ala Phe Lys Asn Asp
            20                  25                  30

Ala Thr Glu Ile Ile Pro Glu Leu Gly Glu Tyr Pro Glu Pro Pro Pro
        35                  40                  45

Glu Leu Glu Asn Asn Lys Thr Met Asn Arg Ala Glu Asn Gly Gly Arg
    50                  55                  60

Pro Pro His His Pro Phe Glu Thr Lys Asp Val Ser Glu Tyr Ser Cys
65                  70                  75                  80

Arg Glu Leu His Phe Thr Arg Tyr Val Thr Asp Gly Pro Cys Arg Ser
                85                  90                  95

Ala Lys Pro Val Thr Glu Leu Val Cys Ser Gly Gln Cys Gly Pro Ala
            100                 105                 110

Arg Leu Leu Pro Asn Ala Ile Gly Arg Gly Lys Trp Trp Arg Pro Ser
        115                 120                 125

Gly Pro Asp Phe Arg Cys Ile Pro Asp Arg Tyr Arg Ala Gln Arg Val
    130                 135                 140

Gln Leu Leu Cys Pro Gly Gly Glu Ala Pro Arg Ala Arg Lys Val Arg
145                 150                 155                 160

Leu Val Ala Ser Cys Lys Cys Lys Arg Leu Thr Arg Phe His Asn Gln
                165                 170                 175

Ser Glu Leu Lys Asp Phe Gly Thr Glu Ala Ala Arg Pro Gln Lys Gly
            180                 185                 190

Arg Lys Pro Arg Pro Arg Ala Arg Ser Ala Lys Ala Asn Gln Ala Glu
        195                 200                 205

Leu Glu Asn Ala Tyr
    210

<210> SEQ ID NO 4
<211> LENGTH: 4040
<212> TYPE: DNA
<213> ORGANISM: Homo sapiens

<400> SEQUENCE: 4

| | |
|---|---|
| tgaatgccac agcttgtcag cagccagcag aaggcaggta aaaggccttc ctcactgtcc | 60 |

```
tcgaaggaac caactctgcc aatgtcttga acttgcactc ctaacctcca gctctgtgag    120
acgacttctg ttgtttatgc cacccaattt gtggtactta gttacggcag cctcatcaaa    180
gtaccaccta tgggagcctc tattttgcag gtgagggcgg ggactgggct gagttttctg    240
gaaaacagcc ctgcaatacc ctcatcagac caccaaactc ttcacactcc ctcagacaca    300
gcattcactt ccagaaataa ctctaaagtt ttgttttgtt tttttaaact tgtggaata    360 ctactcagcc aaaaaaaaaa aaaagaaaa gaaaaaggaa catgttactg atatgtacaa    420
cttggataat ggaaataatg ctgagtgaaa aaaaaatccc caaaggctac atactaattg    480
attccattta tataaccttt tttttttttt tttgagacag tctcactctg tcacccaggc    540
tggagcacag tggcgcgatc tcagctcact gcaacttccg cctcctgagt tcaagcgatt    600
ctcttgcctt agcttcccaa gtagctggga ttacaggtgc gtgccaccat gcccagctaa    660
tttttgtatt tttagtagag acagggtttc gccatgttgg ccaggctggt ctcgaactcc    720
tgacctcaag tgatctgcct gccttggctt cccaaagtgc tgggattaca tgagtgagcc    780
accgcacctg gtcgcattta tgtaacaatt ttgaagtgaa aaaaaaaatg acagaaatgg    840
agattagatg agtagttgcc aggggttagt tgtgggaggg aggaaaagg agggaaggag    900 gtgggcaaca ggagaaagac ttgtggtcac agagctgtgc tttatcttga ctgtggtgga    960
tccccaaatt tacccgtgac aagattgcat agaactaagt atacacacac gtgaatgcgt   1020
gtgcacgcac acagtagagg ttaagccacg ggagatgtgg gtaagattgg taaattgtgt   1080
caatatcaat atcctagttg tgatattgtc ctatagtttc gcaaggtgtt attgttgtgg   1140
gaaactggat aaaggataca cggagtctgc attttctttt ttttattttt attttttgag   1200
acggggtctc actctgtcaa ccaggctgga gtgcagtggc caagtatgg ctcactgcag   1260 cctcgacctc aacctcaagt gaacctccca cctcagcctc ccaagtagct aagaccacag   1320
gcgtgcgacc ccatgcccag ctaattttta aattttttgt agagactagg cctcaccatg   1380
ttgcccaggc ttttatttct tataagtata tttaaattta taattatatc cacatttaa   1440 aattttaatt taaaaatta ctctgaggcc gggcattgtg gctcatgcct ctaatcccca   1500
gcaccttggg aggccgagtt gggcagatca cccgaggtca gaagttcgag accagcctga   1560
gtaacatgga gaaaccccg tctctactaa aaatacaaaa ttggccgggc gtggtggtgc   1620
attcctgtaa tcccagctac tcgggaggct gaggcaggag aattgcttga acccaggagg   1680
tggaggttgc agtgagccaa gattgtgcca ctgcactgca gcctgggcca cagagagaat   1740
ctgccaaaaa aagaaaaaaa aaaaaatttc agccgtacaa ggatgttcat agcaaccctg   1800
ctggaaatag gaaaaaaaat tggaaataac ctaaactact cacaatagga atcagctaaa   1860
accctggggg tttaattcca gggaatactg tgaacaatga caagtttgtg gactgagtaa   1920
aaataaacag ctgtcaatga cttaacatta aatgaaacag cagaagatgt cacagcaggt   1980
tctcgctgag ccattcagag gggtgtggat catttagagg ttcaagtcca ctggattctt   2040 cttttttcctt ttaatattac ttcacttcca aataaggaaa ggaaaggaaa ggaaatcacg   2100
tccagtcctg agacttgcca tcctgcagtc accctcctt ttgtctccag caggtggcag   2160
acgcgttcca gggatgaatc ccactgcctc tgtttaatgc agacggtcca gccgctccca   2220
acagcaggtg gggctataag catccatcct acctgctcaa ggaacccagg catcagaact   2280
gctctctccc aagtccattg caagaaggca gtcgtctggt catgagaggg ttaacagtcc   2340
acattccaga gcaagggaaa aggaggctgg agggtcatag acaaggggag gtggtgcgga   2400
gggccagctt ctcacaacac taccggctct gctgggagag atagatcacc cccaacaatg   2460
```

```
gccacagctg ttttcatctg ccctgaagga aactgactta ggaagcaggt atcagagagg    2520
gcccttcctg aggggcttc tgtctggctt gtaaaactgt cagagcagct gcattcatgt    2580
gtcggatgat ggatgatgga aaggacagtc ggctgcagat ggacacagcg acttgcaagt    2640
tgaggcaggt ggcaaaggac ttgcagaggc tctgcaggtg gggcatgctg attcattgcc    2700
cagttaaaat accagaggat ctgggcagcc tcttcacagg agctgcttgt cctcaaacaa    2760
tctgtcttca atgaaagatt cctctggcct tcctttctct tcttgcacct caggtgtgaa    2820
tccttctccc ccacgcctct acctgcgccc ccgcccccg ccccggccct gtgtggctca    2880
ttatatgcag ggccaaggca gcattttctc ttagcttctt tgtgaccagt tggtcctggg    2940
atggcttcat ggaacacatc ctgtggtgtg caccaatgaa gctttccata caggactcaa    3000
aactgttttt gaaaatgta accagctgga agacaagaaa ataaaatgtc agcactaaaa    3060
acgctggctg tggcttttgc taaggaaagg aatttggtgt tgtcttctca cacacagaa    3120 ctggttgggg aaatgactgt cttcagcaca tcaccctgcg agccacagtg agtgccctgg    3180
ctcagaagtg cctgtcacag tgcacaggat ccctgaggag catgagctgg gatttcctct    3240
gtgctgtcca tcacaggagc ctgagtgacc agcgcatcct cgatttgtaa ccagaatcct    3300
gccctctctc ccaagcgggc acccttgctc tgaccctcta gttctctctc ttgccttcca    3360
gagaatacca agagaggctt tcttggttag acaatgaat gctgagactt gtggagttgg    3420
gaccaatggg atttctttaa aagcatcttt ttgcctctgg ctgggtctat gggggtcaaa    3480
cagaaacacc ttgggccatt tgttggtggg gtgacaaatg aacttggcct gagaaatgga    3540
ataggccggg ctcagccccg cgaagcactc agaactgcac attttctttg ttgagcgggt    3600
ccacagtttg ttttgagaat gcccgagggc ccagggagag agacaattaa agccggagc    3660 tcattttgat atctgaaaac cacagccgcc agcacgtggg aggtgccgga gagcaggctt    3720
gggccttgcc tcacacgccc cctctctctg ggtcacctgg gagtgccagc agcaatttgg    3780
aagtttgctg agctagagga gaagtctttg gggagggttt gctctgagca ccccctttc    3840 cctccctccg gggctgaggg aaacatggga ccagccctgc cccagcctgt cctcattggc    3900
tggcatgaag cagagagggg cttttaaaaag gcgaccgtgt ctcggctgga gaccagagcc    3960
tgtgctactg gaaggtggcg tgccctcctc tggctggtac catgcagctc ccactggccc    4020
tgtgtctcgt ctgcctgctg                                                4040
```

<210> SEQ ID NO 5
<211> LENGTH: 636
<212> TYPE: DNA
<213> ORGANISM: Mus musculus

<400> SEQUENCE: 5

```
atgcagccct cactagcccc gtgcctcatc tgcctacttg tgcacgctgc cttctgtgct     60
gtggagggcc aggggtggca agccttcagg aatgatgcca cagaggtcat cccagggctt    120
ggagagtacc ccgagcctcc tcctgagaac aaccagacca tgaaccgggc ggagaatgga    180
ggcagacctc cccaccatcc ctatgacgcc aaagatgtgt ccgagtacag ctgccgcgag    240
ctgcactaca cccgcttcct gacagacggc ccatgccgca gcgccaagcc ggtcaccgag    300
ttggtgtgct ccggccagtg cggccccgcg cggctgctgc caacgccat cgggcgcgtg    360 aagtggtggc gcccgaacgg accggatttc cgctgcatcc cggatcgcta ccgcgcgcag    420
cgggtgcagc tgctgtgccc cggggcgcg gcgccgcgct cgcgcaaggt gcgtctggtg    480
gcctcgtgca gtgcaagcg cctcacccgc ttccacaacc agtcggagct caaggacttc    540
```

```
gggccggaga ccgcgcggcc gcagaagggt cgcaagccgc ggcccggcgc cggggagcc      600 aaagccaacc aggcggagct ggagaacgcc tactag                              636
```

<210> SEQ ID NO 6
<211> LENGTH: 211
<212> TYPE: PRT
<213> ORGANISM: Mus musculus

<400> SEQUENCE: 6

```
Met Gln Pro Ser Leu Ala Pro Cys Leu Ile Cys Leu Val His Ala
1               5                   10                  15

Ala Phe Cys Ala Val Glu Gly Gln Gly Trp Gln Ala Phe Arg Asn Asp
                20                  25                  30

Ala Thr Glu Val Ile Pro Gly Leu Gly Glu Tyr Pro Glu Pro Pro
            35                  40                  45

Glu Asn Asn Gln Thr Met Asn Arg Ala Glu Asn Gly Gly Arg Pro Pro
 50                  55                  60

His His Pro Tyr Asp Ala Lys Asp Val Ser Glu Tyr Ser Cys Arg Glu
 65                  70                  75                  80

Leu His Tyr Thr Arg Phe Leu Thr Asp Gly Pro Cys Arg Ser Ala Lys
                85                  90                  95

Pro Val Thr Glu Leu Val Cys Ser Gly Gln Cys Gly Pro Ala Arg Leu
            100                 105                 110

Leu Pro Asn Ala Ile Gly Arg Val Lys Trp Trp Arg Pro Asn Gly Pro
        115                 120                 125

Asp Phe Arg Cys Ile Pro Asp Arg Tyr Arg Ala Gln Arg Val Gln Leu
    130                 135                 140

Leu Cys Pro Gly Gly Ala Ala Pro Arg Ser Arg Lys Val Arg Leu Val
145                 150                 155                 160

Ala Ser Cys Lys Cys Lys Arg Leu Thr Arg Phe His Asn Gln Ser Glu
                165                 170                 175

Leu Lys Asp Phe Gly Pro Glu Thr Ala Arg Pro Gln Lys Gly Arg Lys
            180                 185                 190

Pro Arg Pro Gly Ala Arg Gly Ala Lys Ala Asn Gln Ala Glu Leu Glu
        195                 200                 205

Asn Ala Tyr
    210
```

<210> SEQ ID NO 7
<211> LENGTH: 674
<212> TYPE: DNA
<213> ORGANISM: Rattus norvegicus

<400> SEQUENCE: 7

```
gaggaccgag tgcccttcct ccttctggca ccatgcagct ctcactagcc ccttgccttg      60
cctgcctgct tgtacatgca gccttcgttg ctgtggagag ccaggggtgg caagccttca     120
agaatgatgc cacagaaatc atcccgggac tcagagagta cccagagcct cctcaggaac     180
tagagaacaa ccagaccatg aaccggccg agaacgagg cagaccccccc caccatcctt     240 atgacaccaa agacgtgtcc gagtacagct gccgcgagct gcactacacc cgcttcgtga     300
ccgacggccc gtgccgcagt gccaagccgg tcaccgagtt ggtgtgctcg ggccagtgcg     360
gccccgcgcg gctgctgccc aacgccatcg gcgcgtgaa gtggtggcgc ccgaacggac     420
ccgacttccg ctgcatcccg gatcgctacc gcgcgcagcg ggtgcagctg ctgtgccccg     480
gcggcgcggc gccgcgctcg cgcaaggtgc gtctggtggc ctcgtgcaag tgcaagcgcc     540
```

```
tcacccgctt ccacaaccag tcggagctca aggacttcgg acctgagacc gcgcggccgc      600
agaagggtcg caagccgcgg ccccgcgccc ggggagccaa agccaaccag gcggagctgg      660
agaacgccta ctag                                                        674
```

<210> SEQ ID NO 8
<211> LENGTH: 213
<212> TYPE: PRT
<213> ORGANISM: Rattus norvegicus

<400> SEQUENCE: 8

```
Met Gln Leu Ser Leu Ala Pro Cys Leu Ala Cys Leu Leu Val His Ala
1               5                   10                  15

Ala Phe Val Ala Val Glu Ser Gln Gly Trp Gln Ala Phe Lys Asn Asp
            20                  25                  30

Ala Thr Glu Ile Ile Pro Gly Leu Arg Glu Tyr Pro Glu Pro Pro Gln
        35                  40                  45

Glu Leu Glu Asn Asn Gln Thr Met Asn Arg Ala Glu Asn Gly Gly Arg
    50                  55                  60

Pro Pro His His Pro Tyr Asp Thr Lys Asp Val Ser Glu Tyr Ser Cys
65                  70                  75                  80

Arg Glu Leu His Tyr Thr Arg Phe Val Thr Asp Gly Pro Cys Arg Ser
                85                  90                  95

Ala Lys Pro Val Thr Glu Leu Val Cys Ser Gly Gln Cys Gly Pro Ala
            100                 105                 110

Arg Leu Leu Pro Asn Ala Ile Gly Arg Val Lys Trp Trp Arg Pro Asn
        115                 120                 125

Gly Pro Asp Phe Arg Cys Ile Pro Asp Arg Tyr Arg Ala Gln Arg Val
    130                 135                 140

Gln Leu Leu Cys Pro Gly Gly Ala Ala Pro Arg Ser Arg Lys Val Arg
145                 150                 155                 160

Leu Val Ala Ser Cys Lys Cys Lys Arg Leu Thr Arg Phe His Asn Gln
                165                 170                 175

Ser Glu Leu Lys Asp Phe Gly Pro Glu Thr Ala Arg Pro Gln Lys Gly
            180                 185                 190

Arg Lys Pro Arg Pro Arg Ala Arg Gly Ala Lys Ala Asn Gln Ala Glu
        195                 200                 205

Leu Glu Asn Ala Tyr
    210
```

<210> SEQ ID NO 9
<211> LENGTH: 21
<212> TYPE: DNA
<213> ORGANISM: Homo sapiens

<400> SEQUENCE: 9

```
aagaatgatg ccacggaaat c                                                21
```

<210> SEQ ID NO 10
<211> LENGTH: 21
<212> TYPE: RNA
<213> ORGANISM: Artificial sequence
<220> FEATURE:
<223> OTHER INFORMATION: Small Interfering RNA to Block Expression of
      SOST (sense strand)
<220> FEATURE:
<221> NAME/KEY: misc_feature
<222> LOCATION: (20)..(21)
<223> OTHER INFORMATION: n is t

```
<400> SEQUENCE: 10
gaaugaugcc acggaaaucn n                                              21

<210> SEQ ID NO 11
<211> LENGTH: 21
<212> TYPE: RNA
<213> ORGANISM: Artificial sequence
<220> FEATURE:
<223> OTHER INFORMATION: Small Interfering RNA to Block Expression of
      SOST (sense strand)
<220> FEATURE:
<221> NAME/KEY: misc_feature
<222> LOCATION: (20)..(21)
<223> OTHER INFORMATION: n is t

<400> SEQUENCE: 11 gauuccgug gcaucauucn n                                               21

<210> SEQ ID NO 12
<211> LENGTH: 21
<212> TYPE: DNA
<213> ORGANISM: Homo sapiens

<400> SEQUENCE: 12
aatgatgcca cggaaatcat c                                              21

<210> SEQ ID NO 13
<211> LENGTH: 21
<212> TYPE: RNA
<213> ORGANISM: Artificial sequence
<220> FEATURE:
<223> OTHER INFORMATION: Small Interfering RNA to Block Expression of
      SOST (sense strand)
<220> FEATURE:
<221> NAME/KEY: misc_feature
<222> LOCATION: (20)..(21)
<223> OTHER INFORMATION: n is t

<400> SEQUENCE: 13
ugaugccacg gaaaucaucn n                                              21

<210> SEQ ID NO 14
<211> LENGTH: 21
<212> TYPE: RNA
<213> ORGANISM: Artificial sequence
<220> FEATURE:
<223> OTHER INFORMATION: Small Interfering RNA to Block Expression of
      SOST (sense strand)
<220> FEATURE:
<221> NAME/KEY: misc_feature
<222> LOCATION: (20)..(21)
<223> OTHER INFORMATION: n is t

<400> SEQUENCE: 14
gaugauuucc guggcaucan n                                              21

<210> SEQ ID NO 15
<211> LENGTH: 21
<212> TYPE: DNA
<213> ORGANISM: Homo sapiens

<400> SEQUENCE: 15
aacaacaaga ccatgaaccg g                                              21

<210> SEQ ID NO 16
<211> LENGTH: 21
<212> TYPE: RNA
<213> ORGANISM: Artificial sequence
```

```
<220> FEATURE:
<223> OTHER INFORMATION: Small Interfering RNA to Block Expression of
      SOST (sense strand)
<220> FEATURE:
<221> NAME/KEY: misc_feature
<222> LOCATION: (20)..(21)
<223> OTHER INFORMATION: n is t

<400> SEQUENCE: 16
caacaagacc augaaccggn n                                              21

<210> SEQ ID NO 17
<211> LENGTH: 21
<212> TYPE: RNA
<213> ORGANISM: Artificial sequence
<220> FEATURE:
<223> OTHER INFORMATION: Small Interfering RNA to Block Expression of
      SOST (sense strand)
<220> FEATURE:
<221> NAME/KEY: misc_feature
<222> LOCATION: (20)..(21)
<223> OTHER INFORMATION: n is t

<400> SEQUENCE: 17
ccgguucaug gucuuguugn n                                              21

<210> SEQ ID NO 18
<211> LENGTH: 21
<212> TYPE: DNA
<213> ORGANISM: Homo sapiens

<400> SEQUENCE: 18
aattgagagt cacagacact g                                              21

<210> SEQ ID NO 19
<211> LENGTH: 21
<212> TYPE: RNA
<213> ORGANISM: Artificial sequence
<220> FEATURE:
<223> OTHER INFORMATION: Small Interfering RNA to Block Expression of
      SOST (sense strand)
<220> FEATURE:
<221> NAME/KEY: misc_feature
<222> LOCATION: (20)..(21)
<223> OTHER INFORMATION: n is t

<400> SEQUENCE: 19
uugagaguca cagacacugn n                                              21

<210> SEQ ID NO 20
<211> LENGTH: 21
<212> TYPE: RNA
<213> ORGANISM: Artificial sequence
<220> FEATURE:
<223> OTHER INFORMATION: Small Interfering RNA to Block Expression of
      SOST (sense strand)
<220> FEATURE:
<221> NAME/KEY: misc_feature
<222> LOCATION: (20)..(21)
<223> OTHER INFORMATION: n is t

<400> SEQUENCE: 20
cagugucugu gacucucaan n                                              21

<210> SEQ ID NO 21
<211> LENGTH: 21
<212> TYPE: DNA
<213> ORGANISM: Homo sapiens

<400> SEQUENCE: 21
```
aaatggaagc attttcaccg c                                              21

<210> SEQ ID NO 22
<211> LENGTH: 21
<212> TYPE: RNA
<213> ORGANISM: Artificial sequence
<220> FEATURE:
<223> OTHER INFORMATION: Small Interfering RNA to Block Expression of
      SOST (sense strand)
<220> FEATURE:
<221> NAME/KEY: misc_feature
<222> LOCATION: (20)..(21)
<223> OTHER INFORMATION: n is t

<400> SEQUENCE: 22
auggaagcau uuucaccgcn n                                              21

<210> SEQ ID NO 23
<211> LENGTH: 21
<212> TYPE: RNA
<213> ORGANISM: Artificial sequence
<220> FEATURE:
<223> OTHER INFORMATION: Small Interfering RNA to Block Expression of
      SOST (sense strand)
<220> FEATURE:
<221> NAME/KEY: misc_feature
<222> LOCATION: (20)..(21)
<223> OTHER INFORMATION: n is t

<400> SEQUENCE: 23
gcggugaaaa ugcuuccaun n                                              21

<210> SEQ ID NO 24
<211> LENGTH: 21
<212> TYPE: DNA
<213> ORGANISM: Homo sapiens

<400> SEQUENCE: 24
aaagtccagg gactggttaa g                                              21

<210> SEQ ID NO 25
<211> LENGTH: 21
<212> TYPE: RNA
<213> ORGANISM: Artificial sequence
<220> FEATURE:
<223> OTHER INFORMATION: Small Interfering RNA to Block Expression of
      SOST (sense strand)
<220> FEATURE:
<221> NAME/KEY: misc_feature
<222> LOCATION: (20)..(21)
<223> OTHER INFORMATION: n is t

<400> SEQUENCE: 25
aguccaggga cugguuaagn n                                              21

<210> SEQ ID NO 26
<211> LENGTH: 21
<212> TYPE: RNA
<213> ORGANISM: Artificial sequence
<220> FEATURE:
<223> OTHER INFORMATION: Small Interfering RNA to Block Expression of
      SOST (sense strand)
<220> FEATURE:
<221> NAME/KEY: misc_feature
<222> LOCATION: (20)..(21)
<223> OTHER INFORMATION: n is t

<400> SEQUENCE: 26
cuuaaccagu cccuggacun n                                              21

```
<210> SEQ ID NO 27
<211> LENGTH: 21
<212> TYPE: DNA
<213> ORGANISM: Homo sapiens

<400> SEQUENCE: 27
aagaaagttg gataagattc c                                              21

<210> SEQ ID NO 28
<211> LENGTH: 21
<212> TYPE: RNA
<213> ORGANISM: Artificial sequence
<220> FEATURE:
<223> OTHER INFORMATION: Small Interfering RNA to Block Expression of
      SOST (sense strand)
<220> FEATURE:
<221> NAME/KEY: misc_feature
<222> LOCATION: (20)..(21)
<223> OTHER INFORMATION: n is t

<400> SEQUENCE: 28
gaaaguugga uaagauuccn n                                              21

<210> SEQ ID NO 29
<211> LENGTH: 21
<212> TYPE: RNA
<213> ORGANISM: Artificial sequence
<220> FEATURE:
<223> OTHER INFORMATION: Small Interfering RNA to Block Expression of
      SOST (sense strand)
<220> FEATURE:
<221> NAME/KEY: misc_feature
<222> LOCATION: (20)..(21)
<223> OTHER INFORMATION: n is t

<400> SEQUENCE: 29
ggaaucuuau ccaacuuucn n                                              21

<210> SEQ ID NO 30
<211> LENGTH: 21
<212> TYPE: DNA
<213> ORGANISM: Homo sapiens

<400> SEQUENCE: 30
aactgtagat gtggtttcta g                                              21

<210> SEQ ID NO 31
<211> LENGTH: 21
<212> TYPE: RNA
<213> ORGANISM: Artificial sequence
<220> FEATURE:
<223> OTHER INFORMATION: Small Interfering RNA to Block Expression of
      SOST (sense strand)
<220> FEATURE:
<221> NAME/KEY: misc_feature
<222> LOCATION: (20)..(21)
<223> OTHER INFORMATION: n is t

<400> SEQUENCE: 31
cuguagaugu gguuucuagn n                                              21

<210> SEQ ID NO 32
<211> LENGTH: 21
<212> TYPE: RNA
<213> ORGANISM: Artificial sequence
<220> FEATURE:
<223> OTHER INFORMATION: Small Interfering RNA to Block Expression of
      SOST (sense strand)
```

```
<220> FEATURE:
<221> NAME/KEY: misc_feature
<222> LOCATION: (20)..(21)
<223> OTHER INFORMATION: n is t

<400> SEQUENCE: 32
cuagaaacca caucuacagn n                                                    21

<210> SEQ ID NO 33
<211> LENGTH: 21
<212> TYPE: DNA
<213> ORGANISM: Homo sapiens

<400> SEQUENCE: 33
aattctcctt cgggacctca a                                                    21

<210> SEQ ID NO 34
<211> LENGTH: 21
<212> TYPE: RNA
<213> ORGANISM: Artificial sequence
<220> FEATURE:
<223> OTHER INFORMATION: Small Interfering RNA to Block Expression of
      SOST (sense strand)
<220> FEATURE:
<221> NAME/KEY: misc_feature
<222> LOCATION: (20)..(21)
<223> OTHER INFORMATION: n is t

<400> SEQUENCE: 34
uucuccuucg ggaccucaan n                                                    21

<210> SEQ ID NO 35
<211> LENGTH: 21
<212> TYPE: RNA
<213> ORGANISM: Artificial sequence
<220> FEATURE:
<223> OTHER INFORMATION: Small Interfering RNA to Block Expression of
      SOST (sense strand)
<220> FEATURE:
<221> NAME/KEY: misc_feature
<222> LOCATION: (20)..(21)
<223> OTHER INFORMATION: n is t

<400> SEQUENCE: 35
uugagguccc gaaggagaan n                                                    21

<210> SEQ ID NO 36
<211> LENGTH: 21
<212> TYPE: DNA
<213> ORGANISM: Homo sapiens

<400> SEQUENCE: 36
aaagagagag aatgaatgca g                                                    21

<210> SEQ ID NO 37
<211> LENGTH: 21
<212> TYPE: RNA
<213> ORGANISM: Artificial sequence
<220> FEATURE:
<223> OTHER INFORMATION: Small Interfering RNA to Block Expression of
      SOST (sense strand)
<220> FEATURE:
<221> NAME/KEY: misc_feature
<222> LOCATION: (20)..(21)
<223> OTHER INFORMATION: n is t

<400> SEQUENCE: 37
agagagagaa ugaaugcagn n                                                    21
```

```
<210> SEQ ID NO 38
<211> LENGTH: 21
<212> TYPE: RNA
<213> ORGANISM: Artificial sequence
<220> FEATURE:
<223> OTHER INFORMATION: Small Interfering RNA to Block Expression of
      SOST (sense strand)
<220> FEATURE:
<221> NAME/KEY: misc_feature
<222> LOCATION: (20)..(21)
<223> OTHER INFORMATION: n is t

<400> SEQUENCE: 38
cugcauucau ucucucucun n                                             21

<210> SEQ ID NO 39
<211> LENGTH: 21
<212> TYPE: DNA
<213> ORGANISM: Homo sapiens

<400> SEQUENCE: 39
aagaagctat gctgcttccc a                                             21

<210> SEQ ID NO 40
<211> LENGTH: 21
<212> TYPE: RNA
<213> ORGANISM: Artificial sequence
<220> FEATURE:
<223> OTHER INFORMATION: Small Interfering RNA to Block Expression of
      SOST (sense strand)
<220> FEATURE:
<221> NAME/KEY: misc_feature
<222> LOCATION: (20)..(21)
<223> OTHER INFORMATION: n is t

<400> SEQUENCE: 40
gaagcuaugc ugcuucccan n                                             21

<210> SEQ ID NO 41
<211> LENGTH: 18
<212> TYPE: RNA
<213> ORGANISM: Artificial sequence
<220> FEATURE:
<223> OTHER INFORMATION: Small Interfering RNA to Block Expression of
      SOST (sense strand)

<400> SEQUENCE: 41
ugggaagcag cauagcuu                                                 18

<210> SEQ ID NO 42
<211> LENGTH: 21
<212> TYPE: DNA
<213> ORGANISM: Homo sapiens

<400> SEQUENCE: 42
aaatcacatc cgccccaact t                                             21

<210> SEQ ID NO 43
<211> LENGTH: 21
<212> TYPE: RNA
<213> ORGANISM: Artificial sequence
<220> FEATURE:
<223> OTHER INFORMATION: Small Interfering RNA to Block Expression of
      SOST (sense strand)
<220> FEATURE:
<221> NAME/KEY: misc_feature
<222> LOCATION: (20)..(21)
<223> OTHER INFORMATION: n is t
```

```
-continued

<400> SEQUENCE: 43
aucacauccg ccccaacuun n                                              21

<210> SEQ ID NO 44
<211> LENGTH: 21
<212> TYPE: RNA
<213> ORGANISM: Artificial sequence
<220> FEATURE:
<223> OTHER INFORMATION: Small Interfering RNA to Block Expression of
      SOST (sense strand)
<220> FEATURE:
<221> NAME/KEY: misc_feature
<222> LOCATION: (20)..(21)
<223> OTHER INFORMATION: n is t

<400> SEQUENCE: 44
aaguuggggc ggaugugaun n                                              21
```

METHODS TO INCREASE OR DECREASE BONE DENSITY

This application is a continuation of U.S. patent application Ser. No. 11/960,509 filed on Dec. 19, 2007, now U.S. Pat. No. 7,655,420, which is a divisional of U.S. patent application Ser. No. 10/377,315, filed Feb. 28, 2003, now U.S. Pat. No. 7,332,276, which claims priority from U.S. Application Ser. No. 60/361,258 filed Mar. 1, 2002, from U.S. Application Ser. No. 60/406,171 filed Aug. 27, 3002 and from U.S. Application Ser. No. 60/447,393 filed Feb. 13, 2003.

FIELD OF THE INVENTION

The invention provides compositions and methods for modulating bone density. Methods for identifying new compounds that can modulate bone density are also provided.

BACKGROUND OF THE INVENTION

Osteoporosis is a bone disorder characterized by the loss of bone mass, which leads to fragility and porosity of the bone of man. As a result, patients suffering from osteoporosis have an increased fracture risk of the bones. Postmenopausal women are particularly at risk for osteoporosis as a result of reduced levels of estrogen production. When administered at low levels, estrogens have a beneficial effect on the loss of bone. However, estrogen replacement therapy can have unwanted side effects including an increased risk of blood clots, breast carcinomas, endometrium hyperplasia, and an increased risk of endometrium carcinomas. The remaining current therapies provide little in terms of generating new bone for osteoporotic patients. Hence, a need exists for an alternative treatment of osteoporosis.

Sclerosteosis is a genetic disease resulting in increased bone formation and the development of strong skeletons in humans. Sclerosteosis is caused by a loss of function or null mutation in the SOST gene (Beighton et al. 1976; Brunkow et al. 2001; Balesman et al. 2001). The majority of affected individuals have been reported in the Afrikaner population of South Africa, where a high incidence of the disorder occurs as a result of a founder effect. Homozygosity mapping in Afrikaner families along with analysis of historical recombinants localized sclerosteosis to an interval of approximately 2 cM between the loci D17S1787 and D17S930 on chromosome 17q12-q21. Affected Afrikaners carry a nonsense mutation near the amino terminus of the encoded protein, whereas an unrelated affected person of Senegalese origin carries two splicing mutations within the single intron of the gene.

The SOST gene encodes a protein called sclerostin that shares some sequence similarity with a class of cystine knot-containing factors including dan, cerberus, gremlin, prdc, and caronte. The sclerostin protein gene is thought to interact with one or more of the bone morphogenetic proteins (BMPs) (Brunkow et al, 2001). Bone morphogenetic proteins are members of the transforming growth factor (TGF-β) superfamily that have been shown to play a role in influencing cell proliferation, differentiation and apoptosis of many tissue types including bone. Bone morphogenetic proteins can induce de novo cartilage and bone formation, and appear to be essential for skeletal development during mammalian embryogenesis (Wang 1993). Early in the process of fracture healing the concentration of bone morphogenetic protein-4 (BMP-4) increases dramatically (Nakase et al. 1994 and Bostrom et al. 1995). In vivo experiments indicate that up-regulation of BMP-4 transcription may promote bone healing in mammals (Fang et al. 1996). Bone morphogenetic proteins have been reported to induce the differentiation of cells of the mesenchymal lineage to osteogenic cells as well as to enhance the expression of osteoblastic phenotypic markers in committed cells (Gazzero et al. 1998, Nifuji & Noda, 1999). The activities of bone morphogenetic proteins in osteoblastic cells appear to be modulated by proteins such as noggin and gremlin that function as bone morphogenetic protein antagonists by binding and inactivating bone morphogenetic proteins (Yamaguchi et al. 2000).

However, the cascade of events leading to bone mineralization and the factors that control bone density are not completely understood. A need exists for factors that can modulate the differentiation of osteoblastic cells, promote bone mineralization and improve bone density.

SUMMARY OF HE INVENTION

According to the invention, the sclerostin protein encoded by the SOST gene is a unique bone morphogenetic protein antagonist and an important regulator of bone matrix formation. The SOST gene is expressed at high levels by committed, mature osteoblasts but at low or non-existent levels in immature and undifferentiated osteoblasts. Also according to the invention, the sclerostin protein blocks the ability of osteoprogenitor cells to differentiate, to deposit mineral and to express proteins characteristic of fully mature osteoblasts, for example, collagen and alkaline phosphatase. The expression of SOST is modulated by steroids and is regulated by bone morphogenetic proteins, for example, bone morphogenetic factors 2, 4 and 6. While bone morphogenetic factors increase the activity of osteoblastic markers such as alkaline phosphatase, the SOST gene product (sclerostin) blocks the activity of such osteoblastic markers. Moreover, bone morphogenetic factors can reverse the sclerostin-induced decrease in osteoblastic activity.

The invention provides pharmaceutical compositions for decreasing SOST expression in a mammal comprising a therapeutically effective amount of a compound of the formula 1:

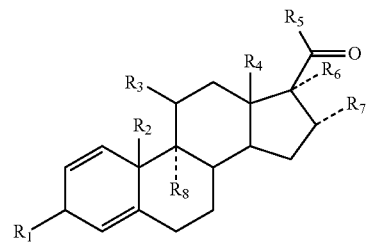

wherein $R_1$, $R_3$, $R_4$, $R_5$, $R_6$, $R_7$, and $R_8$ are separately carbonyl, halo, fluorine, hydrogen, hydroxyl, lower acyl, lower alkoxy, lower alkyl, or lower hydroxy alkyl. In some embodiments, the $R_1$, $R_2$, $R_3$, $R_4$, $R_5$, $R_6$, $R_7$, and $R_8$ groups can separately be carbonyl, hydroxy, hydrogen, or lower hydroxy alkyl. In other embodiments, $R_1$ is carbonyl or hydroxy and/or $R_8$ is fluorine, hydrogen or halo.

The invention further provides a pharmaceutical composition for decreasing SOST expression in a mammal comprising a therapeutically effective amount of a glucocorticoid. The glucocorticoid can be, for example, fluocinolone acetonide, triamcinolone or dexamethasone.

The invention also provides a pharmaceutical composition for decreasing SOST expression in a mammal comprising a therapeutically effective amount of a prostaglandin comprising formula II:

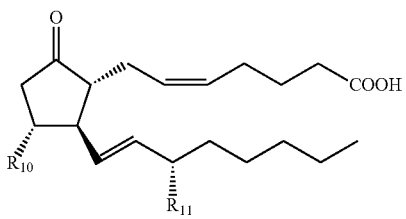

wherein $R_{10}$ and $R_{11}$ are separately carbonyl, halo, fluorine, hydrogen, hydroxyl, lower acyl, lower alkoxy, lower alkyl, lower hydroxy alkyl, aryl or aryloxy. $R_{10}$ and $R_{11}$ can also separately be carbonyl, hydroxy, hydrogen, or lower hydroxy alkyl. The prostaglandin can be, for example, prostaglandin E2.

The invention also provides a pharmaceutical composition for decreasing SOST expression in a mammal comprising a therapeutically effective amount of a bile salt of formula III:

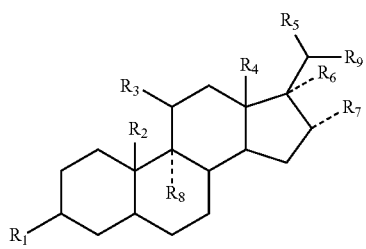

wherein $R_1$, $R_2$, $R_3$, $R_4$, $R_5$, $R_6$, $R_7$, $R_8$ and $R_9$ are separately carbonyl, halo, fluorine, hydrogen, hydroxyl, lower acyl, lower alkoxy, lower alkyl, or lower hydroxy alkyl. $R_1$, $R_2$, $R_3$, $R_4$, $R_5$, $R_6$, $R_7$ and $R_9$ can also separately be carbonyl, hydroxy, hydrogen, or lower hydroxy alkyl. An example of such a bile salt is ursodeoxycholic acid.

The invention also provides a pharmaceutical composition for decreasing SOST expression in a mammal comprising a therapeutically effective amount of a prostaglandin such as prostaglandin E2, a bile salt such as ursodeoxycholic acid, or a glucocorticoid such as fluocinolone acetonide, triamcinolone or dexamethasone.

The invention further provides a method for decreasing SOST expression in a mammal that comprises administering to the mammal a therapeutically effective amount of a prostaglandin such as prostaglandin E2, a bile salt such as ursodeoxycholic acid, or a glucocorticoid such as fluocinolone acetonide, triamcinolone or dexamethasone.

The invention also provides a method for increasing bone density in a mammal that comprises administering a therapeutically effective amount of ursodeoxycholic acid, fluocinolone acetonide, triamcinolone, prostaglandin E2 or dexamethasone to the mammal. In one embodiment, the methods of the invention can be practiced with a steroid or a glucocorticoid hormone. Examples of such glucocorticoid hormones include cortisol, dexamethasone and structurally related compounds. An example of a therapeutically effective amount of a glucocorticoid hormone is a blood concentration of about 0.01 micromolar to about 1 micromolar.

The invention further provides a pharmaceutical composition for decreasing SOST expression in a mammal comprising a therapeutically effective amount of an anti-sense nucleic acid capable of hybridizing to SEQ ID NO:1, 2, 4, 5 or 7.

The invention also provides a pharmaceutical composition that comprises a therapeutically effective amount of a sclerostin antagonist. Such a sclerostin antagonist can be an antibody that can bind a sclerostin polypeptide having SEQ ID NO:3 or SEQ ID NO:6 or SEQ ID NO:8. Another example of such a sclerostin antagonist is a peptide of a bone morphogenetic protein that binds to sclerostin.

The invention further provides a method for identifying a factor that decreases SOST expression comprising: providing a cell that comprises a nucleic acid construct comprising a SOST promoter having SEQ ID NO:4 that is operably linked to a nucleic acid encoding a detectable marker; contacting the cell with a test sample containing a factor; and detecting whether a factor in the test sample decreases expression of the detectable marker relative to a control that comprises the cell that has not been contacted with a test sample. For example, such a cell line is any cell line responsive to a bone morphogenetic protein. Another example of such a cell is a C2C12 cell line having ATCC Deposit No. CRL-1772 or a C3H10T1/2 cell line having ATCC Deposit No. CCL-226 or a human mesenchymal (hMSC) cell. Another element that can be present in the nucleic acid construct is an osteoblastic-specific steroid response element.

The invention also provides a method for identifying a factor that decreases SOST expression comprising contacting a cell with a test sample and detecting whether a factor in the test sample decreases endogenous SOST expression. In this method, SOST expression can be from a nucleic acid comprising SEQ ID NO:1 or SEQ ID NO:2 or SEQ ID NO:5 or SEQ ID NO:7. In another embodiment of this method, SOST expression can be from a nucleic acid encoding a protein comprising ID NO:3 or SEQ ID NO:6 or SEQ ID NO:8.

The invention further provides a method for identifying an antagonist for sclerostin comprising contacting a cell with both sclerostin and a test sample and detecting whether the test sample prevents apoptosis of the cell.

The invention also provides a method for identifying a molecule that binds to sclerostin comprising contacting a test sample with a sclerostin polypeptide comprising SEQ ID NO:3 or SEQ ID NO:6 or SEQ ID NO:8 and determining whether a molecule in the test sample binds to the polypeptide.

DESCRIPTION OF THE FIGURES

The twenty-seven figures of the application illustrate the results of experiments that define the importance of SOST and its gene product, sclerostin, in the regulation of bone homeostasis. In general, FIGS. 1 to 9 show that SOST is expressed by mature osteoblastic cells and that its expression is modulated by important bone growth factors and steroids.

FIG. 2 illustrates that SOST expression is up-regulated by bone morphogenetic proteins (BMPs). RNA was isolated for RT-PCR analysis of SOST expression from hMSC cells treated with various factors, including insulin-like growth factor-1 (IGF-1, 10 or 50 ng/ml), 1,25-dihydroxyvitamin $D_3$ (vit D, $10^{-7}$M), dexamethasone (DEX, $10^{-7}$M), BMP-6 (300 ng/ml), or BMP-4 (50 or 300 ng/ml), for 72 hrs. RNA was also isolated for RT-PCR analysis of SOST expression from cells grown for 7 or 21 days in regular growth media (Control) or Osteoblast-Inducing media (Induced). As illustrated, while untreated hMSC cells ("vehicle") strongly expressed type I collagen, such cells had negligible levels of PTHr and SOST (Vehicle and Control, 21 days). These results indicate that untreated hMSC cells are in an early stage of osteoblast lineage, but are committed to osteoblastogenesis. Treatment of these cells with DEX, BMPs, IGF-1 (IGF-I at 50 ng/ml) or long-term culture in osteoblast-inducing media (Induced, 21 days) advanced the stage of differentiation and induced PTHr expression. Several factors enhanced the expression of SOST, including BMP-4, BMP-6, and IGF-1 (50 ng/ml).

FIG. 3 illustrates that bone morphogenetic proteins up-regulate SOST expression and also provides a time course of such BMP-induced SOST expression in hMSC and primary human osteoblasts. Cells were treated with BMP-2 (100 ng/ml) or BMP-4 (50 ng/ml) for 24 to 120 hrs prior to harvesting for RNA and RT-PCR analyses. As shown, maximum levels of SOST expression were achieved within 72 to 120 hrs after the start of treatment.

FIG. 4 illustrates the effects of bone morphogenetic proteins 2, 4 and 6 on the expression of BMP antagonists gremlin, noggin, and SOST in hMSC cells. hMSC cells were treated with BMPs 2, 4 and 6 (100 ng/ml) for 72 hrs prior to harvesting RNA and performing RT-PCR analyses. Two cDNA controls were run for the noggin analysis. While the basal levels of SOST and noggin were negligible in undifferentiated hMSC cells, the expression of SOST and noggin was up-regulated by BMPs-2, 4 and 6. In contrast, gremlin was constitutively expressed in undifferentiated hMSC cells and its expression was only modestly increased by the bone morphogenetic proteins.

FIG. 5 illustrates that steroids can modulate the effect of bone morphogenetic protein-4 on SOST expression. RNA was isolated from hMSC cells treated for 72 hrs with 1,25-dihydroxyvitamin $D_3$ (vit D, $10^{-7}$M), retinoic acid (RA, $10^{-6}$M), BMP-4 (250 ng/ml), dexamethasone (DEX, $10^{-7}$M), or a combination of BMP-4 with these steroids. The isolated RNA was then analyzed for SOST by RT-PCR. BMP-4 alone enhanced SOST expression. Retinoic acid and vitamin D enhanced the levels of SOST when added in combination with BMP-4—the levels of SOST were greater when retinoic acid or vitamin D was present with BMP-4 than when in cells were treated with BMP-4 alone. Dexamethasone abolished the stimulatory effect of BMP-4 on SOST expression.

FIG. 6 provides a comparison of the effects of steroids on the expression of gremlin, noggin, and SOST in hMSC cells. hMSC cells were treated for 72 hrs with BMP-4 (100 ng/ml), retinoic acid (RA, $10^{-6}$M), dexamethasone (DEX, $10^{-7}$M), and 1,25-dihydroxyvitamin $D_3$ (vit D, $10^{-7}$M) or a combination of BMP-4 with retinoic acid, dexamethasone or vitamin D. RNA was then harvested from the cells and RT-PCR analyses were performed. BMP-4 enhanced the expression of gremlin and noggin. The steroids had small effects on BMP-induced noggin and gremlin expression. As illustrated, BMP-4 also significantly increased the levels of SOST expression. This effect on SOST expression was enhanced by the presence of vitamin D or retinoic acid but was depressed by the presence of dexamethasone.

FIG. 7 provides a photograph of a gel illustrating the effects of glucocorticoid analogs and a bile salt on the expression of SOST in hMSC cells. hMSC cells were treated with BMP-6 (250 ng/ml) in the absence or presence of dexamethasone (DEX, at $10^{-7}$M), triamcinolone (Triam, at $10^{-7}$M), ursodeoxycholic acid (Urso-1 at $1\times10^{-6}$M or Urso-2 at $3\times10^{-6}$M) for 72 hrs. RNA was isolated and analyzed by RT-PCR for SOST. The DAD gene was used as a control for DNA loading. Dexamethasone, triamcinolone, ursodeoxycholic acid blocked the induction of SOST by BMP-6.

FIG. 8 provides a photograph of a gel illustrating the effects of glucocorticoid analogs and a prostaglandin on the expression of SOST in hMSC cells. hMSC cells were treated with BMP-6 (250 ng/ml) in the absence or presence of dexamethasone (DEX at $10^{-7}$M), tauroursodeoxycholic acid (Tauro at $2\times10^{-6}$ M), fluocinolone (Fluo at $10^{-7}$M), lovastatin (Lova at $10^{-7}$M), ICI 182,780 (ICI at $10^{-6}$M), 17β-estradiol (Estrogen at $10^{-6}$M) and prostaglandin E2 (PGE2 at $10^{-6}$M) for 72 hrs. RNA was isolated and analyzed by RT-PCR for SOST. The DAD gene was used as a control for DNA loading. DEX, Fluo and PGE2 blocked the induction of SOST by BMP-6.

FIG. 9A provides chemical structure of glucocorticoid, dexamethasone, that blocks BMP-induced SOST expression.

FIG. 9B provides chemical stricture of a glucocorticoid, triamcinolone, that blocks BMP-induced SOST expression.

FIG. 9C provides chemical structure of a glucocorticoid, fluocinolone acetonide, that blocks BMP-induced SOST expression.

FIG. 9D provides chemical structure of a bile salt, ursodeoxycholic acid, that blocks BMP-induced SOST expression.

FIG. 9E provides chemical structure of an eicosanoid, prostaglandin E2, that blocks BMP-induced SOST expression.

FIG. 10 provides a comparison of the effects of human sclerostin and mouse noggin proteins on alkaline phosphatase (ALP) activity in differentiating human MSC cells. ALP activity is a phenotypic marker for osteoblast differentiation.

Human MSC cells were cultured for 7 days in Osteoblast-Inducing media containing noggin (1 or 5 µg/ml) or partially-purified sclerostin protein (1 or 5 µg/ml). Cells were then harvested and analyzed for ALP activity. After 7 days of treatment, mouse noggin at 1 µg/ml had no effect on ALP activity, whereas mouse noggin at 5 µg/ml significantly increased ALP activity (p<0.001 to vehicle-treated cells). Under the same conditions, partially purified preparations of sclerostin consistently decreased ALP activity when administered at either 1 or 5

Figure 11:
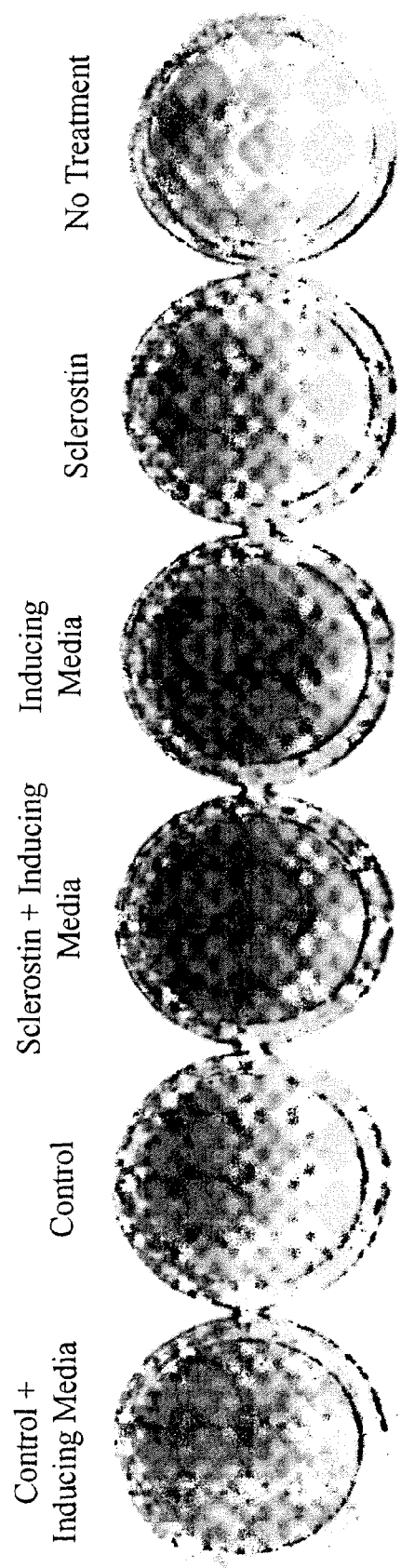

FIG. 11 illustrates that human sclerostin also decreased alkaline phosphatase activity in primary cultures of human osteoblasts. Primary human osteoblasts were grown in regular growth media or in Inducing media (to promote differentiation) and then treated with Sclerostin (20 µg/ml) or Control (protein purified from Sf9 conditioned media) for 7 days prior to histochemical staining for alkaline phosphatase activity. Osteoblasts grown in regular growth media expressed low, basal levels of ALP ("No Treatment," far right panel). These levels increased significantly when cells were grown in Inducing media (fourth panel, purple stain). When a similar group of cells were treated with sclerostin, there was a marked decrease in the amount of ALP expressed, as evidenced by the reduction in purple stain (third panel, "Sclerostin+Inducing Media").

Figure 12A:
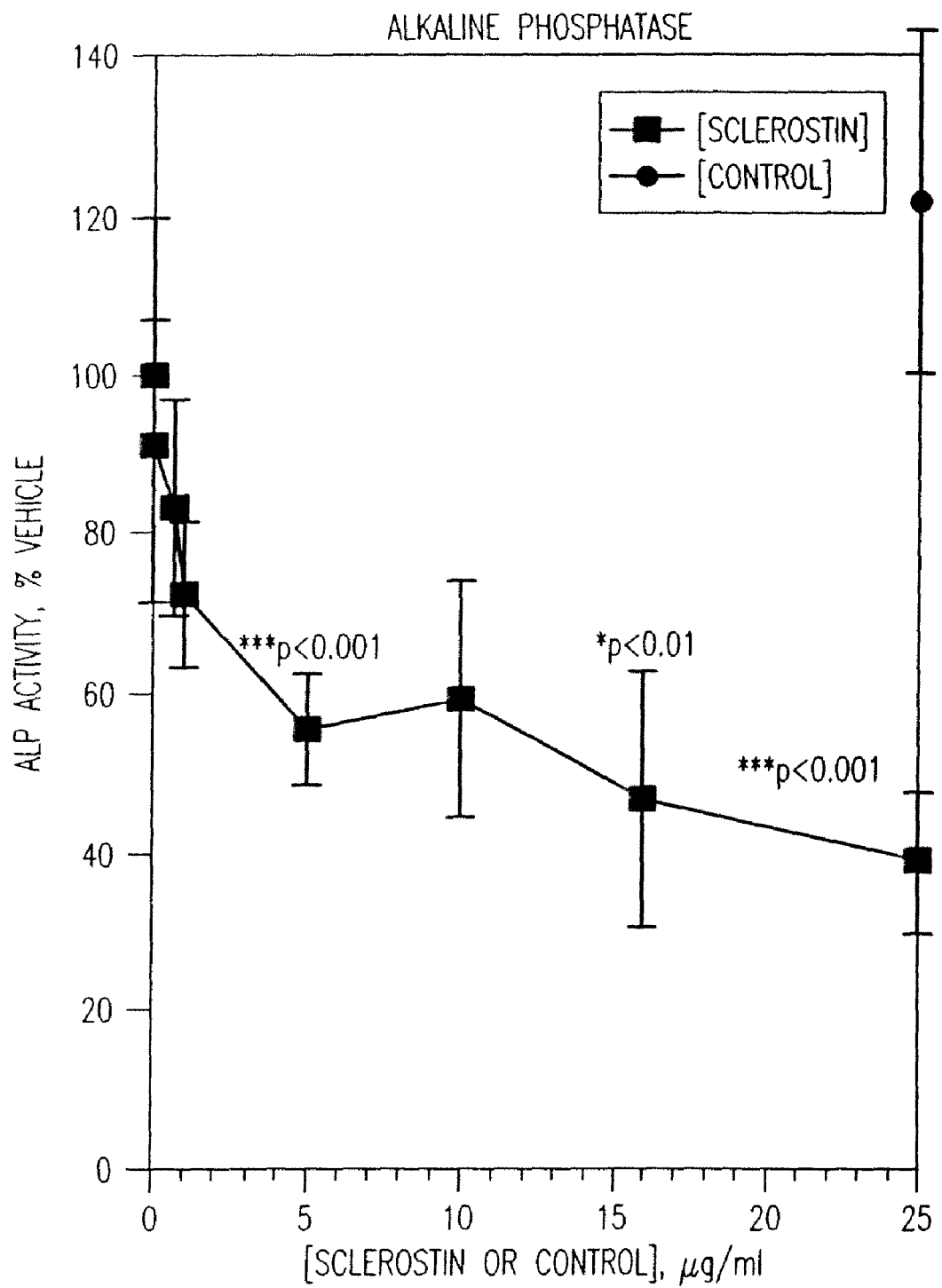

FIG. 12A illustrates that human sclerostin decreases alkaline phosphatase activity in hMSC cells in a dose-dependent manner. hMSC cells were plated in Osteoblast-Inducing media. Partially-purified sclerostin protein or proteins purified from Sf9 conditioned media (control) were added the next day. Cultures were maintained for 7 days prior to analysis for alkaline phosphatase activity. As illustrated, increasing concentrations of sclerostin give rise to decreasing levels of alkaline phosphatase activity.

Figure 12B:
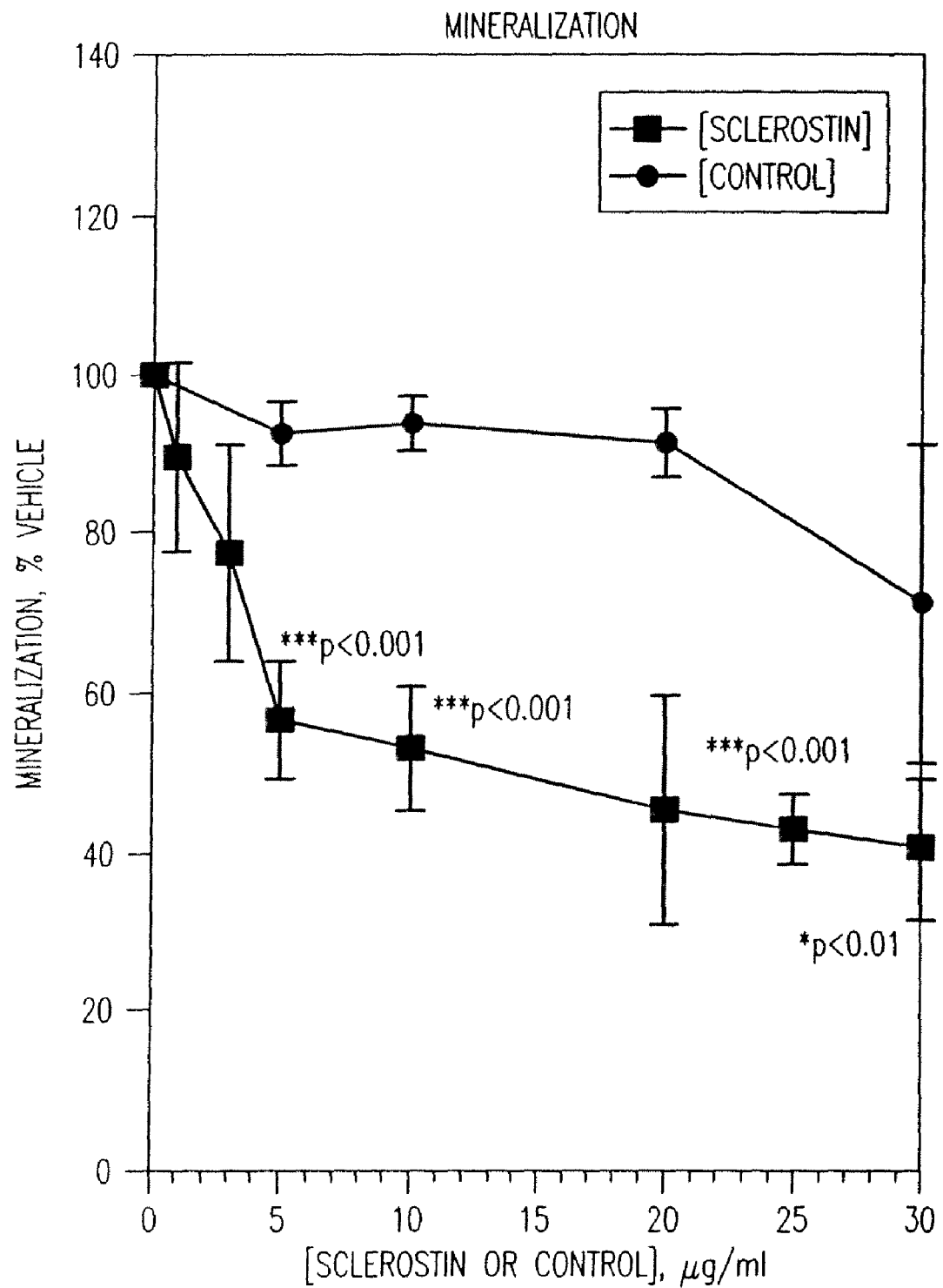

FIG. 12B illustrates that human sclerostin decreases mineralization (calcium deposition) in hMSC cells in a dose-dependent manner. hMSC cells were plated in Osteoblast-Inducing media. Partially-purified sclerostin protein or proteins purified from Sf9 conditioned media (control) were added the next day. Cultures were maintained for 8 days, treated with sclerostin or control proteins and maintained for another 13 days before testing for mineralization. As illustrated, increasing concentrations of sclerostin give rise to diminished mineralization.

Figure 13:
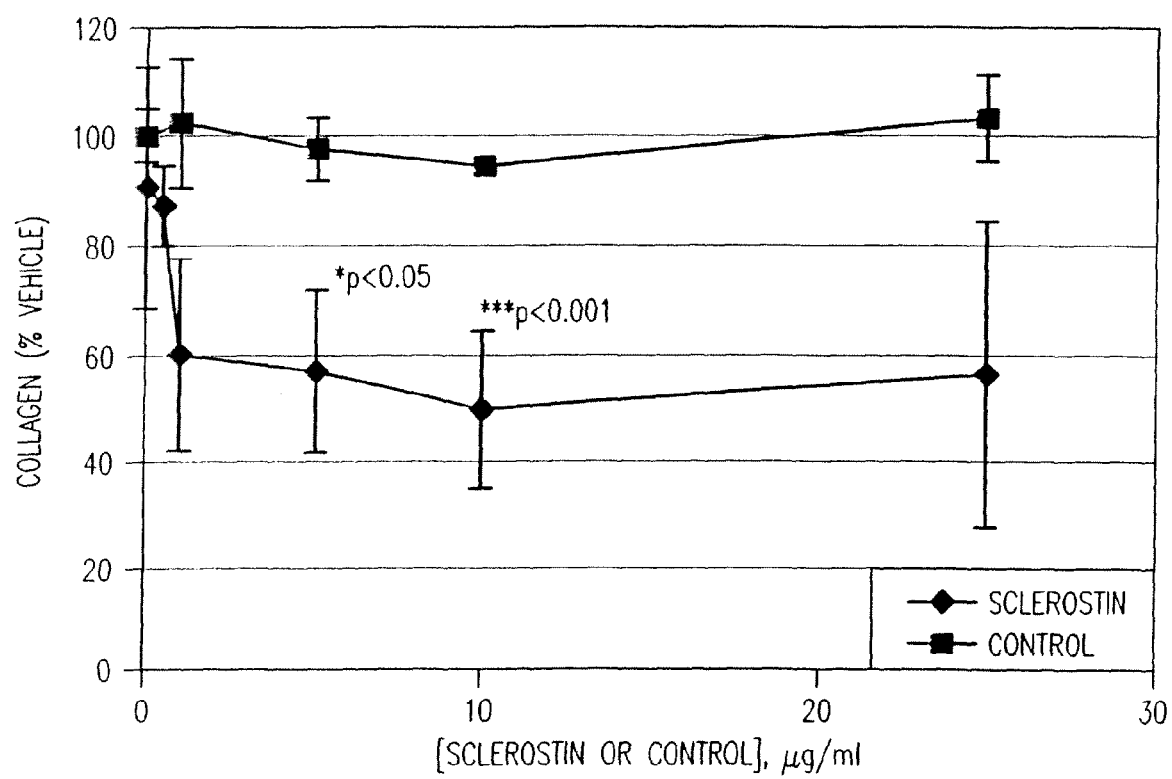

FIG. 13 illustrates that partially purified preparations of human sclerostin reduce the synthesis of type I collagen by about 50% in cells treated with 10 µg/ml of sclerostin (p<0.001 to control). hMSC cells were cultured in Osteoblast-Inducing media and treated with partially-purified sclerostin protein or proteins purified from Sf9 conditioned media (Control) for 21 days. Sclerostin or Control at the indicated concentrations was added 8 days after plating.

Figure 14:
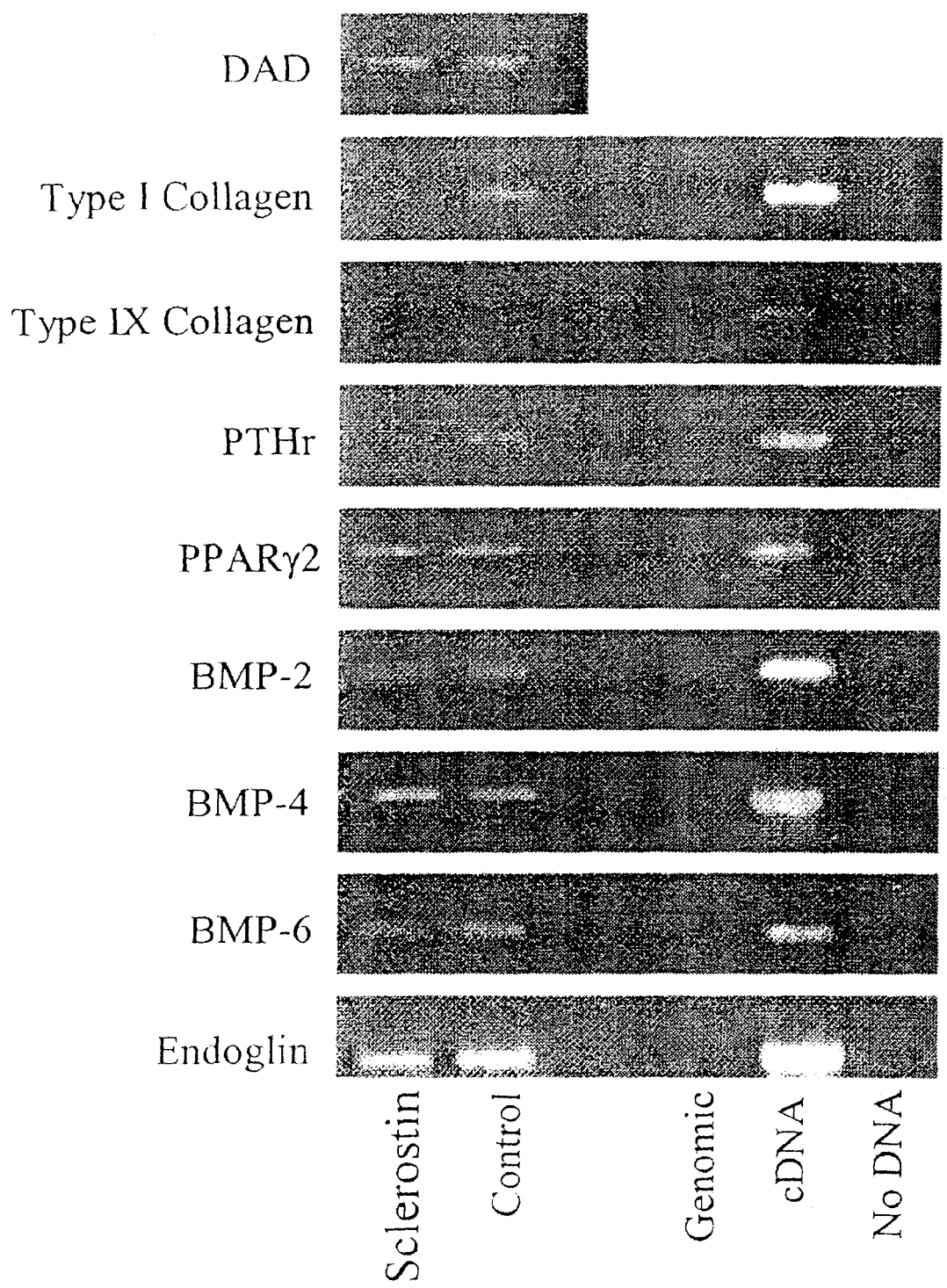

FIG. 14 illustrates that human sclerostin protein decreases expression of osteoblastic markers in cultures of differentiating hMSC cells. hMSC cells were plated in Osteoblast-Inducing media. After 3 days, partially purified sclerostin protein (10 µg/ml) or proteins purified from Sf9 conditioned media (control) were added. Cells were harvested after 40 hrs and RNA was prepared for RT-PCR analyses of osteoblastic markers. As can be seen, RNA levels of markers for adipocytes (PPARγ2) or undifferentiated mesenchymal cells (endoglin) were not affected by treatment with partially purified preparations of sclerostin protein. On the other hand, RNA levels for osteoblast phenotypic markers such as PTHr, Type I collagen, BMP-2 and BMP-6 were significantly reduced in cells treated with partially purified preparations of sclerostin protein compared to cells treated with control.

Figure 15:
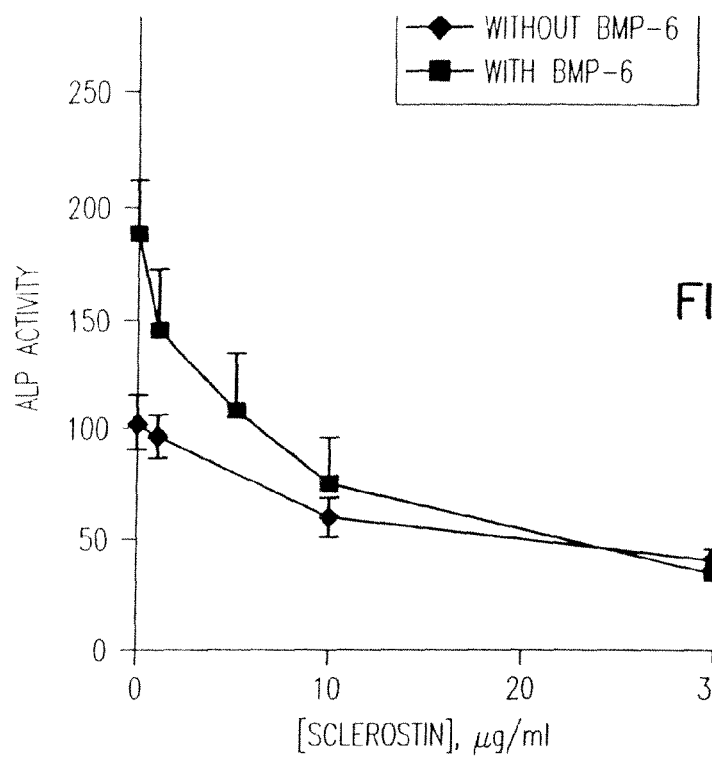

FIG. 15 illustrates that human sclerostin blocks BMP-6-stimulated activity as well as basal alkaline phosphatase activity in cultures of hMSC. Human MSC were plated in osteoblast-inducing media and treated with vehicle or BMP-6 (500 ng/ml) as well as increasing concentrations of human sclerostin-Flag protein. BMP-6 increased alkaline phosphatase activity. Sclerostin decreased BMP-induced alkaline phosphatase activity as well as basal levels of alkaline phosphatase activity in a dose dependent manner (p<0.0001).

Figure 16:
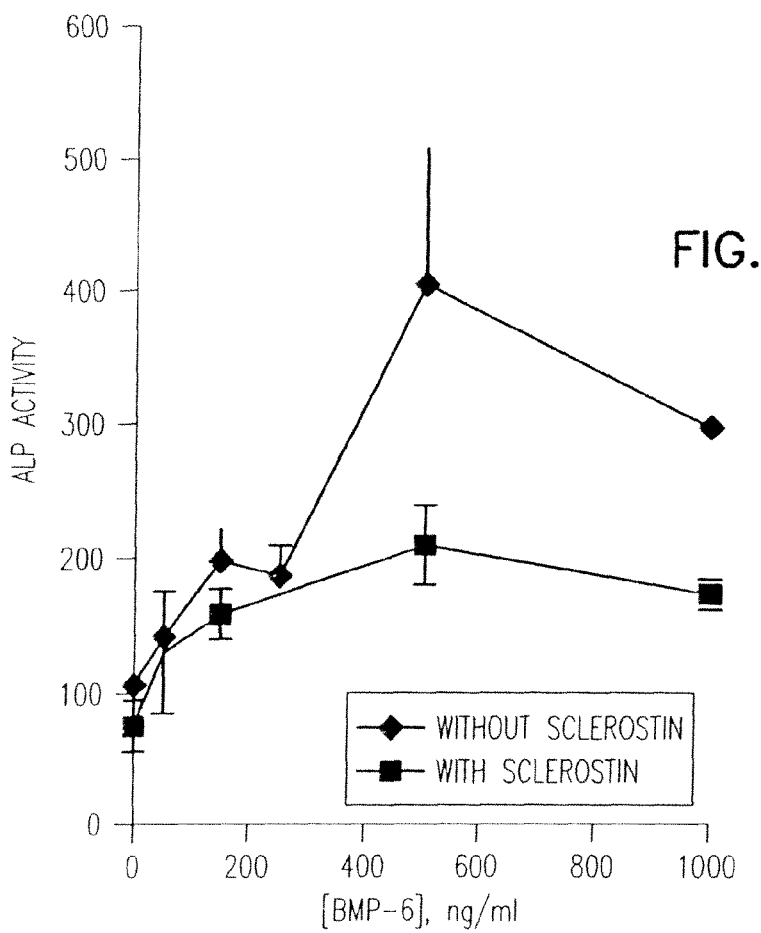

FIG. 16 illustrates that BMP-6 reverses the inhibitory effect of sclerostin on alkaline phosphatase in cultures of hMSC. hMSC were plated in osteoblast-inducing media and treated with sclerostin (10 µg/ml) and increasing amounts of BMP-6. While sclerostin decreased basal levels of ALP, BMP-6 reversed this effect in a dose-dependent manner (p<0.001).

Figure 17A:
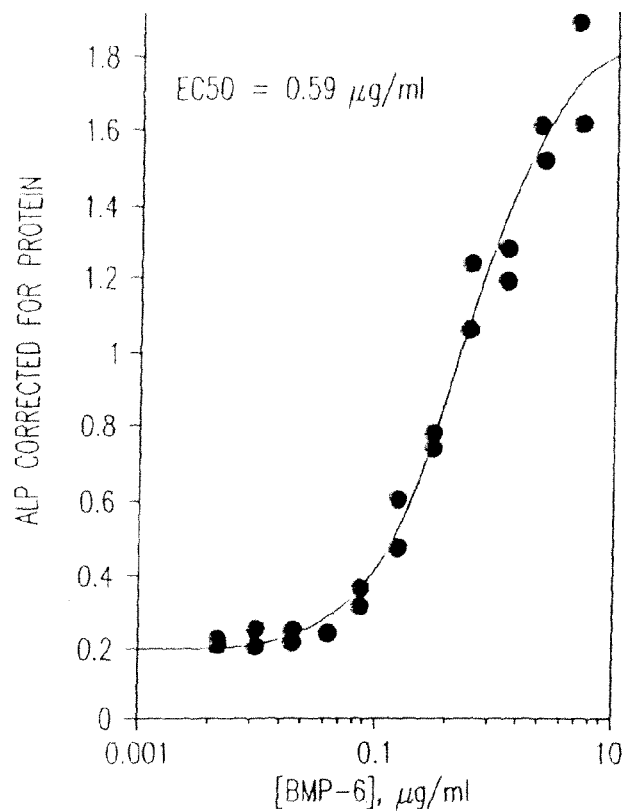
Figure 17B:
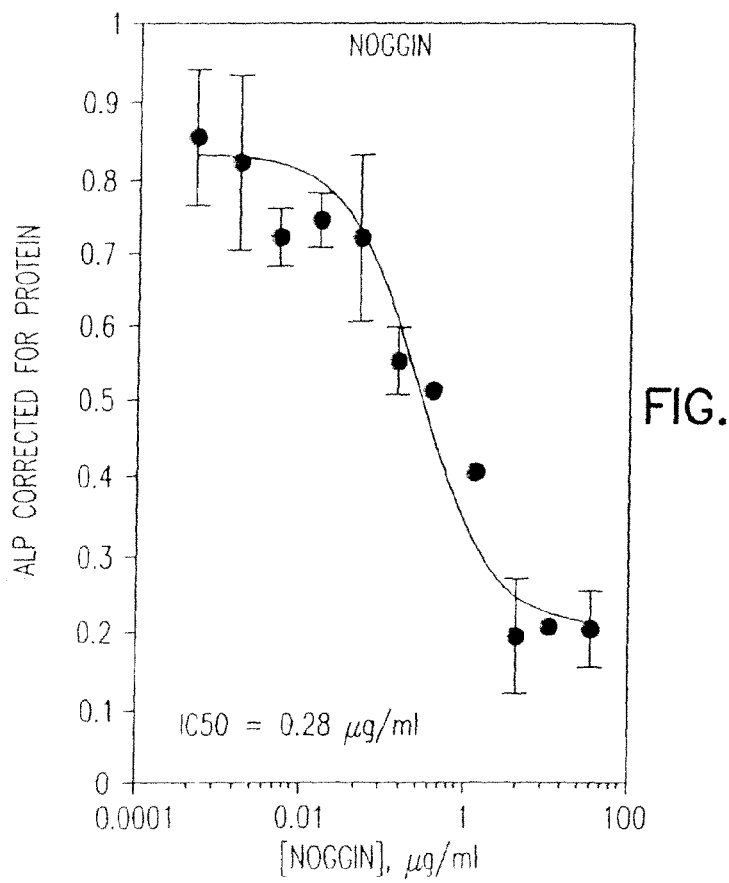
Figure 17C:
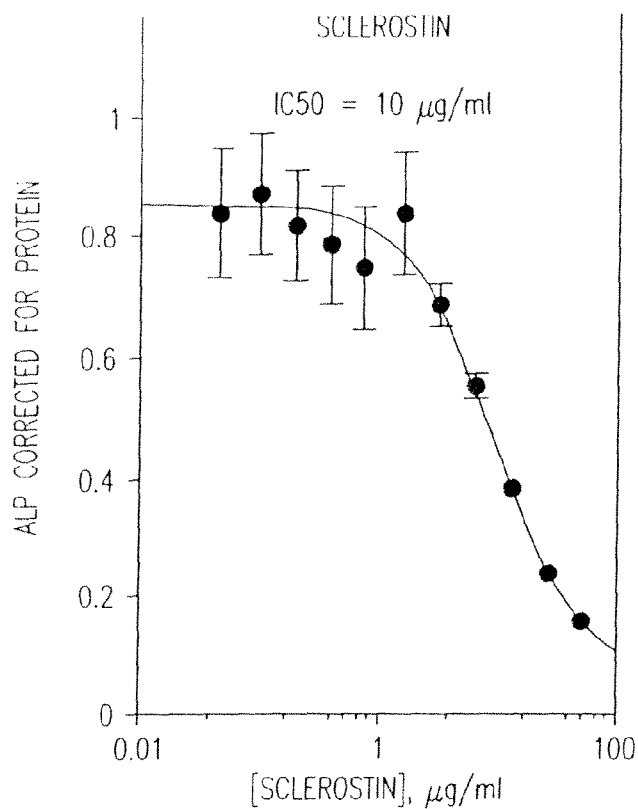
Figure 17D:
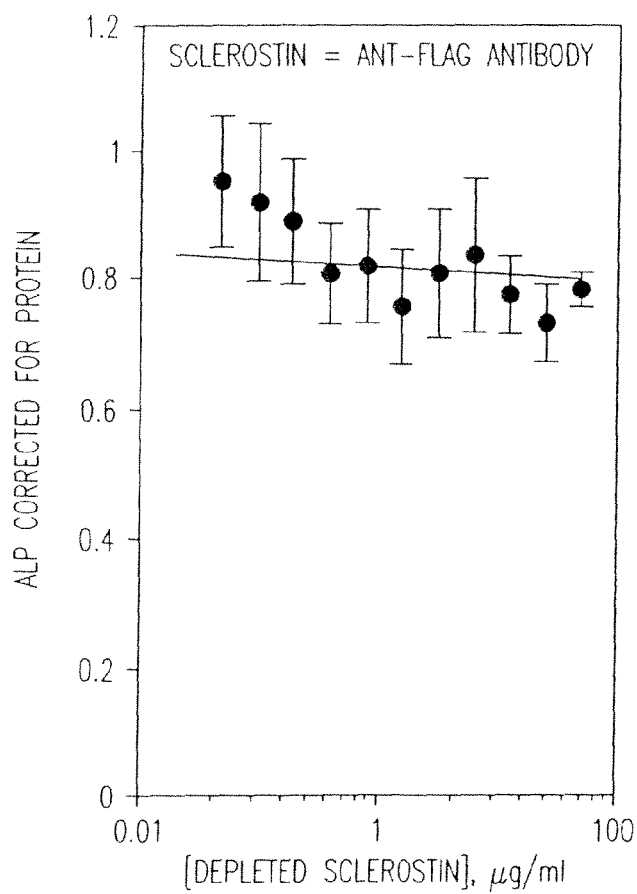

FIGS. 17A-17D illustrate that human sclerostin decreases alkaline phosphatase activity in mouse mesenchymal cells. Mouse mesenchymal C3H10T1/2 cells having ATCC Deposit No. CCL-226 were plated in regular growth media. Human sclerostin, sclerostin immuno-depleted with an anti-Flag M2 antibody and mouse noggin were pre-incubated with 500 ng/ml BMP-6 for 1 hr prior to addition to cells. Cells were then incubated for 72 hrs with the BMP-6, sclerostin, immuno-depleted sclerostin or noggin and tested for alkaline phosphatase activity. The stimulatory effect of BMP-6 (FIG. 17A) on alkaline phosphatase activity in the C3H10T1/2 cells was antagonized by noggin (FIG. 17B) and by sclerostin. To verify the specificity of the sclerostin response (FIG. 17C), sclerostin protein that had been synthesized with a Flag-tag was immuno-depleted by pre-treatment with an anti-Flag M2 antibody/agarose complex prior to addition to the cells. As can be seen in FIG. 17D, pre-treatment of the sclerostin preparation with an anti-Flag antibody completely abolished the antagonism of BMP-6 in the C3H10T1/2 cells, indicating that a sclerostin-specific response exists.

Figure 18:
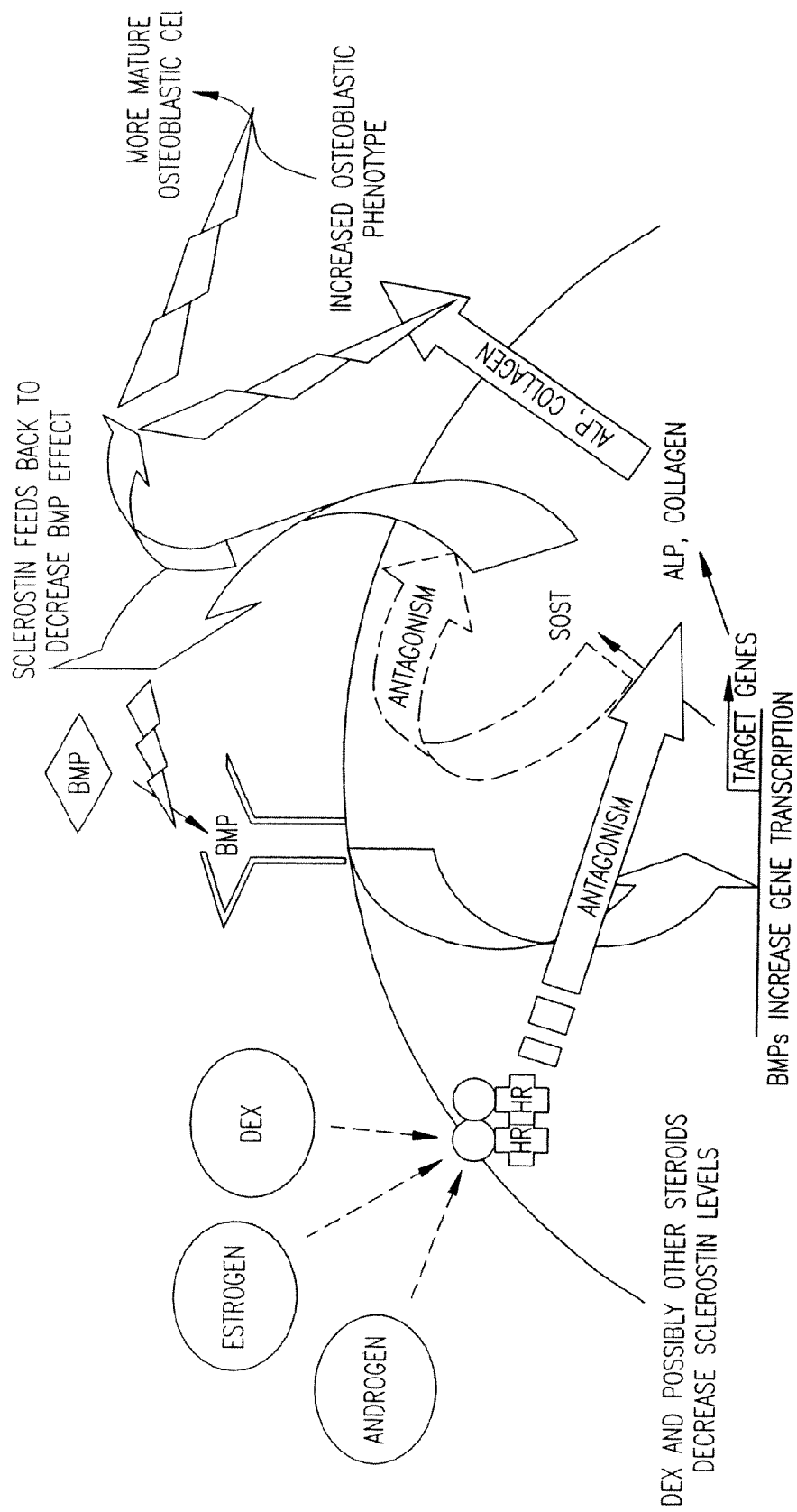

FIG. 18 provides a model of sclerostin activity. Bone morphogenetic proteins enhance the osteoblastic phenotype in osteoprogenitor cells by increasing the expression of osteoblastic markers (ALP, Collagen). Bone morphogenetic proteins also increase SOST levels. However, SOST feeds back to decrease Bone morphogenetic protein levels, resulting in decreased expression of osteoblastic markers. Steroids such as dexamethasone (and possibly estrogen, or androgen) bind to nuclear receptors (HR) and interact with the transcriptional machinery to reduce the production of SOST and therefore decrease sclerostin activity.

Figure 19:
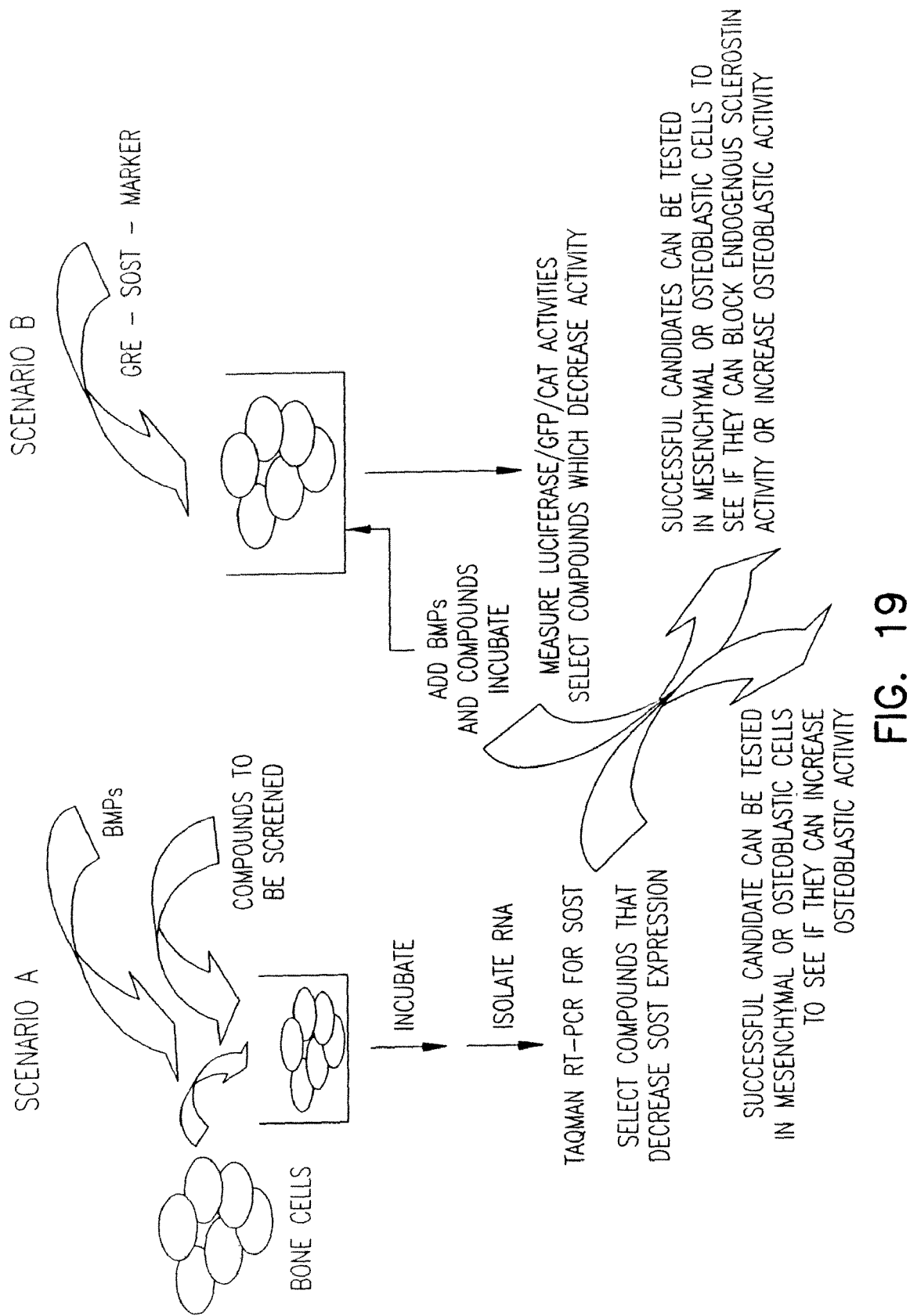

FIG. 19 illustrates screening assays provided by the invention for identifying factors that may down-regulate SOST expression. In both assays, the premise is that compounds bind to glucocorticoid receptor (GR) and interact with the BMP machinery to down-regulate activity of the SOST promoter, resulting in less SOST being transcribed. An example of a control compound is dexamethasone (DEX). In Scenario A, bone cells that are responsive to bone morphogenetic proteins and to glucocorticoids may be used to screen chemical libraries for compounds that would block the BMP-induced increase in SOST expression as measured by RT-PCR assays for SOST expression. Compounds selected to be of interest would be those that decrease the expression of SOST. In Scenario B, cultured cells that had been transfected with a DNA construct may be used to screen chemical libraries of compounds. The DNA construct is comprised of the SOST promoter sequence, a glucocorticoid response element (GRE) and a detectable marker (such as luciferase), for example, the DNA construct would have the structure:

GRE—SOST promoter-Luciferase

Compounds selected to be of interest would be those that decrease the expression of this DNA construct. Successful candidates from these screening assays can be tested in mesenchymal or osteoblastic cells to see if they can block endogenous sclerostin expression and/or increase osteoblastic activity in treated cells.

Figure 20:
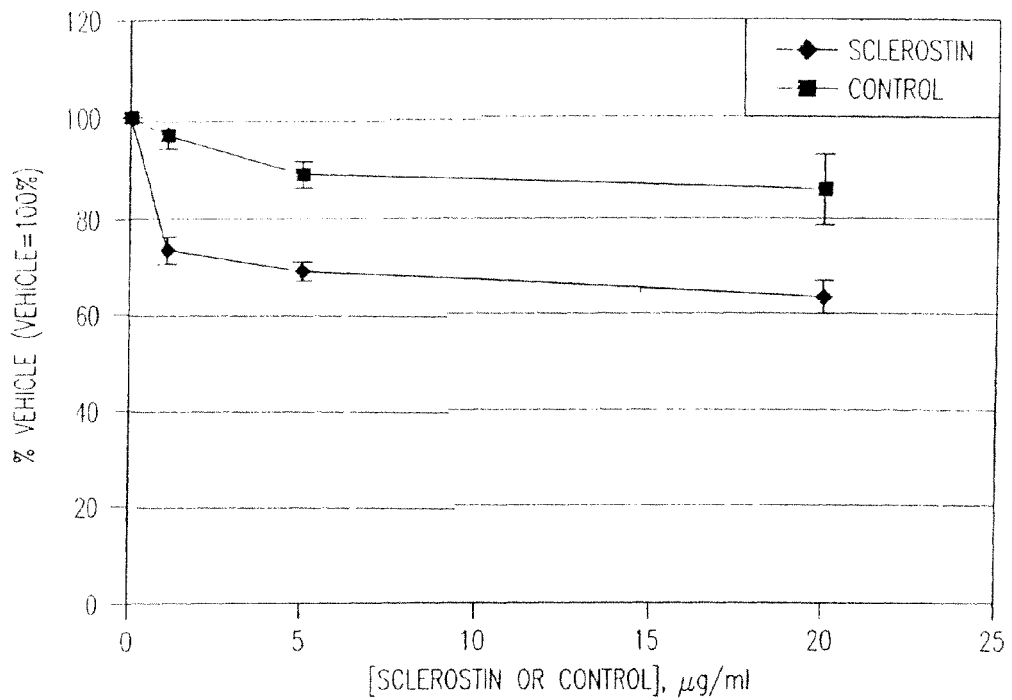
FIGS. 20 to 27 show that sclerostin affects the viability and the survival of osteoblastic bone cells.

FIG. 20 graphically illustrates that exposure to increasing amounts of human sclerostin decreases the viability of hMSC cells. hMSC cells were plated in Osteoblast-Inducing media and treated with baculo-expressed partially purified preparation of Sclerostin or proteins purified from Sf9 conditioned media (control) for 1 week. Sclerostin and Control were refreshed with each media change. After one week, cells were lysed and processed with Promega's CellTiterGlo Viability assay to detect what percentage of cells were viable. The viability of control and sclerostin-treated cells is plotted on the y-axis as the percentage of signal from vehicle-treated cells.

Figure 21:
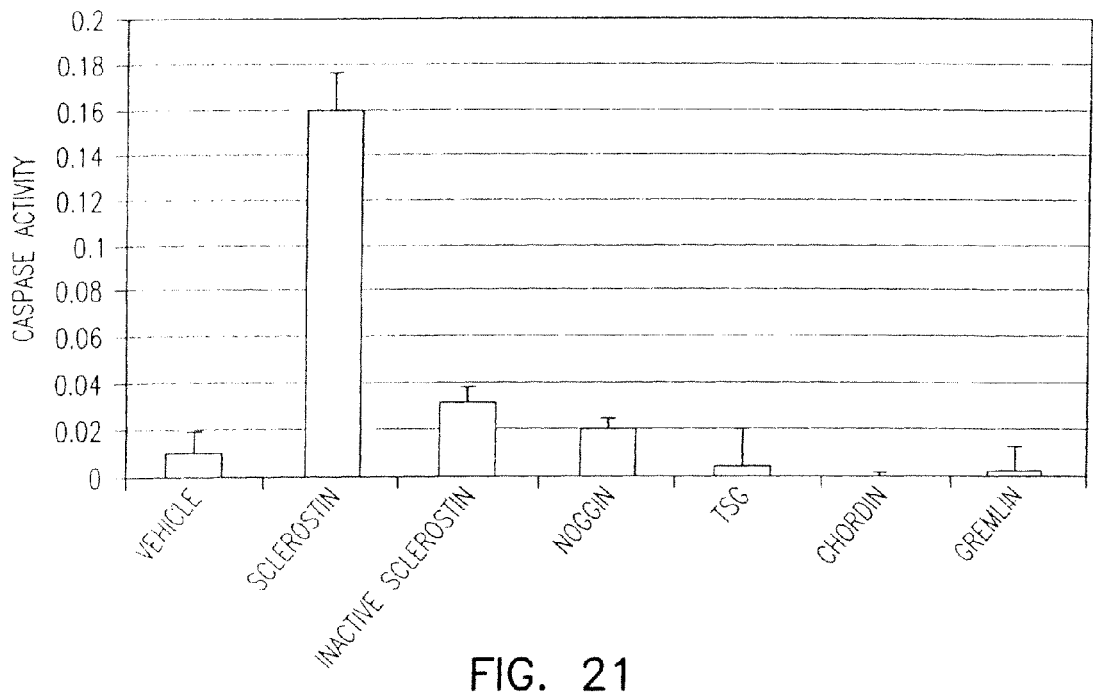

FIG. 21 shows that sclerostin, but not other BMP antagonists, increases the apoptosis of hMSC. hMSC were plated in osteoblast-inducing media and treated with 20 µg/ml sclerostin, inactivated sclerostin or one the BMP antagonists noggin, chordin, gremlin and twisted gastrulation (Tsg). Caspase activity was used as a measure of apoptosis. Sclerostin increased caspase activity whereas an inactive preparation of sclerostin or the BMP antagonists had no significant effect on caspase activity.

Figure 22A:
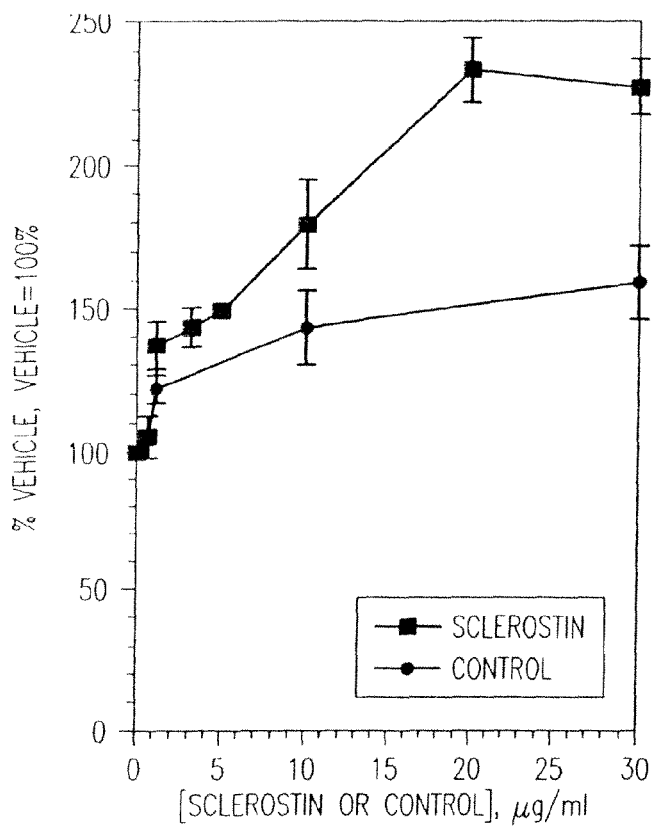

FIG. 22A graphically illustrates that exposure to increasing amounts of human sclerostin increases the apoptosis of hMSC cells in a dose-dependent manner. The amount of caspase activity was used as a measure of apoptosis. hMSC cells were plated in Osteoblast-Inducing media and treated with the indicated amounts of a partially purified preparation of sclerostin or proteins purified from Sf9 Conditioned media (control) for 24 hrs. As shown, increasing amounts of sclerostin lead to increased caspase activity.

Figure 22B:
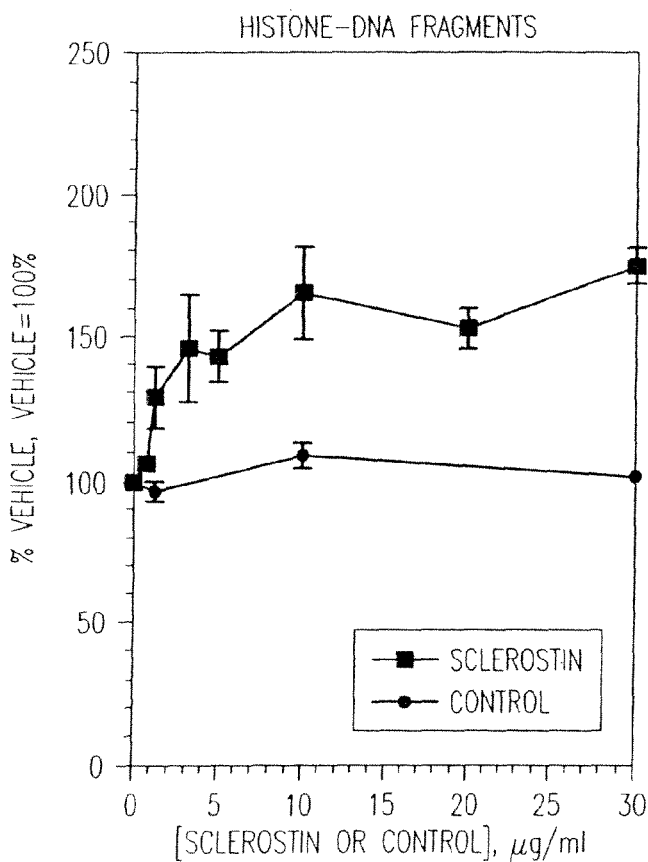

FIG. 22B graphically illustrates that exposure to increasing amounts of human sclerostin increases the apoptosis of hMSC cells in a dose-dependent manner. The amount of histone-DNA fragments as determined by ELISA (Roche) was used as a measure of apoptosis. hMSC cells were plated in Osteoblast-Inducing media and treated with the indicated amounts of a partially purified preparation of sclerostin or proteins purified from Sf9 conditioned media (control) for 24 hrs. As shown, increasing amounts of sclerostin lead to greater amounts of histone-DNA fragments.

Figure 23:
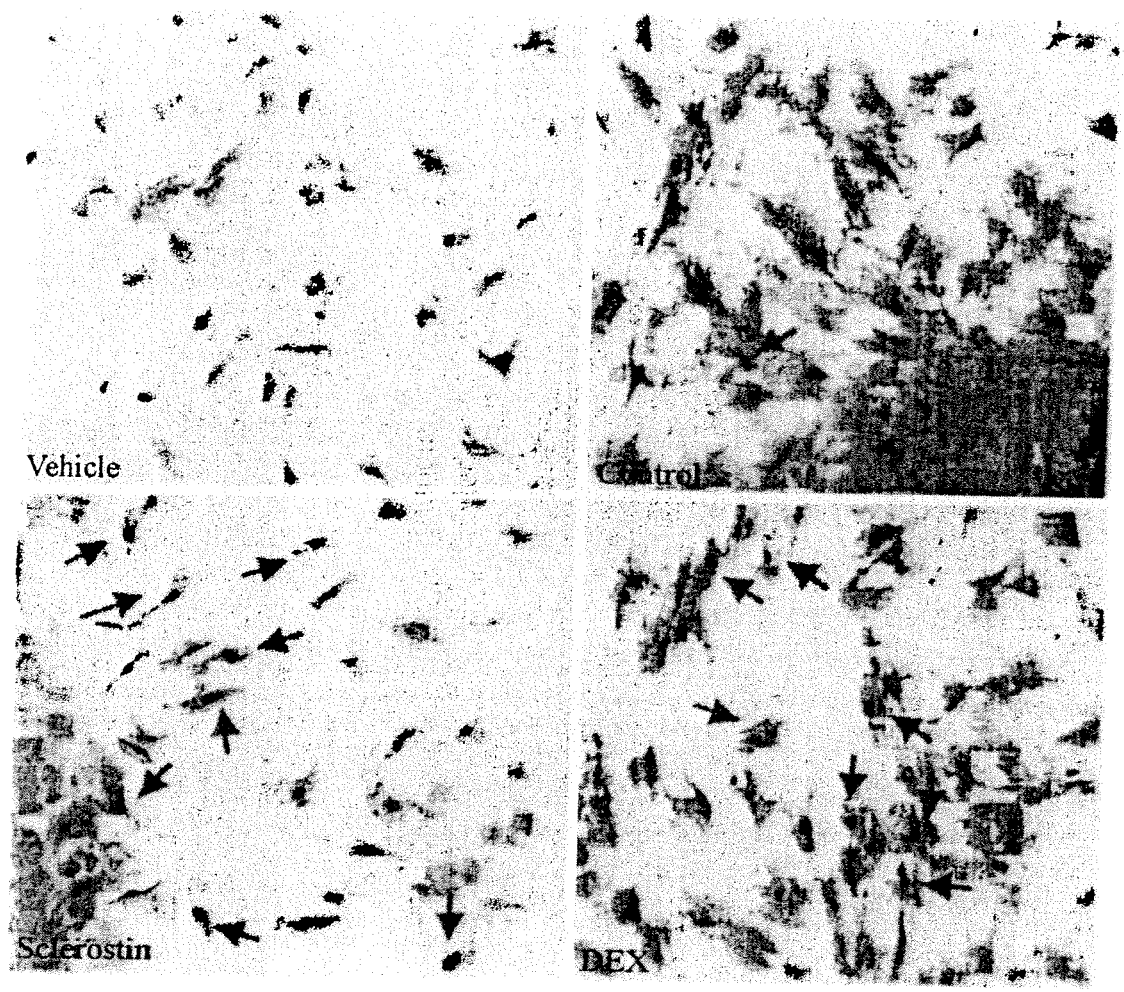

FIG. 23 illustrates that hMSC cells exposed to human sclerostin undergo apoptosis, as detected by Tunel staining for apoptotic nuclei. In contrast, hMSC cells exposed to vehicle or conditioned media show little evidence of apoptosis. hMSC cells were plated in Osteoblast-Inducing media and treated with a partially purified preparation of Sclerostin (20 µg/ml), proteins purified from Sf9 conditioned media (Control), or dexamethasone (DEX, 1 µM, positive control) for 24 hrs. Tunel staining for apoptotic nuclei (arrows point to positively stained nuclei) was performed using Roche's In Situ Cell Death Detection kit, Magnification, Bright field, 100×.

Figure 24A:
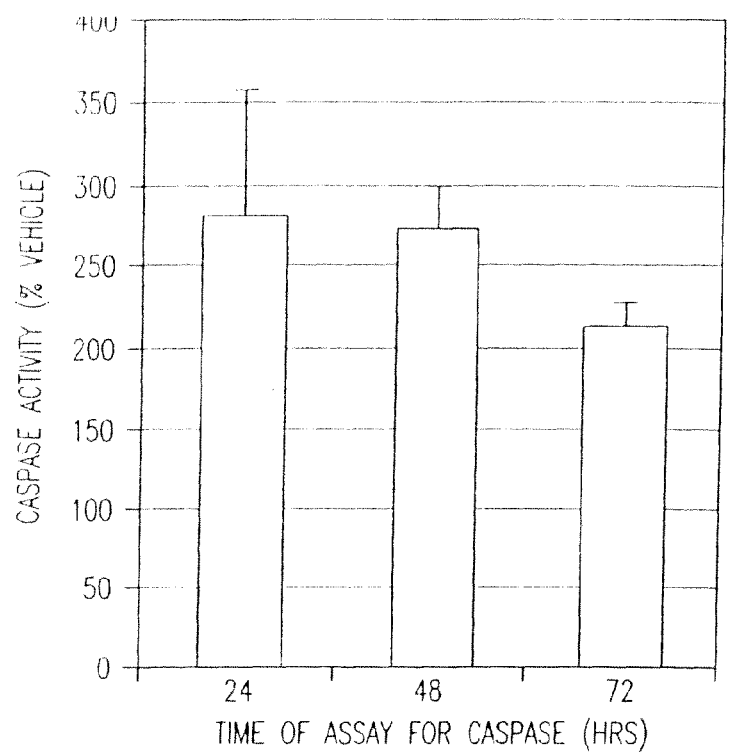

FIG. 24A shows the time course of effect of human sclerostin on the apoptosis of hMSC cells. hMSC cells were plated in Osteoblast-Inducing Media and treated with sclerostin. Cells were harvested and assayed for caspase activity at the indicated times. Caspase activity remained elevated 72 hrs after treatment of hMSC cells with sclerostin.

Figure 24B:
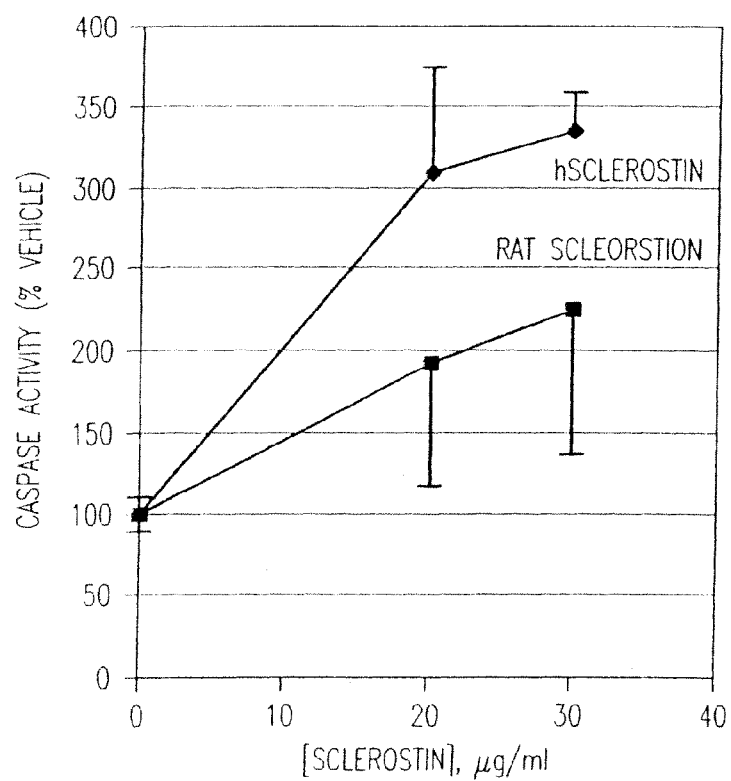

FIG. 24B illustrates that rat sclerostin also induced the apoptosis of hMSC cells. Human MSC cells were plated in Osteoblast-Inducing media and treated with human sclerostin or rat sclerostin for 24 hrs prior to assay for caspase activity (Roche).

Figure 25:
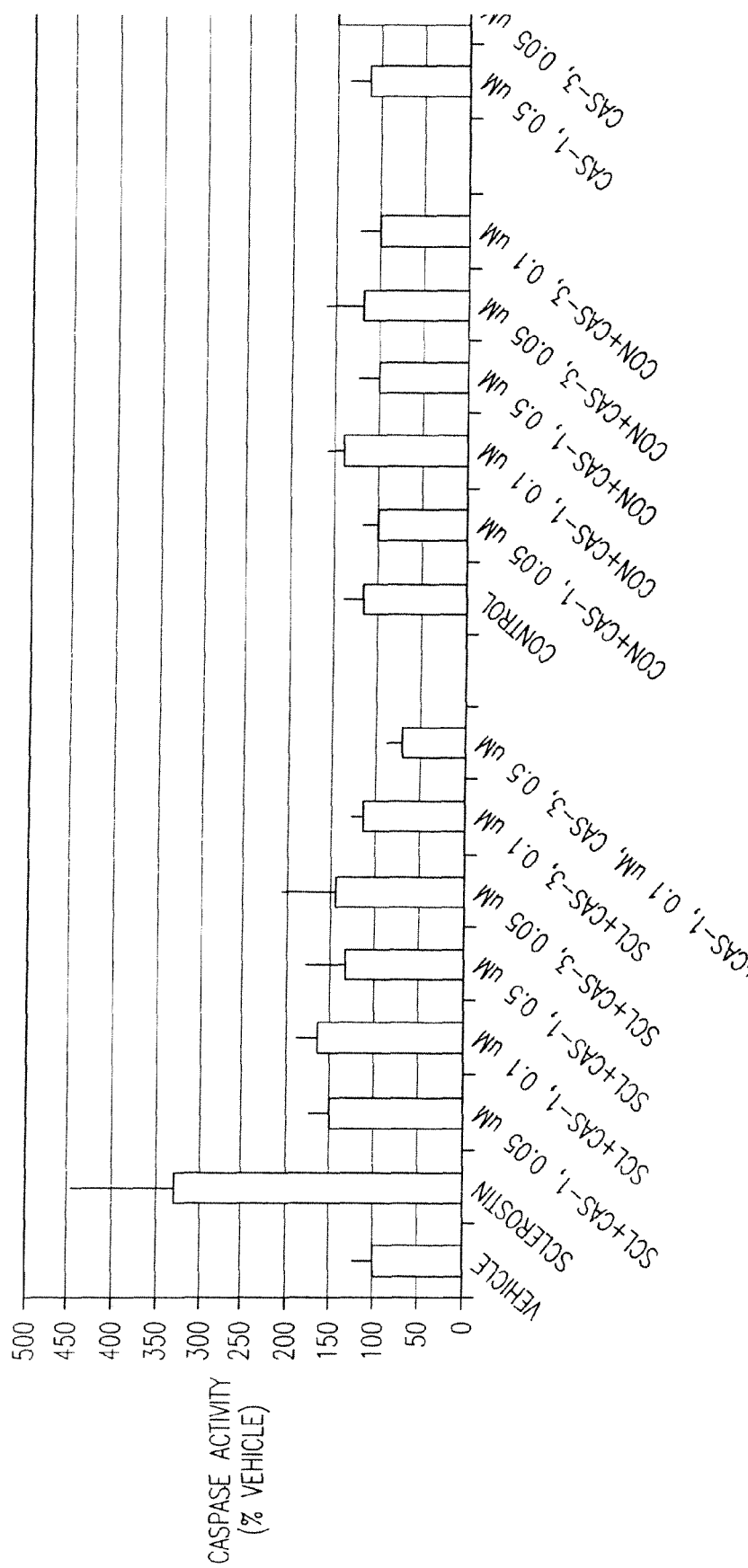

FIG. 25 shows that commercially available inhibitors of caspase activity can block the sclerostin-induced apoptosis of hMSC cells. hMSC cells were plated in Osteoblast-Inducing media and treated with human sclerostin or proteins purified from SD conditioned media (Control), in the presence or absence of caspase inhibitors for 24 hrs. Caspase activity was determined by Roche ELISA. Caspase inhibitors (Cas-1, Cas-3, Calbiochem) alone or in combination with each other efficiently blocked the sclerostin-induced increase in caspase activity. Caspase inhibitors also blocked caspase activity induced by rat sclerostin in these cells.

Figure 26:
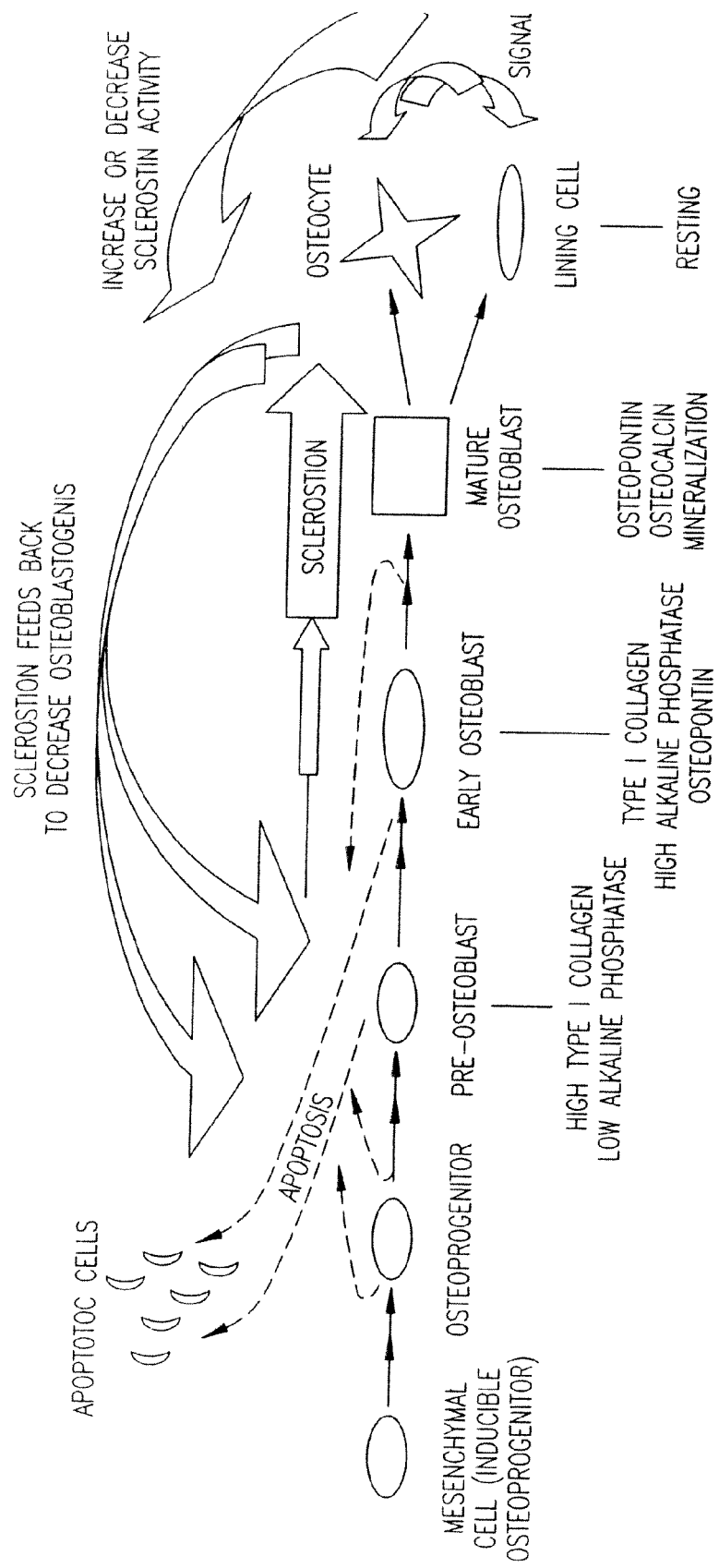

FIG. 26 provides a schematic diagram illustrating how sclerostin may induce apoptosis in maturing osteoblast cells. Mesenchymal cells develop along a defined temporal pathway from inducible progenitor cells to mature osteoblasts and finally, into lining cells or osteocytes. As these cells progress, they express phenotypic markers characteristic of each stage of differentiation (e.g. type I collagen for pre-osteoblasts, mineralization for mature osteoblasts). Sclerostin is highly expressed by maturing osteoblasts. Sclerostin regulates mineralization and hence bone formation by a negative feedback mechanism. Sclerostin decreases osteoblastogenesis by increasing the apoptosis of cells at early stages of osteoblast differentiation. Signals from osteocytes/lining cells regulate this entire process. Sclerostin may be an integral connection for osteocytic regulation of bone remodeling.

Figure 27:
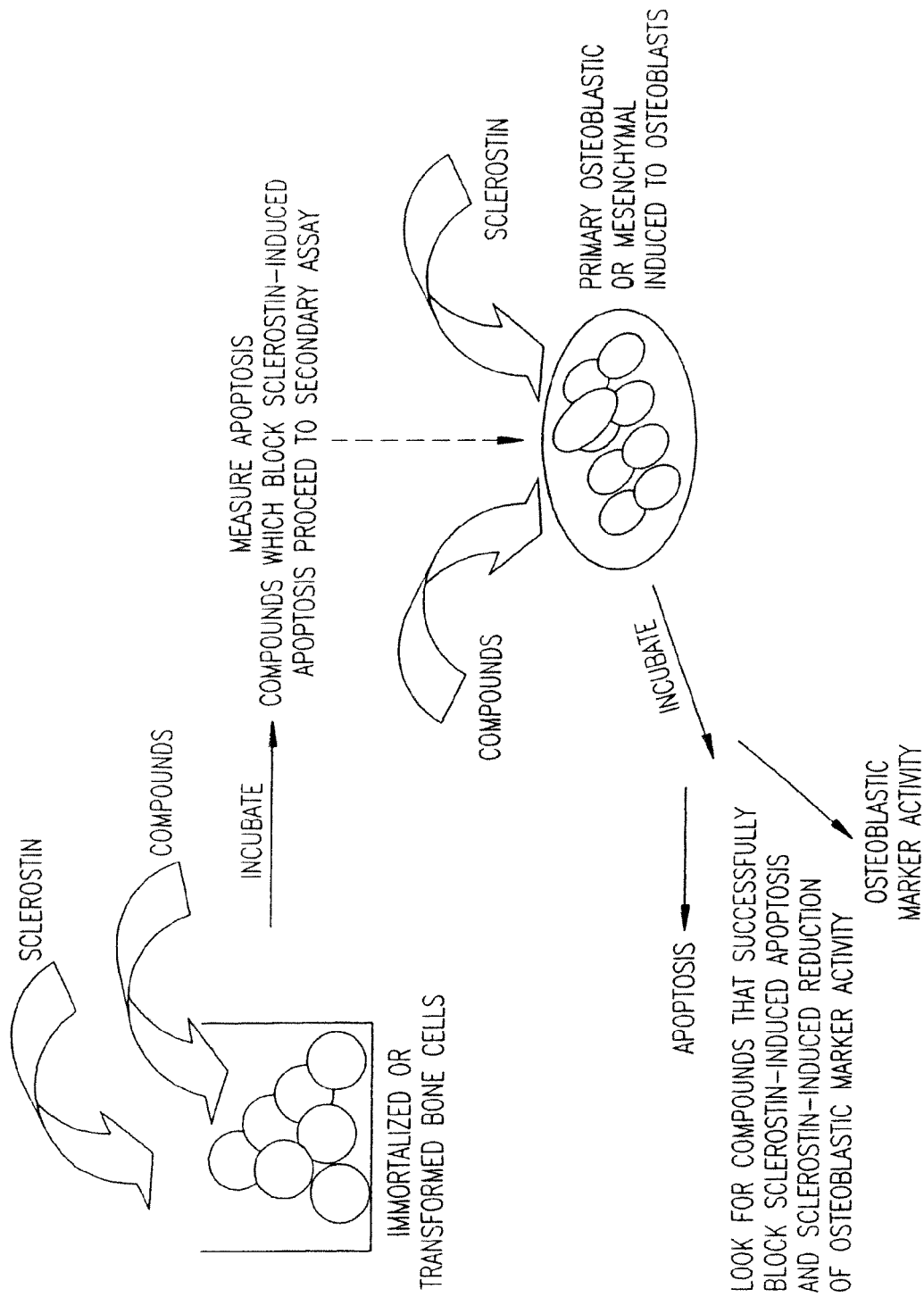

FIG. 27 provides one possible assay for sclerostin antagonists. In this assay, a variety of cells may be tested separately. In one assay, immortalized or transformed bone cells can be cultured in the presence of sclerostin and a test compound or test sample. In another assay, primary osteoblastic or mesenchymal cells that can be induced to differentiate are exposed to a test compound or test sample. After a period of incubation, apoptosis is measured. Factors that reduce apoptosis are candidate sclerostin antagonists that can be further characterized in a number of ways as illustrated herein.

DETAILED DESCRIPTION OF THE INVENTION

The invention provides compositions and methods for modulating bone density in a mammal. In particular, the invention provides factors that diminish SOST expression and antagonists of the SOST gene product, sclerostin. According to the invention, sclerostin decreases bone mineralization, collagen synthesis and alkaline phosphatase (ALP) activity in maturing bone cells in both direct and indirect ways. One way that sclerostin regulates bone density and bone formation is by acting as an antagonist of bone morphogenetic proteins (BMPs). Another way that sclerostin regulates bone density and formation is through apoptosis of cells involved in bone mineralization and bone formation.

By modulating or diminishing the amount of sclerostin or by inhibiting its action, bone morphogenetic proteins can perform essential functions needed for the commitment and differentiation of osteoprogentior cells and pre-osteoblastic cells. Moreover, by administering antagonists of sclerostin-mediated apoptosis, the survival and longevity of cells involved in bone mineralization can be increased. Such compositions and procedures provide therapeutic strategies for increasing bone mineralization and formation.

The invention further provides assays for identifying factors that diminish SOST expression and/or antagonists that counteract the effects of sclerostin.

Bone Cell Development

A small population of pluripotent mesenchymal/stromal cells, called inducible osteoprogenitor cells, can be induced to differentiate into osteoblastic cells (Pittenger, M F et al.

1999). These inducible osteoprogenitor cells develop and express certain phenotypic markers in a defined, sequential manner (Pockwinse et al. 1992; Lian et al. 1999). Osteoprogenitor cells express type I collagen whereas committed pre-osteoblasts and osteoblasts express many of the phenotypic markers that are typically identified with a cell of the osteoblast lineage. These markers include type I collagen, alkaline phosphatase, parathyroid hormone receptor (PTHr) and osteopontin. In the terminal stage of osteoblast differentiation, osteocytes are surrounded by deposits of mineral as well as matrix proteins such as CD44 and osteocalcin. Therefore, the development, growth and differentiation of osteoblastic precursor cells into mature osteoblasts occur in a defined, time-dependent manner (Pockwinse et al., 1992).

The expression of phenotypic markers that are characteristic of osteoblasts at different stages of differentiation is regulated by a variety of factors, including the bone morphogenetic proteins (BMPs). It is thought that BMP-6 may initiate osteoblast differentiation at an early osteoprogenitor stage but that other bone morphogenetic proteins or growth factors may be necessary to continue the differentiation process (Gitelman et al., 1995; Boden et al., 1997). Certain studies indicate that BMP-2 and BMP-4 are needed for the commitment and differentiation of osteoprogenitor and pre-osteoblastic cells to osteoblasts (Katagiri et al., 1990; Oreffo et al. 1999; Suzawa et al., 1999).

Antagonists of bone morphogenetic proteins, for example, noggin, gremlin, chordin and the Dan/cereberus family of proteins, have also been identified. However, the role that bone morphogenetic protein antagonists play in the regulation and modulation of bone morphogenetic protein action in osteoblastic cells is not well understood.

SOST and Sclerostin

The sequence of the human SOST gene is approximately 22 kb and can be found as Genbank Accession No. AF326736 in the NCBI nucleotide database (SEQ ID NO:1). See website at ncbi.nlm.nih.gov/Genbank/GenbankOverview. Co-owned and co-assigned U.S. Pat. Nos. 6,395,511 and 6,489,445, incorporated by reference herein, provide additional sequence information and a further description of the properties of the SOST gene and its gene product (called beer therein).

The human SOST cDNA has Genbank Accession No. NMO25237, and is provided for the convenience of the reader as follows (SEQ ID NO:2).

```
   1 AGAGCCTGTG CTACTGGAAG GTGGCGTGCC CTCCTCTGGC
  41 TGGTACCATG CAGCTCCCAC TGGCCCTGTG TCTCGTCTGC
  81 CTGCTGGTAC ACACAGCCTT CCGTGTAGTG GAGGGCCAGG
 121 GGTGGCAGGC GTTCAAGAAT GATGCCACGG AAATCATCCC
 161 CGAGCTCGGA GAGTACCCCG AGCCTCCACC GGAGCTGGAG
 201 AACAACAAGA CCATGAACCG GGCGGAGAAC GGAGGGCGGC
 241 CTCCCCACCA CCCCTTTGAG ACCAAAGACG TGTCCGAGTA
 281 CAGCTGCCGC GAGCTGCACT TCACCCGCTA CGTGACCGAT
 321 GGGCCGTGCC GCAGCGCCAA GCCGGTCACC GAGCTGGTGT
 361 GCTCCGGCCA GTGCGGCCCG GCGCGCCTGC TGCCCAACGC
 401 CATCGGCCGC GGCAAGTGGT GGCGACCTAG TGGGCCCGAC
 441 TTCCGCTGCA TCCCCGACCG CTACCGCGCG CAGCGCGTGC
 481 AGCTGCTGTG TCCCGGTGGT GAGGCGCCGC GCGCGCGCAA
 521 GGTGCGCCTG GTGGCCTCGT GCAAGTGCAA GCGCCTCACC
 561 CGCTTCCACA ACCAGTCGGA GCTCAAGGAC TTCGGGACCG
 601 AGGCCGCTCG GCCGCAGAAG GGCCGGAAGC CGCGGCCCCG
 641 CGCCCGGAGC GCCAAAGCCA ACCAGGCCGA GCTGGAGAAC
 681 GCCTACTAGA GCCCGCCCGC GCCCCTCCCC ACCGGCGGGC
 721 GCCCCGGCCC TGAACCCGCG CCCCACATTT CTGTCCTCTG
 761 CGCGTGGTTT GATTGTTTAT ATTTCATTGT AAATGCCTGC
 801 AACCCAGGGC AGGGGGCTGA GACCTTCCAG GCCCTGAGGA
 841 ATCCCGGGCG CCGGCAAGGC CCCCCTCAGC CCGCCAGCTG
 881 AGGGGTCCCA CGGGGCAGGG GAGGGAATTG AGAGTCACAG
 921 ACACTGAGCC ACGCAGCCCC GCCTCTGGGG CCGCCTACCT
 961 TTGCTGGTCC CACTTCAGAG GAGGCAGAAA TGGAAGCATT
1001 TTCACCGCCC TGGGGTTTTA AGGGAGCGGT GTGGGAGTGG
1041 GAAAGTCCAG GGACTGGTTA AGAAAGTTGG ATAAGATTCC
1081 CCCTTGCACC TCGCTGCCCA TCAGAAAGCC TGAGGCGTGC
1121 CCAGAGCACA AGACTGGGGG CAACTGTAGA TGTGGTTTCT
1161 AGTCCTGGCT CTGCCACTAA CTTGCTGTGT AACCTTGAAC
1201 TACACAATTC TCCTTCGGGA CCTCAATTTC CACTTTGTAA
1241 AATGAGGGTG GAGGTGGGAA TAGGATCTCG AGGAGACTAT
1281 TGGCATATGA TTCCAAGGAC TCCAGTGCCT TTTGAATGGG
1321 CAGAGGTGAG AGAGAGAGAG AGAAAGAGAG AGAATGAATG
1361 CAGTTGCATT GATTCAGTGC CAAGGTCACT TCCAGAATTC
1401 AGAGTTGTGA TGCTCTCTTC TGACAGCCAA AGATGAAAAA
1441 CAAACAGAAA AAAAAAGTA AAGAGTCTAT TTATGGCTGA
1481 CATATTTACG GCTGACAAAC TCCTGGAAGA AGCTATGCTG
1521 CTTCCCAGCC TGGCTTCCCC GGATGTTTGG CTACCTCCAC
1561 CCCTCCATCT CAAAGAAATA ACATCATCCA TTGGGGTAGA
1601 AAAGGAGAGG GTCCGAGGGT GGTGGGAGGG ATAGAAATCA
1641 CATCCGCCCC AACTTCCCAA AGAGCAGCAT CCCTCCCCCG
1681 ACCCATAGCC ATGTTTTAAA GTCACCTTCC GAAGAGAAGT
1721 GAAAGGTTCA AGGACACTGG CCTTGCAGGC CCGAGGGAGC
1761 AGCCATCACA AACTCACAGA CCAGCACATC CCTTTTGAGA
1801 CACCGCCTTC TGCCCACCAC TCACGGACAC ATTTCTGCCT
1841 AGAAAACAGC TTCTTACTGC TCTTACATGT GATGGCATAT
1881 CTTACACTAA AAGAATATTA TTGGGGGAAA AACTACAAGT
1921 GCTGTACATA TGCTGAGAAA CTGCAGAGCA TAATAGCTGC
1961 CACCCAAAAA TCTTTTTGAA AATCATTTCC AGACAACCTC
2001 TTACTTTCTG TGTAGTTTTT AATTGTTAAA AAAAAAAGT
2041 TTTAAACAGA AGCACATGAC ATATGAAAGC CTGCAGGACT
2081 GGTCGTTTTT TTGGCAATTC TTCCACGTGG GACTTGTCCA
```

```
2121 CAAGAATGAA AGTAGTGGTT TTTAAAGAGT TAAGTTACAT
2161 ATTTATTTTC TCACTTAAGT TATTTATGCA AAAGTTTTTC
2201 TTGTAGAGAA TGACAATGTT AATATTGCTT TATGAATTAA
2241 CAGTCTGTTC TTCCAGAGTC CAGAGACATT GTTAATAAAG
2281 ACAATGAATC ATGACCGAAA GAAAAAAAA AAAAAAAAAA
2321 AAA
```

The SOST gene gives rise to the sclerostin protein. The human sclerostin protein has Genbank Accession No. NP079513 and is provided below for convenient reference as SEQ ID NO:3.

```
  1 MQLPLALCLV CLLVHTAFRV VEGQGWQAFK NDATEIIPEL
 41 GEYPEPPPEL ENNKTMNRAE NGGRPPHHPF ETKDVSEYSC
 81 RELHFTRYVT DGPCRSAKPV TELVCSGQCG PARLLPNAIG
121 RGKWWRPSGP DFRCIPDRYR AQRVQLLCPG GEAPRARKVR
161 LVASCKCKRL TRFHNQSELK DFGTEAARPQ KGRKPRPRAR
201 SAKANQAELE NAY
```

The promoter for the human SOST gene is found within nucleotides 7960-11960 of SEQ ID NO:1. This promoter sequence is provided below as SEQ ID NO:4.

```
7960 T
7961 GAATGCCACA GCTTGTCAGC AGCCAGCAGA AGGCAGGTAA
8001 AAGGCCTTCC TCACTGTCCT CGAAGGAACC AACTCTGCCA
8041 ATGTCTTGAA CTTGCACTCC TAACCTCCAG CTCTGTGAGA
8081 CGACTTCTGT TGTTTATGCC ACCCAATTTG TGGTACTTAG
8121 TTACGGCAGC CTCATCAAAG TACCACCTAT GGGAGCCTCT
8161 ATTTTGCAGG TGAGGGCGGG GACTGGGCTG AGTTTTCTGG
8201 AAAACAGCCC TGCAATACCC TCATCAGACC ACCAAACTCT
8241 TCACACTCCC TCAGACACAG CATTCACTTC CAGAAATAAC
8281 TCTAAAGTTT TGTTTTGTTT TTTTAAACTT TGTGGAATAC
8321 TACTCAGCCA AAAAAAAAAA AAAGAAAAG AAAAAGGAAC
8361 ATGTTACTGA TATGTACAAC TTGGATAATG GAAATAATGC
8401 TGAGTGAAAA AAAAATCCCC AAAGGCTACA TACTAATTGA
8441 TTCCATTTAT ATAACCTTTT TTTTTTTTTT TTGAGACAGT
8481 CTCACTCTGT CACCCAGGCT GGAGCACAGT GGCGCGATCT
8521 CAGCTCACTG CAACTTCCGC CTCCTGAGTT CAAGCGATTC
8561 TCTTGCCTTA GCTTCCCAAG TAGCTGGGAT TACAGGTGCG
8601 TGCCACCATG CCCAGCTAAT TTTTGTATTT TTAGTAGAGA
8641 CAGGGTTTCG CCATGTTGGC CAGGCTGGTC TCGAACTCCT
8681 GACCTCAAGT GATCTGCCTG CCTTGGCTTC CCAAAGTGCT
8721 GGGATTACAT GAGTGAGCCA CCGCACCTGG TCGCATTTAT
8761 GTAACAATTT TGAAGTGAAA AAAAAAATGA CAGAAATGGA
8801 GATTAGATGA GTAGTTGCCA GGGGTTAGTT GTGGGAGGGA
8841 GGGAAAAGGA GGGAAGGAGG TGGGCAACAG GAGAAAGACT
8881 TGTGGTCACA GAGCTGTGCT TTATCTTGAC TGTGGTGGAT
8921 CCCCAAATTT ACCCGTGACA AGATTGCATA GAACTAAGTA
8961 TACACACACG TGAATGCGTG TGCACGCACA CAGTAGAGGT
9001 TAAGCCACGG GAGATGTGGG TAAGATTGGT AAATTGTGTC
9041 AATATCAATA TCCTAGTTGT GATATTGTCC TATAGTTTCG
9081 CAAGGTGTTA TTGTTGTGGG AAACTGGATA AAGGATACAC
9121 GGAGTCTGCA TTTTCTTTTT TTTATTTTTA TTTTTTGAGA
9161 CGGGGTCTCA CTCTGTCAAC CAGGCTGGAG TGCAGTGGCC
9201 CAAGTATGGC TCACTGCAGC CTCGACCTCA ACCTCAAGTG
9241 AACCTCCCAC CTCAGCCTCC CAAGTAGCTA AGACCACAGG
9281 CGTGCGACCC CATGCCCAGC TAATTTTTAA ATTTTTTGTA
9321 GAGACTAGGC CTCACCATGT TGCCCAGGCT TTTATTTCTT
9361 ATAAGTATAT TTAAATTTAT AATTATATCC ACATTTTAAA
9401 ATTTTAATTT AAAAAATTAC TCTGAGGCCG GGCATTGTGG
9441 CTCATGCCTC TAATCCCCAG CACCTTGGGA GGCCGAGTTG
9481 GGCAGATCAC CCGAGGTCAG AAGTTCGAGA CCAGCCTGAG
9521 TAACATGGAG AAACCCCCGT CTCTACTAAA AATACAAAAT
9561 TGGCCGGGCG TGGTGGTGC TTCCTGTAAT CCCAGCTACT
9601 CGGGAGGCTG AGGCAGGAGA ATTGCTTGAA CCCAGGAGGT
9641 GGAGGTTGCA GTGAGCCAAG ATTGTGCCAC TGCACTGCAG
9681 CCTGGGCCAC AGAGAGAATC TGCCAAAAA AGAAAAAAAA
9721 AAAAATTTCA GCCGTACAAG GATGTTCATA GCAACCCTGC
9761 TGGAAATAGG AAAAAAAATT GGAAATAACC TAAACTACTC
9801 ACAATAGGAA TCAGCTAAAA CCCTGGGGGT TTAATTCCAG
9841 GGAATACTGT GAACAATGAC AAGTTTGTGG ACTGAGTAAA
9881 AATAAACAGC TGTCAATGAC TTAACATTAA ATGAAACAGC
9921 AGAAGATGTC ACAGCAGGTT CTCGCTGAGC CATTCAGAGG
9961 GGTGTGGATC ATTTAGAGGT TCAAGTCCAC TGGATTCTTC
10001 TTTTTCCTTT TAATATTACT TCACTTCCAA ATAAGGAAAG
10041 GAAAGGAAAG GAAATCACGT CCAGTCCTGA GACTTGCCAT
10081 CCTGCAGTCA CCCCTCCTTT TGTCTCCAGC AGGTGGCAGA
10121 CGCGTTCCAG GGATGAATCC CACTGCCTCT GTTTAATGCA
10161 GACGGTCCAG CCGCTCCCAA CAGCAGGTGG GGCTATAAGC
10201 ATCCATCCTA CCTGCTCAAG GAACCCAGGC ATCAGAACTG
10241 CTCTCTCCCA AGTCCATTGC AAGAAGGCAG TCGTCTGGTC
10281 ATGAGAGGGT TAACAGTCCA CATTCCAGAG CAAGGGAAAA
10321 GGAGGCTGGA GGGTCATAGA CAAGGGGAGG TGGTGCGGAG
```

```
10361 GGCCAGCTTC TCACAACACT ACCGGCTCTG CTGGGAGAGA
10401 TAGATCACCC CCAACAATGG CCACAGCTGT TTTCATCTGC
10441 CCTGAAGGAA ACTGACTTAG GAAGCAGGTA TCAGAGAGGG
10481 CCCTTCCTGA GGGGGCTTCT GTCTGGCTTG TAAAACTGTC
10521 AGAGCAGCTG CATTCATGTG TCGGATGATG GATGATGGAA
10561 AGGACAGTCG GCTGCAGATG GACACAGCGA CTTGCAAGTT
10601 GAGGCAGGTG GCAAAGGACT TGCAGAGGCT CTGCAGGTGG
10641 GGCATGCTGA TTCATTGCCC AGTTAAAATA CCAGAGGATC
10681 TGGGCAGCCT CTTCACAGGA GCTGCTTGTC CTCAAACAAT
10721 CTGTCTTCAA TGAAAGATTC CTCTGGCCTT CCTTTCTCTT
10761 CTTGCACCTC AGGTGTGAAT CCTTCTCCCC CACGCCTCTA
10801 CCTGCGCCCC CGCCCCCCGC CCCGGCCCTG TGTGGCTCAT
10841 TATATGCAGG GCCAAGGCAG CATTTTCTCT TAGCTTCTTT
10881 GTGACCAGTT GGTCCTGGGA TGGCTTCATG GAACACATCC
10921 TGTGGTGTGC ACCAATGAAG CTTTCCATAC AGGACTCAAA
10961 ACTGTTTTTG AAAAATGTAA CCAGCTGGAA GACAAGAAAA
11001 TAAAATGTCA GCACTAAAAA CGCTGGCTGT GGCTTTTGCT
11041 AAGGAAAGGA ATTTGGTGTT GTCTTCTCAC ACACACAGAC
11081 TGGTTGGGGA AATGACTGTC TTCAGCACAT CACCCTGCGA
11121 GCCACAGTGA GTGCCCTGGC TCAGAAGTGC CTGTCACAGT
11161 GCACAGGATC CCTGAGGAGC ATGAGCTGGG ATTTCCTCTG
11201 TGCTGTCCAT CACAGGAGCC TGAGTGACCA GCGCATCCTC
11241 GATTTGTAAC CAGAATCCTG CCCTCTCTCC CAAGCGGGCA
11281 CCCTTGCTCT GACCCTCTAG TTCTCTCTCT TGCCTTCCAG
11321 AGAATACCAA GAGAGGCTTT CTTGGTTAGG ACAATGAATG
11361 CTGAGACTTG TGGAGTTGGG ACCAATGGGA TTTCTTTAAA
11401 AGCATCTTTT TGCCTCTGGC TGGGTCTATG GGGGTCAAAC
11441 AGAAACACCT TGGGCCATTT GTTGGTGGGG TGACAAATGA
11481 ACTTGGCCTG AGAAATGGAA TAGGCCGGGC TCAGCCCCGC
11521 GAAGCACTCA GAACTGCACA TTTTCTTTGT TGAGCGGGTC
11561 CACAGTTTGT TTTGAGAATG CCCGAGGGCC CAGGGAGACA
11601 GACAATTAAA AGCCGGAGCT CATTTGATA TCTGAAAACC
11641 ACAGCCGCCA GCACGTGGGA GGTGCCGGAG AGCAGGCTTG
11681 GGCCTTGCCT CACACGCCCC CTCTCTCTGG GTCACCTGGG
11721 AGTGCCAGCA GCAATTTGGA AGTTTGCTGA GCTAGAGGAG
11761 AAGTCTTTGG GGAGGGTTTG CTCTGAGCAC ACCCCTTTCC
11801 CTCCCTCCGG GGCTGAGGGA AACATGGGAC CAGCCCTGCC
11841 CCAGCCTGTC CTCATTGGCT GGCATGAAGC AGAGAGGGGC
11881 TTTAAAAAGG CGACCGTGTC TCGGCTGGAG ACCAGAGCCT
11921 GTGCTACTGG AAGGTGGCGT GCCCTCCTCT GGCTGGTACC
11960 ATGCAGCTCC CACTGGCCCT GTGTCTCGTC TGCCTGCTG
```

The invention can also be practiced with variants of the SOST gene and with variants of the sclerostin protein. For example, the invention can be practiced with the mouse or rat SOST gene or with the mouse or rat sclerostin protein. The mouse SOST cDNA has Genbank Accession No. NM024449, and is provided below as SEQ ID NO:5 for easy reference.

```
  1 ATGCAGCCCT CACTAGCCCC GTGCCTCATC TGCCTACTTG
 41 TGCACGCTGC CTTCTGTGCT GTGGAGGGCC AGGGGTGGCA
 81 AGCCTTCAGG AATGATGCCA CAGAGGTCAT CCCAGGGCTT
121 GGAGAGTACC CCGAGCCTCC TCCTGAGAAC AACCAGACCA
161 TGAACCGGGC GGAGAATGGA GGCAGACCTC CCCACCATCC
201 CTATGACGCC AAAGATGTGT CCGAGTACAG CTGCCGCGAG
241 CTGCACTACA CCCGCTTCCT GACAGACGGC CCATGCCGCA
281 GCGCCAAGCC GGTCACCGAG TTGGTGTGCT CCGGCCAGTG
321 CGGCCCCGCG CGGCTGCTGC CAACGCCAT CGGGCGCGTG
361 AAGTGGTGGC GCCCGAACGG ACCGGATTTC CGCTGCATCC
401 CGGATCGCTA CCGCGCGCAG CGGGTGCAGC TGCTGTGCCC
441 CGGGGGCGCG GCGCCGCGCT CGCGCAAGGT GCGTCTGGTG
481 GCCTCGTGCA AGTGCAAGCG CCTCACCCGC TTCCACAACC
521 AGTCGGAGCT CAAGGACTTC GGGCCGGAGA CCGCGCGGCC
561 GCAGAAGGGT CGCAAGCCGC GGCCCGGCGC CCGGGGAGCC
601 AAAGCCAACC AGGCGGAGCT GGAGAACGCC TACTAG
```

The mouse sclerostin protein has Genbank Accession No. NP077769, and is provided below as SEQ ID NO:6 for easy reference.

```
  1 MQPSLAPCLI CLLVHAAFCA VEGQGWQAFR NDATEVIPGL
 41 GEYPEPPPEN NQTMNRAENG GRPPHHPYDA KDVSEYSCRE
 81 LHYTRFLTDG PCRSAKPVTE LVCSGQCGPA RLLPNAIGRV
121 KWWRPNGPDF RCIPDRYRAQ RVQLLCPGGA APRSRKVRLV
161 ASCKCKRLTR FHNQSELKDF GPETARPQKG RKPRPGARGA
201 KANQAELENA Y
```

The rat SOST cDNA has Genbank Accession No. NM030584, and is provided below as SEQ ID NO:7 for easy reference.

```
  1 GAGGACCGAG TGCCCTTCCT CCTTCTGGCA CCATGCAGCT
 41 CTCACTAGCC CCTTGCCTTG CCTGCCTGCT TGTACATGCA
 81 GCCTTCGTTG CTGTGGAGAG CCAGGGGTGG CAAGCCTTCA
121 AGAATGATGC CACAGAAATC ATCCCGGAC TCAGAGAGTA
161 CCCAGAGCCT CCTCAGGAAC TAGAGAACAA CCAGACCATG
```

```
-continued
201  AACCGGGCCG AGAACGGAGG CAGACCCCCC CACCATCCTT

241  ATGACACCAA AGACGTGTCC GAGTACAGCT GCCGCGAGCT

281  GCACTACACC CGCTTCGTGA CCGACGGCCC GTGCCGCAGT

321  GCCAAGCCGG TCACCGAGTT GGTGTGCTCG GGCCAGTGCG

361  GCCCCGCGCG GCTGCTGCCC AACGCCATCG GGCGCGTGAA

401  GTGGTGGCGC CCGAACGGAC CCGACTTCCG CTGCATCCCG

441  GATCGCTACC GCGCGCAGCG GGTGCAGCTG CTGTGCCCCG

481  GCGGCGCGGC GCCGCGCTCG CGCAAGGTGC GTCTGGTGGC

521  CTCGTGCAAG TGCAAGCGCC TCACCCGCTT CCACAACCAG

561  TCGGAGCTCA AGGACTTCGG ACCTGAGACC GCGCGGCCGC

601  AGAAGGGTCG CAAGCCGCGG CCCCGCGCCC GGGGAGCCAA

641  AGCCAACCAG GCGGAGCTGG AGAACGCCTA CTAG
```

The rat sclerostin protein has Genbank Accession No. NP085073, and is provided below as SEQ ID NO:8 for easy reference.

```
  1  MQLSLAPCLA CLLVHAAFVA VESQGWQAFK NDATEIIPGL

41  REYPEPPQEL ENNQTMNRAE NGGRPPHHPY DTKDVSEYSC

81  RELHYTRFVT DGPCRSAKPV TELVCSGQCG PARLLPNAIG

121  RVKWWRPNGP DFRCIPDRYR AQRVQLLCPG GAAPRSRKVR

161  LVASCKCKRL TRFHNQSELK DFGPETARPQ KGRKPRPRAR

201  GAKANQAELE NAY
```

Other SOST nucleic acids and sclerostin proteins can be used for the practice of the invention, including the vervet SOST cDNA [accession number AF326742] and the bovine SOST cDNA [accession number AF326738].

According to the invention, the expression of the SOST gene increases with the maturation and differentiation of osteoblasts as well as with the onset of mineralization. Hence, SOST expression can be used as a marker for osteoblast differentiation.

However, factors that increase SOST expression lead to decreased bone mineralization because the SOST gene product, sclerostin, is an antagonist of bone morphogenetic proteins and causes apoptosis of osteoblasts. Sclerostin decreased the expression of many phenotypic markers of pre-osteoblasts/osteoblasts (ALP, type 1 collagen, PTHr) when it was added to cultures of differentiating hMSC cells and primary cultures of osteoblastic cells. Moreover, sclerostin interacted with and antagonized the activity of BMP-6, thereby inhibiting osteoblast differentiation.

According to the invention, sclerostin plays an integral role in the regulation of bone matrix formation and mineralization. Although several proteins are thought to function as antagonists of bone morphogenetic protein action (for example, noggin and gremlin), it appears that when the sclerostin function is lost that function cannot be replaced by noggin or any of the other members of the DAN family of antagonists.

A schematic diagram of how sclerostin to affects bone cell biology is depicted in FIG. 26. Sclerostin exerts its effects on pre-osteoblasts, osteoprogenitor, and mature osteoblasts cells. By depriving pre-osteoblasts and osteoprogenitor cells of factors such as bone morphogenetic proteins, these cells are prevented from completing their differentiation into mature osteoblasts. Thus, fewer osteoblasts are available to provide mineralization. In addition, these proteins play important anti-apoptotic roles, which are potentially impacted by increasing exposure to sclerostin. As a result, alkaline phosphatase activity and synthesis of type collagen are reduced in pre-osteoblasts and osteoprogenitor cells, while mineralization is affected in mature osteoblasts treated with sclerostin. Reducing the expression of SOST or the amount of sclerostin available to developing osteoblasts permits more cells to progress through differentiation to produce more mature osteoblasts, more synthesis of type I collagen and greater deposition of mineral in bones.

Several factors enhance the expression of SOST, including insulin-like growth factor-1 and bone morphogenetic proteins such as BMP-2, BMP-4, and BMP-6. When bone morphogenetic proteins are present, retinoic acid and vitamin D also enhanced the levels of SOST expression. Such factors can therefore lead to diminished collagen synthesis and less mineralization within bones through increased synthesis of sclerostin.

In contrast, SOST expression levels decrease when dexamethasone is present with BMP-4 or BMP-6. Therefore, dexamethasone tends to abolish the stimulatory effect of BMP-4 and BMP-6 on SOST expression. Other chemical entities including glucocorticoid analogs, bile salts and prostaglandins also modulate the effects of bone morphogenetic proteins on SOST expression, as described below.

Modulating SOST/Sclerostin

According to the invention, any agents that modulate the ability of sclerostin to decrease osteoblastic activity are useful in increasing bone formation, modulating bone resorption and augmenting bone mineralization. Such agents can act directly or indirectly on SOST or sclerostin. Such agents can act at the transcriptional, translational or protein level to modulate the ability of sclerostin to decrease osteoblastic activity.

The term "modulate" or "modulating" means changing, that is increasing or decreasing. Hence, while agents that can decrease SOST expression or sclerostin activity are often used in the compositions and methods of the invention, agents that also increase SOST expression or sclerostin activity are also encompassed within the scope of the invention.

Agents useful for modulating SOST expression and sclerostin activity include, but are not limited to, steroids, alkaloids, terpenoids, peptoids, peptides, nucleic acids, anti-sense nucleic acids and synthetic chemicals. In some embodiments, the SOST antagonist or agonist can bind to a glucocorticoid receptor. For example, dexamethasone tends to abolish the stimulatory effect of BMP-4 and BMP-6 on SOST expression. Other chemical entities including glucocorticoid analogs, bile salts and prostaglandins also modulate the effects of bone morphogenetic proteins on SOST expression.

In one embodiment of the invention, steroids of the formula I can be used for modulating the expression of sclerostin.

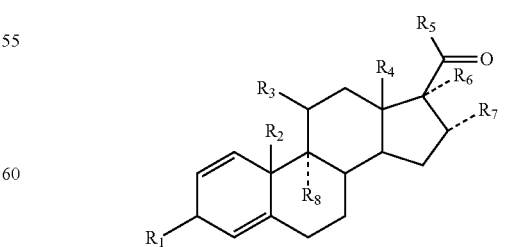

wherein $R_1$, $R_2$, $R_3$, $R_4$, $R_5$, $R_6$, $R_7$, and $R_8$ are separately carbonyl, halo, fluorine, hydrogen, hydroxyl, lower acyl, lower alkoxy, lower alkyl, or lower hydroxy alkyl. Preferred $R_1$, $R_2$, $R_3$, $R_4$, $R_5$, $R_6$, and $R_7$ groups are carbonyl, hydroxy, hydrogen, or lower hydroxy alkyl. Preferably, $R_1$ is carbonyl or hydroxy and $R_2$ is lower alkyl. Also preferably, $R_8$ is a fluorine, hydrogen or halo group.

The following general definitions are used, unless otherwise described: halo is fluoro, chloro, bromo, or iodo. Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Aryloxy means aryl-O—.

More specifically, lower alkyl means ($C_1$-$C_6$) alkyl. Such ($C_1$-$C_6$) alkyl can be methyl, ethyl, propyl, isopropyl, butyl, iso-butyl, sec-butyl, pentyl, 3-pentyl, or hexyl. Lower alkoxy generally means ($C_1$-$C_6$) alkoxy; such ($C_1$-$C_6$) alkoxy can, for example, be methoxy, ethoxy, propoxy, isopropoxy, butoxy, iso-butoxy, sec-butoxy, pentoxy, 3-pentoxy, or hexyloxy. Preferred lower alkyl groups are ($C_1$-$C_3$) alkyl including methyl ethyl, propyl, isopropyl and the like. More preferred lower alkyl groups are methyl. Lower acyl refers to a carbonyl group attached to a lower alkyl group (e.g., —CO—$CH_3$). Lower hydroxy alkyl refers to a hydroxy group attached to a lower alkyl or lower alkylene group (e.g. —$CH_2$—$CH_2$—OH).

One example of an effective SOST/sclerostin antagonist is dexamethasone. Dexamethasone is a synthetic version of the glucocorticoid hormone, cortisol, which has been used as an anti-inflammatory agent. The structure of dexamethasone is provided below.

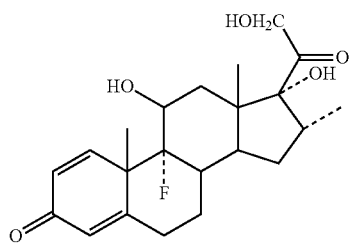

Cortisol and other glucocorticoids and molecules with structures similar to dexamethasone are also contemplated by the invention as antagonists of sclerostin. Androgens and estrogens are also contemplated as antagonists of sclerostin. Other chemical entities including glucocorticoid analogs, bile salts and prostaglandins also modulate the effects of bone morphogenetic proteins on SOST expression.

Exemplary bile salts can have the following structure:

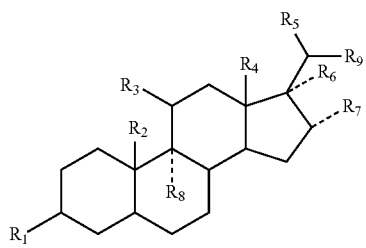

wherein $R_1$, $R_2$, $R_3$, $R_4$, $R_5$, $R_6$, $R_7$, and $R_8$ groups are as described above, and $R_9$ is carbonyl, halo, fluorine, hydrogen, hydroxyl, lower acyl, lower alkoxy, lower alkyl, or lower hydroxy alkyl. Preferably, $R_9$ is hydrogen, hydroxyl, lower acyl, lower alkyl, or lower hydroxy alkyl.

Exemplary prostaglandins or eicosanoids can have the following structure:

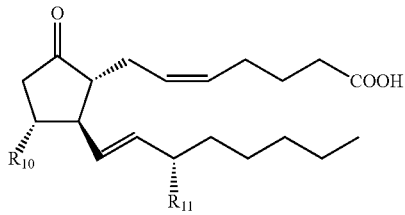

wherein $R_{10}$ and $R_{11}$ are separately carbonyl, halo, fluorine, hydrogen, hydroxyl, lower acyl, lower alkoxy, lower alkyl, lower hydroxy alkyl, aryl or aryloxy.

Compounds or molecules that stimulate the degradation of SOST transcripts or sclerostin can also be used to diminish the levels of sclerostin and enhance bone mineralization.

In another embodiment, the invention provides anti-sense RNA or DNA molecules to modulate SOST expression, sclerostin translation and/or the degradation of SOST transcripts. For example, an anti-sense RNA or DNA that can hybridize to a nucleic acid having any one of SEQ ID NO:1, 2, 4, 5 or 7 can be used as an anti-sense RNA or DNA for diminishing the expression of sclerostin.

The degradation of SOST in RNA may also be increased upon exposure to small duplexes of synthetic double-stranded RNA through the use of RNA interference (siRNA or RNAi) technology (Scherr, M. et al. 2003; Martinez, L. A. et al. 2002). A process is therefore provided for inhibiting expression of a target gene in a cell. The process comprises introduction of RNA with partial or fully double-stranded character into the cell or into the extracellular environment. Inhibition is specific to SOST RNA because a nucleotide sequence from a portion of the SOST gene is chosen to produce inhibitory RNA. This process is effective in producing inhibition of gene expression.

SiRNAs were designed using the guidelines provided by Ambion (Austin, Tex.). Briefly, the SOST cDNA sequence was scanned for target sequences that had AA dinucleotides. Sense and anti-sense oligonucleotides were generated to these targets (AA+3' adjacent 19 nucleotides) that contained a G/C content of 35 to 55%. These sequences were then compared to others in the human genome database to minimize homology to other known coding sequences (Blast search).

The target and siRNA sequences designed are provided below.

```
                                          (SEQ ID NO: 9)
Target sequence 1: AAGAATGATGCCACGGAAATC
Position in gene sequence: 140
GC content: 42.9%
                                          (SEQ ID NO: 10)
Sense strand siRNA: GAAUGAUGCCACGGAAAUCtt
                                          (SEQ ID NO: 11)
Antisense strand siRNA: GAUUUCCGUGGCAUCAUUCtt (SEQ ID NO: 12)
Target sequence 3: AATGATGCCACGGAAATCATC
Position in gene sequence: 143
GC content: 42.9%
                                          (SEQ ID NO: 13)
Sense strand siRNA: UGAUGCCACGGAAAUCAUCtt
                                          (SEQ ID NO: 14)
Antisense strand siRNA: GAUGAUUUCCGUGGCAUCAtt
```

```
                                     (SEQ ID NO: 15)
Target sequence 5: AACAACAAGACCATGAACCGG
Position in gene sequence: 209
GC content: 47.6%
                                     (SEQ ID NO: 16)
Sense strand siRNA: CAACAAGACCAUGAACCGGtt
                                     (SEQ ID NO: 17)
Antisense strand siRNA: CCGGUUCAUGGUCUUGUUGtt (SEQ ID NO: 18)
Target sequence 27: AATTGAGAGTCACAGACACTG
Position in gene sequence: 950
GC content: 42.9%
                                     (SEQ ID NO: 19)
Sense strand siRNA: UUGAGAGUCACAGACACUGtt
                                     (SEQ ID NO: 20)
Antisense strand siRNA: CAGUGUCUGUGACUCUCAAtt (SEQ ID NO: 21)
Target sequence 28: AAATGGAAGCATTTTCACCGC
Position in gene sequence: 1035
GC content: 42.9%
                                     (SEQ ID NO: 22)
Sense strand siRNA: AUGGAAGCAUUUUCACCGCtt
                                     (SEQ ID NO: 23)
Antisense strand siRNA: GCGGUGAAAAUGCUUCCAUtt (SEQ ID NO: 24)
Target sequence 30: AAAGTCCAGGGACTGGTTAAG
Position in gene sequence: 1093
GC content: 47.6%
                                     (SEQ ID NO: 25)
Sense strand siRNA: AGUCCAGGGACUGGUUAAGtt
                                     (SEQ ID NO: 26)
Antisense strand siRNA: CUUAACCAGUCCCUGGACUtt (SEQ ID NO: 27)
Target sequence 31: AAGAAAGTTGGATAAGATTCC
Position in gene sequence: 1111
GC content: 33.3%
                                     (SEQ ID NO: 28)
Sense strand siRNA: GAAAGUUGGAUAAGAUUCCtt
                                     (SEQ ID NO: 29)
Antisense strand siRNA: GGAAUCUUAUCCAACUUUCtt (SEQ ID NO: 30)
Target sequence 36: AACTGTAGATGTGGTTTCTAG
Position in gene sequence: 1201
GC content: 38.1%
                                     (SEQ ID NO: 31)
Sense strand siRNA: CUGUAGAUGUGGUUUCUAGtt
                                     (SEQ ID NO: 32)
Antisense strand siRNA: CUAGAAACCACAUCUACAGtt (SEQ ID NO: 33)
Target sequence 40: AATTCTCCTTCGGGACCTCAA
Position in gene sequence: 1269
GC content: 47.6%
                                     (SEQ ID NO: 34)
Sense strand siRNA: UUCUCCUUCGGGACCUCAAtt
                                     (SEQ ID NO: 35)
Antisense strand siRNA: UUGAGGUCCCGAAGGAGAAtt (SEQ ID NO: 36)
Target sequence 47: AAAGAGAGAGAATGAATGCAG
Position in gene sequence: 1414
GC content: 38.1%
                                     (SEQ ID NO: 37)
Sense strand siRNA: AGAGAGAGAAUGAAUGCAGtt
                                     (SEQ ID NO: 38)
Antisense strand siRNA: CUGCAUUCAUUCUCUCUCUtt (SEQ ID NO: 39)
Target sequence 63: AAGAAGCTATGCTGCTTCCCA
Position in gene sequence: 1590
GC content: 47.6%
                                     (SEQ ID NO: 40)
Sense strand siRNA: GAAGCUAUGCUGCUUCCCAtt
                                     (SEQ ID NO: 41)
Antisense strand siRNA: UGGGAAGCAGCAUAGCUU (SEQ ID NO: 42)
Target sequence 70: AAATCACATCCGCCCCAACTT
Position in gene sequence: 1726
GC content: 47.6%
                                     (SEQ ID NO: 43)
Sense strand siRNA: AUCACAUCCGCCCCAACUUtt
                                     (SEQ ID NO: 44)
Antisense strand siRNA: AAGUUGGGGCGGAUGUGAUtt
```

Hence, the invention provides a pharmaceutical composition that includes a carrier and a siRNA comprising SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, SEQ ID NO:38, SEQ ID NO:41 or SEQ ID NO:44, wherein the siRNA can modulate SOST expression. The invention also provides a pharmaceutical composition comprising a carrier and a siRNA that is selectively hybridizable under stringent conditions to an RNA derived from a DNA comprising SEQ ID NO:9, SEQ ID NO:12, SEQ ID NO:15, SEQ ID NO:18, SEQ ID NO:21, SEQ ID NO:24, SEQ ID NO:27, SEQ ID NO:30, SEQ ID NO:33, SEQ ID NO:36, SEQ ID NO:39, or SEQ ID NO:42, wherein the siRNA can modulate SOST expression.

Mixtures and combinations of such siRNA molecules are also contemplated by the invention. These compositions can used in the methods of the invention, for example, for treating or preventing apoptosis of bone-related cells or for treating or preventing loss of bone density. These compositions are also useful for modulating (e.g. decreasing) SOST expression.

The siRNA provided herein can selectively hybridize to RNA in vivo or in vitro. A nucleic acid sequence is considered to be "selectively hybridizable" to a reference nucleic acid sequence if the two sequences specifically hybridize to one another under physiological conditions or under moderate stringency hybridization and wash conditions. In some embodiments the siRNA is selectively hybridizable to an RNA (e.g. a SOST RNA) under physiological conditions. Hybridization under physiological conditions can be measured as a practical matter by observing interference with the function of the RNA. Alternatively, hybridization under physiological conditions can be detected in vitro by testing for siRNA hybridization using the temperature (e.g. 37° C.) and salt conditions that exist in vivo.

Moreover, as an initial matter, other in vitro hybridization conditions can be utilized to characterize siRNA interactions. Exemplary in vitro conditions include hybridization conducted as described in the Bio-Rad Labs ZetaProbe manual (Bio-Rad Labs, Hercules, Calif.); Sambrook et al., *Molecular Cloning: A Laboratory Manual,* 2nd ed., Cold Spring Harbor Laboratory Press, (1989), or Sambrook et al., *Molecular Cloning: A Laboratory Manual,* 3rd ed., Cold Spring Harbor Laboratory Press, (2001)), expressly incorporated by reference herein. For example, hybridization can be conducted in 1 mM EDTA, 0.25 M $Na_2 HPO_4$ and 7% SDS at 42° C., followed by washing at 42° C. in 1 mM EDTA, 40 mM $NaPO_4$, 5% SDS, and 1 mM EDTA, 40 mM $NaPO_4$, 1% SDS. Hybridization can also be conducted in 1 mM EDTA, 0.25 M $Na_2 HPO_4$ and 7% SDS at 60° C., followed by washing in 1 mM EDTA, 40 mM $NaPO_4$, 5% SDS, and 1 mM EDTA, 40 mM $NaPO_4$, 1% SDS. Washing can also be conducted at other temperatures, including temperatures ranging from 37° C. to at 65° C., from 42° C. to at 65° C., from 37° C. to at 60° C., from 50° C. to at 65° C., from 37° C. to at 55° C., and other such temperatures.

The siRNA employed in the compositions and methods of the invention may be synthesized either in vivo or in vitro. In some embodiments, the siRNA molecules are synthesized in vitro using methods, reagents and synthesizer equipment available to one of skill in the art. Endogenous RNA polymerases within a cell may mediate transcription in vivo, or cloned RNA polymerase can be used for transcription in vivo or in vitro. For transcription from a transgene or an expression construct in vivo, a regulatory region may be used to transcribe the siRNA strands.

Depending on the particular sequence utilized and the dose of double stranded siRNA material delivered, the compositions and methods may provide partial or complete loss of function for the target gene (SOST). A reduction or loss of gene expression in at least 99% of targeted cells has been shown for other genes. See, e.g., U.S. Pat. No. 6,506,559. Lower doses of injected material and longer times after administration of the selected siRNA may result in inhibition in a smaller fraction of cells.

The siRNA may comprise one or more strands of polymerized ribonucleotide; it may include modifications to either the phosphate-sugar backbone or the nucleoside. The double-stranded siRNA structure may be formed by a single self-complementary RNA strand or two complementary RNA strands. siRNA duplex formation may be initiated either inside or outside the cell. The siRNA may be introduced in an amount that allows delivery of at least one copy per cell. Higher doses of double-stranded material may yield more effective inhibition.

Inhibition is sequence-specific in that nucleotide sequences corresponding to the duplex region of the RNA are targeted for genetic inhibition. siRNA containing nucleotide sequences identical to a portion of the target gene is preferred for inhibition. However, siRNA sequences with insertions, deletions, and single point mutations relative to the target sequence have also been found to be effective for inhibition. Thus, sequence identity may optimized by alignment algorithms known in the art and calculating the percent difference between the nucleotide sequences. Alternatively, the duplex region of the RNA may be defined functionally as a nucleotide sequence that is capable of hybridizing with a portion of the target gene transcript.

The siRNA may be directly introduced into the cell (i.e., intracellularly); or introduced extracellularly into a cavity, interstitial space, into the circulation of an organism, introduced orally, or may be introduced by bathing an organism in a solution containing siRNA. Methods for oral introduction include direct mixing of siRNA with food of the organism, as well as engineered approaches in which a species that is used as food is engineered to express an siRNA, then fed to the organism to be affected. Physical methods of introducing nucleic acids include injection directly into the cell or extracellular injection into the organism of an siRNA solution.

The siRNA may also be delivered in vitro to cultured cells using transfection agents available in the art such as lipofectamine or by employing viral delivery vectors such as those from lentiviruses. Such in vitro delivery can be performed for testing purposes or for therapeutic purposes. For example, cells from a patient can be treated in vitro and then re-administered to the patient.

The advantages of using siRNA include: the ease of introducing double-stranded siRNA into cells, the low concentration of siRNA that can be used, the stability of double-stranded siRNA, and the effectiveness of the inhibition. The ability to use a low concentration of a naturally-occurring nucleic acid avoids several disadvantages of anti-sense interference.

An antagonist or agonist for sclerostin may also be a co-factor, such as a protein, peptide, carbohydrate, lipid or small molecular weight molecule, which interacts with sclerostin to regulate its activity. Other molecules contemplated as agents for modulating sclerostin include antibodies targeted against sclerostin as well as molecules, compounds or peptides that mimic bone morphogenetic proteins in structure and that bind to and form inactive complexes with sclerostin. Potential polypeptide antagonists include antibodies that react with sclerostin.

As described herein, sclerostin is involved in controlling formation of mature osteoblasts, the primary cell type implicated in bone mineralization. A decrease in the rate of bone mineralization can lead to various bone disorders collectively referred to as osteopenias, including bone disorders such as osteoporosis, osteomyelitis, hypercalcemia, osteopenia brought on by surgery or steroid administration, Paget's disease, osteonecrosis, bone loss due to rheumatoid arthritis; periodontal bone loss, immobilization, prosthetic loosing and osteolytic metastasis.

According to the invention, agents that modulate the function of sclerostin, or that modulate the expression of SOST, can be used to treat any of these diseases. Preferably, SOST/sclerostin antagonists or agents that decrease the function of SOST or sclerostin are used to treat osteoporosis, frail bone problems and related diseases where bone density is inadequate.

Conversely, an increase in bone mineralization can lead to osteopetrosis, a condition marked by excessive bone density. According to the invention, sclerostin may be used to treat conditions characterized by excessive bone density. The most common condition is osteopetrosis in which a genetic defect results in elevated bone mass and is usually fatal in the first few years of life. Osteopetrosis is preferably treated by administration of sclerostin.

The therapeutic methods for treating or preventing a bone disorder such as an inadequate rate of bone mineralization involve administering an agent that can modulate SOST (e.g. a SOST antagonist) to a mammal affected with the bone disorder. Any of the agents or antagonists described herein, or isolated by the methods provided herein, can be administered. Any bone disorder involving diminished mineralization can be treated or prevented using these methods.

The therapeutic methods for treating or preventing a bone disorder such as an excessive bone density involve administering a therapeutically effective amount of sclerostin to a mammal affected with the bone disorder. Any of the available mammalian sclerostin polypeptides (for example, those described herein) can be administered for treating or preventing excessive bone density.

Methods of Isolating Agents that can Modulate SOST/Sclerostin

The invention further provides screening assays that are useful for generating or identifying therapeutic agents for the treatment of bone disorders. In particular, the SOST nucleic acids and sclerostin proteins identified herein may be used in a variety of assays for detecting SOST and/or sclerostin and for identifying factors that interact with SOST nucleic acids or with the sclerostin protein.

In general, an assay for identifying sclerostin involves incubating a test sample tinder conditions which permit binding of sclerostin to a reporter molecule, and measuring the extent of binding. A reporter molecule can be any molecule that stably binds to sclerostin and that can be detected. For example, the reporter molecule can be an anti-sclerostin antibody that is labeled with radioactive isotopes ($^{125}$I, $^{32}$P, $^{35}$S, $^{3}$H), fluorescent dyes (fluorescein, rhodamine), enzymes and the like. It is understood that the choice of a reporter molecule will depend upon the detection system used.

Sclerostin may be purified or present in mixtures, such as in cultured cells, tissue samples, body fluids or culture medium. Assays may be developed that are qualitative or quantitative, with the latter being useful for determining the binding parameters (affinity constants and kinetics) of the reporter molecule to sclerostin and for quantifying levels of sclerostin in mixtures. Assays may also be used to detect fragments, analogs and derivatives of sclerostin and to identify new sclerostin family members.

Binding assays may be carried out in several formats, including cell-based binding assays, solution-phase assays and immunoassays. In general, test samples or compounds are incubated with sclerostin test samples for a specified period of time followed by measurement of the reporter molecule by use of microscopy, fluorimetry, a scintillation counter, or any available immunoassay. Binding can also be detected by labeling sclerostin in a competitive radioimmunoassay. Alternatively, sclerostin may be modified with an unlabeled epitope tag (e.g., biotin, peptides, $His_6$, FLAG, myc etc.) and bound to proteins such as streptavidin, anti-peptide or anti-protein antibodies that have a detectable label as described above. Additional forms of sclerostin containing epitope tags may be used in solution and immunoassays.

Methods for identifying compounds or molecules that interact with sclerostin are also encompassed by the invention. In general, an assay for identifying compounds or molecules that interact with sclerostin involves incubating sclerostin with a test sample that may contain such a compound or molecule under conditions that permit binding of the compound or molecule to sclerostin, and measuring whether binding has occurred. Sclerostin may be purified or present in mixtures, such as in cultured cells, tissue samples, body fluids or culture medium. Assays may be developed that are qualitative or quantitative. Quantitative assays can used for determining the binding parameters affinity constants and kinetics) of the compound or molecule for sclerostin and for quantifying levels of biologically active compounds and molecules in mixtures. Assays may also be used to evaluate the binding of a compound or molecule to fragments, analogs and derivatives of sclerostin and to identify new sclerostin family members.

The compound or molecule in a test sample may be substantially purified or present in a crude mixture. Binding compounds and molecules may be nucleic acids, proteins, peptides, carbohydrates, lipids or small molecular weight organic compounds. The compounds and molecules may be further characterized by their ability to increase or decrease sclerostin activity in order to determine whether they act as an agonist or an antagonist.

In another embodiment, the invention involves a method for identifying an agent that can modulate sclerostin-related apoptosis activity comprising contacting a cell with both sclerostin and a test agent and detecting whether the test sample prevents apoptosis of the cell. The amount of apoptosis in cells treated with sclerostin and a test agent can be compared to the amount of apoptosis in cells treated with sclerostin only. To detect the level of apoptosis, cell viability and apoptosis assays can be performed. Many cell viability assays are available to one of skill in the art and any of these can be used. For example, a CellTiterGlo Luminescence Viability Assay available from Promega can be used to assess cell viability. Apoptosis can be detected using any of the many available apoptosis assays. For example, the Homogeneous Caspase ELISA (Roche) or the Cell Death assay (Histone-Associated DNA Fragmentation, Roche) can be used. Apoptosis can also be detected by TUNEL staining using Roche's In Situ Cell Death Detection kit.

SOST nucleic acids are also useful for identification of factors that interact with the SOST promoter and that modulate SOST expression. Such factors may be intracellular proteins such as DNA binding proteins that interact with regulatory sequences that control SOST transcription, for example, the SOST promoter. As an example, hybrid constructs may be used that include a nucleic acid encoding the SOST promoter fused to a nucleic acid encoding a marker protein. The SOST promoter can be found within SEQ ID NO:1. The promoter used can, for example, have sequence SEQ NO:4.

The marker protein can be any marker protein available to one of skill in the art. For example, the marker protein can be luciferase, green fluorescence protein (GFP) or CAT.

Such constructs are used for in vitro or in vivo transcription assays to identify factors that modulate SOST expression. Factors that depress or diminish SOST expression are particularly useful. Expression or transcription levels can be assessed using any method available to one of skill in the art for measuring RNA levels. For example, RNA levels can be assessed by northern analysis, reverse transcriptase analysis, reverse transcriptase coupled with polymerase chain reaction (RT-PCR) analysis and other methods. Chemical libraries can be screened using such methods for small molecule compounds that block SOST transcription.

Sclerostin is involved in controlling formation of mature osteoblasts, the primary cell type implicated in bone mineralization. Factors that counteract the sclerostin-induced depression of mineralization can be identified by observing whether a test agent increases mineralization in cultured osteoblasts that have been exposed to sclerostin. Hence, an assay may involve contacting an osteoblast with sclerostin and a test agent and observing whether the mineralization of the cell is increased relative to a similar cell that is contacted only with sclerostin.

Many variations and modifications of the methods described herein will be apparent to one of skilled in the art. All such variations and modifications are encompassed by the invention.

Antibodies

The invention provides antibody preparations directed against sclerostin, for example, antibodies capable of binding a polypeptide having SEQ ID NO:3, SEQ ID NO:6 or SEQ ID NO:8.

Antibody molecules belong to a family of plasma proteins called immunoglobulins, whose basic building block, the immunoglobulin fold or domain, is used in various forms in many molecules of the immune system and other biological recognition systems. A typical immunoglobulin has four polypeptide chains, containing an antigen binding region known as a variable region and a non-varying region known as the constant region.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al., J. Mol. Biol. 186, 651-66, 1985); Novotny and Haber, Proc. Natl. Acad. Sci. USA 82, 4592-4596 (1985).

Depending on the amino acid sequences of the constant domain of their heavy chains, immunoglobulins can be assigned to different classes. There are at least five (5) major classes of immunoglobulins: IgA, IgD, IgE, IgG and IgM, and several of these may be further divided into subclasses (isotypes), e.g. IgG-1, IgG-2, IgG-3 and IgG-4; IgA-1 and IgA-2. The heavy chains constant domains that correspond to the different classes of immunoglobulins are called alpha ($\alpha$), delta ($\delta$), epsilon ($\epsilon$), gamma ($\gamma$) and mu ($\mu$), respectively. The light chains of antibodies can be assigned to one of two clearly distinct types, called kappa ($\kappa$) and lambda ($\lambda$) based on the amino sequences of their constant domain. The subunit structures and three-dimensional configurations of different classes of immunoglobulins are well known.

The term "variable" in the context of variable domain of antibodies, refers to the fact that certain portions of the variable domains differ extensively in sequence among antibodies. The variable domains are for binding and determine the specificity of each particular antibody for its particular antigen. However, the variability is not evenly distributed through the variable domains of antibodies. It is concentrated in three segments called complementarity determining regions (CDRs) also known as hypervariable regions both in the light chain and the heavy chain variable domains.

The more highly conserved portions of variable domains are called the framework (FR). The variable domains of native heavy and light chains each comprise four FR regions, largely adopting a $\beta$-sheet configuration, connected by three CDRs, which form loops connecting, and in some cases forming part of, the $\beta$-sheet structure. The CDRs in each chain are held together in close proximity by the FR regions and, with the CDRs from the other chain, contribute to the formation of the antigen-binding site of antibodies. The constant domains are not involved directly in binding an antibody to an antigen, but exhibit various effector functions, such as participation of the antibody in antibody-dependent cellular toxicity.

An antibody that is contemplated for use in the present invention thus can be in any of a variety of forms, including a whole immunoglobulin, an antibody fragment such as Fv, Fab, and similar fragments, a single chain antibody which includes the variable domain complementarity determining regions (CDR), and the like forms, all of which fall under the broad term "antibody", as used herein. The present invention contemplates the use of any specificity of an antibody, polyclonal or monoclonal, and is not limited to antibodies that recognize and immunoreact with a specific antigen. In preferred embodiments, in the context of both the therapeutic and screening methods described below, an antibody or fragment thereof is used that is immunospecific for an antigen or epitope of the invention.

The term "antibody fragment" refers to a portion of a full-length antibody, generally the antigen binding or variable region. Examples of antibody fragments include Fab, Fab', F(ab')$_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an F(ab')$_2$ fragment that has two antigen binding fragments that are capable of cross-linking antigen, and a residual other fragment (which is termed pFc'). Additional fragments can include diabodies, linear antibodies, single-chain antibody molecules, and multispecific antibodies formed from antibody fragments. As used herein, "functional fragment" with respect to antibodies, refers to Fv, F(ab) and F(ab')$_2$ fragments.

Antibody fragments contemplated by the invention are therefore not full-length antibodies but do have similar or improved immunological properties relative to an anti-sclerostin antibody. Such antibody fragments may be as small as about 4 amino acids, 5 amino acids, 6 amino acids, 7 amino acids, 9 amino acids, about 12 amino acids, about 15 amino acids, about 17 amino acids, about 18 amino acids, about 20 amino acids, about 25 amino acids, about 30 amino acids or more. In general, an antibody fragment of the invention can have any upper size limit so long as it binds with specificity to sclerostin, e.g. a polypeptide having SEQ ID NO:3, 6 or 8.

Antibody fragments retain some ability to selectively bind with its antigen. Some types of antibody fragments are defined as follows:

(1) Fab is the fragment that contains a monovalent antigen-binding fragment of an antibody molecule. A Fab fragment can be produced by digestion of whole antibody with the enzyme papain to yield an intact light chain and a portion of one heavy chain.

(2) Fab' is the fragment of an antibody molecule can be obtained by treating whole antibody with pepsin, followed by reduction, to yield an intact light chain and a portion of the heavy chain. Two Fab' fragments are obtained per antibody molecule. Fab' fragments differ from Fab fragments by the addition of a few residues at the carboxyl terminus of the heavy chain CH1 domain including one or more cysteines from the antibody hinge region.

(3) (Fab')$_2$ is the fragment of an antibody that can be obtained by treating whole antibody with the enzyme pepsin without subsequent reduction. F(ab')$_2$ is a dimer of two Fab' fragments held together by two disulfide bonds.

(4) Fv is the minimum antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

(5) Single chain antibody ("SCA"), defined as a genetically engineered molecule containing the variable region of the light chain, the variable region of the heavy chain, linked by a suitable polypeptide linker as a genetically fused single chain molecule. Such single chain antibodies are also referred to as "single-chain Fv" or "sFv" antibody fragments. Generally, the Fv polypeptide further comprises a polypeptide linker between the VH and VL domains that enables the sFv to form the desired structure for antigen binding. For a review of sFv see Pluckthun in The Pharmacology of Monoclonal Antibodies, vol. 113, Rosenburg and Moore eds. Springer-Verlag, N.Y., pp. 269-315 (1994).

The term "diabodies" refers to a small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161, and Hollinger et al., Proc. Natl. Acad. Sci. USA 90: 6444-6448 (1993).

Methods for preparing polyclonal antibodies are available to those skilled in the art. See, for example, Green, et al., Production of Polyclonal Antisera, in: *Immunochemical Protocols* (Manson, ed.), pages 1-5 (Humana Press); Coligan, et al., Production of Polyclonal Antisera in Rabbits, Rats Mice and Hamsters, in: *Current Protocols in Immunology*, section 2.4.1 (1992), which are hereby incorporated by reference.

Methods for preparing monoclonal antibodies are likewise available to one of skill in the art. See, for example, Kohler & Milstein, Nature, 256:495 (1975); Coligan, et al., sections 2.5.1-2.6.7; and Harlow, et al., in: *Antibodies: A Laboratory Manual*, page 726 (Cold Spring Harbor Pub. (1988)), which are hereby incorporated by reference. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan, et al., sections 2.7.1-2.7.12 and sections 2.9.1-2.9.3; Barnes, et al., Purification of Immunoglobulin G (IgG), in: *Methods in Molecular Biology*, Vol. 10, pages 79-104 (Humana Press (1992).

Methods of in vitro and in vivo manipulation of monoclonal antibodies are also available to those skilled in the art. For example, monoclonal antibodies to be used in accordance with the present invention may be made by the hybridoma method first described by Kohler and Milstein, Nature 256, 495 (1975), or may be made by recombinant methods, e.g., as described in U.S. Pat. No. 4,816,567. The monoclonal antibodies for use with the present invention may also be isolated from phage antibody libraries using the techniques described in Clackson et al. Nature 352: 624-628 (1991), as well as in Marks et al., J. Mol Biol. 222: 581-597 (1991). Another method involves humanizing a monoclonal antibody by recombinant means to generate antibodies containing human specific and recognizable sequences. See, for review, Holmes, et al., J. Immunol., 158:2192-2201 (1997) and Vaswani, et al., Annals Allergy, Asthma & Immunol., 81:105-115 (1998).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional polyclonal antibody preparations that typically include different antibodies directed against different determinants (epitopes), each monoclonal antibody is directed against a single determinant on the antigen. In additional to their specificity, the monoclonal antibodies are advantageous in that they are synthesized by the hybridoma culture, uncontaminated by other immunoglobulins. The modifier "monoclonal" indicates that the antibody preparation is a substantially homogeneous population of antibodies, and is not to be construed as requiring production of the antibody by any particular method.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567); Morrison et al. Proc. Natl. Acad. Sci. 81, 6851-6855 (1984).

Methods of making antibody fragments are also known in the art (see for example, Harlow and Lane, *Antibodies: A Laboratory Manual*, Cold Spring Harbor Laboratory, New York, (1988), incorporated herein by reference). Antibody fragments of the present invention can be prepared by proteolytic hydrolysis of the antibody or by expression in *E. coli* of DNA encoding the fragment. Antibody fragments can be obtained by pepsin or papain digestion of whole antibodies conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, in U.S. Pat. No. 4,036,945 and No. 4,331,647, and references contained therein. These patents are hereby incorporated in their entireties by reference.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. For example, Fv fragments comprise an association of $V_H$ and $V_L$ chains. This association may be non-covalent or the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the and $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow, et al., *Methods: a Companion to Methods in Enzymology*, Vol. 2, page 97 (1991); Bird, et al., Science 242:423-426 (1988); Ladner, et al, U.S. Pat. No. 4,946,778; and Pack, et al., *Bio/Technology* 11:1271-77 (1993).

Another form of an antibody fragment is a peptide coding for a single complementarity-determining region (CDR). CDR peptides ("minimal recognition units") are often involved in antigen recognition and binding. CDR peptides can be obtained by cloning or constructing genes encoding the CDR of an antibody of interest. Such genes are prepared, for example, by using the polymerase chain reaction to synthesize the variable region from RNA of antibody-producing cells. See, for example, Larrick, et al., *Methods: a Companion to Methods in Enzymology*, Vol. 2, page 106 (1991).

The invention contemplates human and humanized forms of non-human (e.g. murine) antibodies. Such humanized antibodies are chimeric immunoglobulins, immunoglobulin chains or fragments thereof (such as Fv, Fab, Fab', $F(ab')_2$, or other antigen-binding subsequences of antibodies) that contain minimal sequence derived from non-human immunoglobulin. For the most part, humanized antibodies are human immunoglobulins (recipient antibody) in which residues from a complementary determining region (CDR) of the recipient are replaced by residues from a CDR of a nonhuman species (donor antibody) such as mouse, rat or rabbit having the desired specificity, affinity and capacity.

In some instances, Fv framework residues of the human immunoglobulin are replaced by corresponding non-human residues. Furthermore, humanized antibodies may comprise residues that are found neither in the recipient antibody nor in the imported CDR or framework sequences. These modifications are made to further refine and optimize antibody performance. In general, humanized antibodies will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details, see: Jones et al., Nature 321, 522-525 (1986); Reichmann et al., Nature 332, 323-329 (1988); Presta, Curr. Op. Struct. Biol. 2, 593-596 (1992); Holmes, et al., J. Immunol., 158:2192-2201 (1997) and Vaswani, et al., Annals Allergy, Asthma & Immunol., 81:105-115 (1998).

The invention also provides methods of mutating antibodies to optimize their affinity, selectivity, binding strength or other desirable property. A mutant antibody refers to an amino acid sequence variant of an antibody. In general, one or more of the amino acid residues in the mutant antibody is different from what is present in the reference antibody. Such mutant antibodies necessarily have less than 100% sequence identity or similarity with the reference amino acid sequence. In general, mutant antibodies have at least 75% amino acid sequence identity or similarity with the amino acid sequence of either the heavy or light chain variable domain of the reference antibody. Preferably, mutant antibodies have at least 80%, more preferably at least 85%, even more preferably at least 90%, and most preferably at least 95% amino acid sequence identity or similarity with the amino acid sequence of either the heavy or light chain variable domain of the reference antibody. One method of mutating antibodies involves affinity maturation using phage display.

The invention is therefore directed to a method for selecting antibodies and/or antibody fragments or antibody polypeptides with desirable properties. Such desirable properties can include increased binding affinity or selectivity for the epitopes of the invention The antibodies and antibody fragments of the invention are isolated antibodies and antibody fragments. An isolated antibody is one that has been identified and separated and/or recovered from a component of the environment in which it was produced. Contaminant components of its production environment are materials that would interfere with diagnostic or therapeutic uses for the antibody, and may include enzymes, hormones, and other proteinaceous or nonproteinaceous solutes. The term "isolated antibody" also includes antibodies within recombinant cells because at least one component of the antibody's natural environment will not be present. Ordinarily, however, isolated antibody will be prepared by at least one purification step If desired, the antibodies of the invention can be purified by any available procedure. For example, the antibodies can be affinity purified by binding an antibody preparation to a solid support to which the antigen used to raise the antibodies is bound. After washing off contaminants, the antibody can be eluted by known procedures. Those of skill in the art will know of various techniques common in the immunology arts for purification and/or concentration of polyclonal antibodies, as well as monoclonal antibodies (see for example, Coligan, et al., Unit 9, *Current Protocols in Immunology*, Wiley Interscience, 1991, incorporated by reference).

In preferred embodiments, the antibody will be purified as measurable by at least three different methods: 1) to greater than 95% by weight of antibody as determined by the Lowry method, and most preferably more than 99% by weight; 2) to a degree sufficient to obtain at least 15 residues of N-terminal or internal amino acid sequence by use of a spinning cup sequenator; or 3) to homogeneity by SDS-PAGE under reducing or non-reducing conditions using Coomasie blue or, preferably, silver stain.

Compositions

The sclerostin antagonists and other agents (e.g. sclerostin proteins and SOST nucleic acids) of the invention, including their salts, are administered so as to achieve a reduction in at least one symptom associated with a bone disorder, indication or disease.

To achieve the desired effect(s), sclerostin antagonists and other agents, may be administered as single or divided dosages, for example, of at least about 0.01 mg/kg to about 500 to 750 mg/kg, of at least about 0.01 mg/kg to about 300 to 500 mg/kg, at least about 0.1 mg/kg to about 100 to 300 mg/kg or at least about 1 mg/kg to about 50 to 100 mg/kg of body weight, although other dosages may provide beneficial results. The amount administered will vary depending on various factors including, but not limited to, the sclerostin antagonist or other agent chosen, the disease, the weight, the physical condition, the health, the age of the mammal, whether prevention or treatment is to be achieved, and if the sclerostin antagonist or agent is chemically modified. Such factors can be readily determined by the clinician employing animal models or other test systems that are available in the art.

Administration of the therapeutic agents in accordance with the present invention may be in a single dose, in multiple doses, in a continuous or intermittent manner, depending, for example, upon the recipient's physiological condition, whether the purpose of the administration is therapeutic or prophylactic, and other factors known to skilled practitioners. The administration of the therapeutic agents of the invention may be essentially continuous over a preselected period of time or may be in a series of spaced doses. Both local and systemic administration is contemplated.

To prepare the composition, therapeutic agents are synthesized or otherwise obtained, purified as necessary or desired and then lyophilized and stabilized. The therapeutic agent can then be adjusted to the appropriate concentration, and optionally combined with other agents. The absolute weight of a given therapeutic agent included in a unit dose can vary widely. For example, about 0.01 to about 2 g, or about 0.1 to about 500 mg, of at least one therapeutic agents of the invention, or a plurality of therapeutic agents can be administered. Alternatively, the unit dosage can vary from about 0.01 g to about 50 g, from about 0.01 g to about 35 g, from about 0.1 g to about 25 g, from about 0.5 g to about 12 g, from about 0.5 g to about 8 g, from about 0.5 g to about 4 g, or from about 0.5 g to about 2 g.

Daily doses of the therapeutic agents of the invention can vary as well. Such daily doses can range, for example, from about 0.1 g/day to about 50 g/day, from about 0.1 g/day to about 25 g/day, from about 0.1 g/day to about 12 g/day, from about 0.5 g/day to about 8 g/day, from about 0.5 g/day to about 4 g/day, and from about 0.5 g/day to about 2 g/day.

Thus, one or more suitable unit dosage forms comprising the therapeutic agents of the invention can be administered by a variety of routes including oral, parenteral (including subcutaneous, intravenous, intramuscular and intraperitoneal), rectal, dermal, transdermal, intrathoracic, intrapulmonary and intranasal (respiratory) routes. The therapeutic agents may also be formulated for sustained release (for example, using microencapsulation, see WO 94/07529, and U.S. Pat. No. 4,962,091). The formulations may, where appropriate, be conveniently presented in discrete unit dosage forms and may be prepared by any of the methods well known to the pharmaceutical arts. Such methods may include the step of mixing the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for oral administration, they are generally combined with a pharmaceutically acceptable carrier, diluent or excipient to form a pharmaceutical formulation, or unit dosage form. For oral administration, the therapeutic agents may be present as a powder, a granular formulation, a solution, a suspension, an emulsion or in a natural or synthetic polymer or resin for ingestion of the active ingredients from a chewing gum. The therapeutic agents may also be presented as a bolus, electuary or paste. Orally administered therapeutic agents of the invention can also be formulated for sustained release, e.g., the therapeutic agents can be coated, micro-encapsulated, or otherwise placed within a sustained delivery device. The total active ingredients in such formulations comprise from 0.1 to 99.9% by weight of the formulation.

By "pharmaceutically acceptable" it is meant a carrier, diluent, excipient, and/or salt that is compatible with the other ingredients of the formulation, and not deleterious to the recipient thereof.

Pharmaceutical formulations containing the therapeutic agents of the invention can be prepared by procedures known in the art using well-known and readily available ingredients. For example, the therapeutic agent can be formulated with common excipients, diluents, or carriers, and formed into tablets, capsules, solutions, suspensions, powders, aerosols and the like. Examples of excipients, diluents, and carriers that are suitable for such formulations include buffers, as well as fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatin, and polyvinyl-pyrrolidone. Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface-active agents such as cetyl alcohol and glycerol monostearate can be included. Adsorptive carriers such as kaolin and bentonite can be added. Lubricants such as talc, calcium and magnesium stearate, and solid polyethyl glycols can also be included. Preservatives may also be added. The compositions of the invention can also contain thickening agents such as cellulose and/or cellulose derivatives. They may also contain gums such as xanthan, guar or carbo gum or gum arabic, or alternatively polyethylene glycols, bentones and montmorillonites, and the like.

For example, tablets or caplets containing the therapeutic agents of the invention can include buffering agents such as calcium carbonate, magnesium oxide and magnesium carbonate. Caplets and tablets can also include inactive ingredients such as cellulose, pre-gelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and the like. Hard or soft gelatin capsules containing at least one therapeutic agent of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric-coated caplets or tablets containing one or more therapeutic agent of the invention are designed to resist disintegration in the stomach and dissolve in the more neutral to alkaline environment of the duodenum.

The therapeutic agents of the invention can also be formulated as elixirs or solutions for convenient oral administration or as solutions appropriate for parenteral administration, for instance by intramuscular, subcutaneous, intraperitoneal or intravenous routes. The pharmaceutical formulations of the therapeutic agents of the invention can also take the form of an aqueous or anhydrous solution or dispersion, or alternatively the form of an emulsion or suspension or salve.

Thus, the therapeutic agents may be formulated for parenteral administration (e.g., by injection, for example, bolus injection or continuous infusion) and may be presented in unit dose form in ampoules, pre-filled syringes, small volume infusion containers or in multi-dose containers. As noted above, preservatives can be added to help maintain the shelve life of the dosage form. The therapeutic agents and other ingredients may form suspensions, solutions, or emulsions in oily or aqueous vehicles, and may contain formulatory agents such as suspending, stabilizing and/or dispersing agents. Alternatively, the therapeutic agents and other ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable carriers, vehicles and adjuvants that are well known in the art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol," polyglycols and polyethylene glycols, $C_1$-$C_4$ alkyl esters of short-chain acids, ethyl or isopropyl lactate, fatty acid triglycerides such as the products marketed under the name "Miglyol," isopropyl myristate, animal, mineral and vegetable oils and polysiloxanes.

It is possible to add, if necessary, an adjuvant chosen from antioxidants, surfactants, other preservatives, film-forming, keratolytic or comedolytic agents, perfumes, flavorings and colorings. Antioxidants such as t-butylhydroquinone, butylated hydroxyanisole, butylated hydroxytoluene and α-tocopherol and its derivatives can be added.

Also contemplated are combination products that include one or more of the therapeutic agents of the present invention and one or more other ingredients. For example, the compositions can contain vitamins, minerals (e.g. calcium), anti-inflammatory agents and the like.

Additionally, the therapeutic agents are well suited to formulation as sustained release dosage forms and the like. The formulations can be so constituted that they release the therapeutic agents, for example, in a particular part of the intestinal or respiratory tract, possibly over a period of time. Coatings, envelopes, and protective matrices may be made, for example, from polymeric substances, such as polylactideglycolates, liposomes, microemulsions, microparticles, nanoparticles, or waxes. These coatings, envelopes, and protective matrices are useful to coat indwelling devices, e.g., tissue re-modeling devices, pins, splints, joint replacement devices and the like.

For topical administration, the therapeutic agents may be formulated as is known in the art for direct application to a target area. Forms chiefly conditioned for topical application take the form, for example, of creams, milks, gels, dispersion or microemulsions, lotions thickened to a greater or lesser extent, impregnated pads, ointments or sticks, aerosol formulations (e.g., sprays or foams), soaps, detergents, lotions or cakes of soap. Other conventional forms for this purpose include wound dressings, coated bandages or other polymer coverings, ointments, creams, lotions, pastes, jellies, sprays, and aerosols. Thus, the therapeutic agents of the invention can be delivered via patches or bandages for dermal administration. Alternatively, the therapeutic agent can be formulated to be part of an adhesive polymer, such as polyacrylate or acrylate/vinyl acetate copolymer. For long-term applications it might be desirable to use microporous and/or breathable backing laminates, so hydration or maceration of the skin can be minimized. The backing layer can be any appropriate thickness that will provide the desired protective and support functions. A suitable thickness will generally be from about 10 to about 200 microns.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The therapeutic agents can also be delivered via iontophoresis, e.g., as disclosed in U.S. Pat. No. 4,140,122; 4,383,529; or 4,051,842. The percent by weight of a therapeutic agent of the invention present in a topical formulation will depend on various factors, but generally will be from 0.01% to 95% of the total weight of the formulation, and typically 0.1-85% by weight.

Drops, such as eye drops or nose drops, may be formulated with one or more of the therapeutic agents in an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The therapeutic agents may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia.

The pharmaceutical formulations of the present invention may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the carriers and/or diluents that are useful in the pharmaceutical formulations of the present invention include water and physiologically acceptable buffered saline solutions such as phosphate buffered saline solutions pH 7.0-8.0.

The therapeutic agents of the invention can also be administered to the respiratory tract. Thus, the present invention also provides aerosol pharmaceutical formulations and dosage forms for use in the methods of the invention. In general, such dosage forms comprise an amount of at least one of the agents of the invention effective to treat or prevent the clinical symptoms of a specific bone disorder or disease. Any statistically significant attenuation of one or more symptoms of the disorder or disease that has been treated pursuant to the method of the present invention is considered to be a treatment of such disorder or disease within the scope of the invention.

Alternatively, for administration by inhalation or insufflation, the composition may take the form of a dry powder, for example, a powder mix of the therapeutic agent and a suitable powder base such as lactose or starch. The powder composition may be presented in unit dosage Ruin in, for example, capsules or cartridges, or, e.g., gelatin or blister packs from which the powder may be administered with the aid of an inhalator, insufflator, or a metered-dose inhaler (see, for example, the pressurized metered dose inhaler (MDI) and the dry powder inhaler disclosed in Newman, S. P. in *Aerosols and the Lung*, Clarke, S. W. and Davia, D. eds., pp. 197-224, Butterworths, London, England, 1984).

Therapeutic agents of the present invention can also be administered in an aqueous solution when administered in an aerosol or inhaled form. Thus, other aerosol pharmaceutical formulations may comprise, for example, a physiologically acceptable buffered saline solution containing between about 0.1 mg/ml and about 100 mg/ml of one or more of the therapeutic agents of the present invention specific for the indication or disease to be treated. Dry aerosol in the form of finely divided solid particles that are not dissolved or suspended in a liquid are also useful in the practice of the present invention. Therapeutic agents of the present invention may be formulated as dusting powders and comprise finely divided particles having an average particle size of between about 1 and 5 µm, alternatively between 2 and 3 µm. Finely divided particles may be prepared by pulverization and screen filtration using techniques well known in the art. The particles may be administered by inhaling a predetermined quantity of the finely divided material, which can be in the form of a powder. It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

For administration to the upper (nasal) or lower respiratory tract by inhalation, the therapeutic agents of the invention are conveniently delivered from a nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Nebulizers include, but are not limited to, those described in U.S. Pat. Nos. 4,624,251; 3,703,173; 3,561,444; and 4,635,627. Aerosol delivery systems of the type disclosed herein are available from numerous commercial sources including Fisons Corporation (Bedford, Mass.), Schering Corp. (Kenilworth, N.J.) and American Pharmoseal Co., (Valencia, Calif.). For intra-nasal administration, the therapeutic agent may also be administered via nose drops, a liquid spray, such as via a plastic bottle atomizer or metered-dose inhaler. Typical of atomizers are the Mistometer (Wintrop) and the Medihaler (Riker).

Furthermore, the active ingredients may also be used in combination with other therapeutic agents, for example, pain relievers, anti-inflammatory agents, vitamins, minerals and the like, whether for the conditions described or some other condition.

The present invention further pertains to a packaged pharmaceutical composition for controlling bone disorders such as a kit or other container. The kit or container holds a therapeutically effective amount of a pharmaceutical composition for controlling bone disorders and instructions for using the pharmaceutical composition for control of the bone disorder. The pharmaceutical composition includes at least one therapeutic agent of the present invention, in a therapeutically effective amount such that bone disorder is controlled.

All references cited herein are incorporated by reference in their entirety. The following examples illustrate certain aspects of the invention and are not intended to limit the scope thereof.

EXAMPLES

The following materials were used in these examples.

Primary human mesenchymal cells, primary human osteoblasts and corresponding media were purchased from Biowhittaker (Walkersville, Md.). Mouse mesenchymal C3H10T1/2 cells were obtained from American Type Culture Collection (Manassas, Va.) (ATCC Deposit No. CCL-226). Total RNA prepared from abdominal adipose tissue was obtained from Biochain Institute (Hayward, Calif.). General tissue culture reagents, first strand cDNA synthesis kits and Platinum Taq DNA polymerase were purchased from Invitrogen (Rockville, Md.). Noggin, gremlin, chordin, twisted gastrulation, and bone morphogenetic proteins 2, 4 and 6 were purchased from R & D Systems (Minneapolis, Minn.). Strataprep Total RNA mini-prep kits were purchased from Stratagene (San Diego, Calif.). Sephadex G-25 pre-packed NAP-5 columns were purchased from Amersham Biosciences (Piscataway, N.J.). Reagents for determining alkaline phosphatase (ALP) activity were obtained from Pierce-Endogen (Rockford, Ill.). Prolagen C ELISA kits were purchased from Quidel Corporation (Mountainview, Calif.). CellTiterGlo Cell Viability kits were obtained from Promega (Madison, Wis.). Homogeneous Caspase ELISA, Cell Death assay (Histone-Associated DNA Fragmentation), and In Situ Cell Death Detection kits were purchased from Roche Diagnostics (Indianapolis, Ind.). Caspase inhibitors, (Caspase-1, Inhibitor VI and Caspase-3, Inhibitor I) were obtained from Calbiochem (San Diego, Calif.). All other reagents and chemicals were purchased from Sigma (St. Louis, Mo.).

Example 1

Expression of SOST Correlates with Commitment and Differentiation of Precursor Cells to Osteogenic Lineage In this example, the SOST expression was correlated with cellular differentiation and was found to increase as progenitor cells developed into osteoblasts.

SOST Expression Assay

Human mesenchymal (hMSC) cells were cultured in regular growth media (Biowhittaker's MSCGM) or Osteoblast-inducing media (Biowhittaker's MSCGM medium supplemented with 100 nM dexamethasone, 50 µg/ml ascorbic acid, and 10 mM β-glycerophosphate). Media were refreshed twice per week. Cultures were harvested 1, 7 and 21 days after plating and RNA isolated for RT-PCR analyses of SOST. SOST expression was also determined in adipocytes and chondrocytes generated from mesenchymal cells cultured for 21 to 28 days in corresponding media (Pittenger et al.). Primary cultures of human osteoblasts were also grown in Osteoblast-inducing media for 21 days and RNA isolated for RT-PCR. SOST expression was also analyzed in preparations of total RNA isolated from abdominal adipose tissue and from cartilagenous ends of long bones.

Results

Cell culture conditions necessary for human-derived mesenchymal (hMSC) cells to differentiate into osteoblast-like cells were developed. Mesenchymal cells are a population of bone marrow-derived pluripotent cells, capable of differentiating into a number of different tissue types including bone, cartilage, fat, smooth muscle, tendon, marrow stroma, and neurons (Owen, 1998).

Figure 1A:
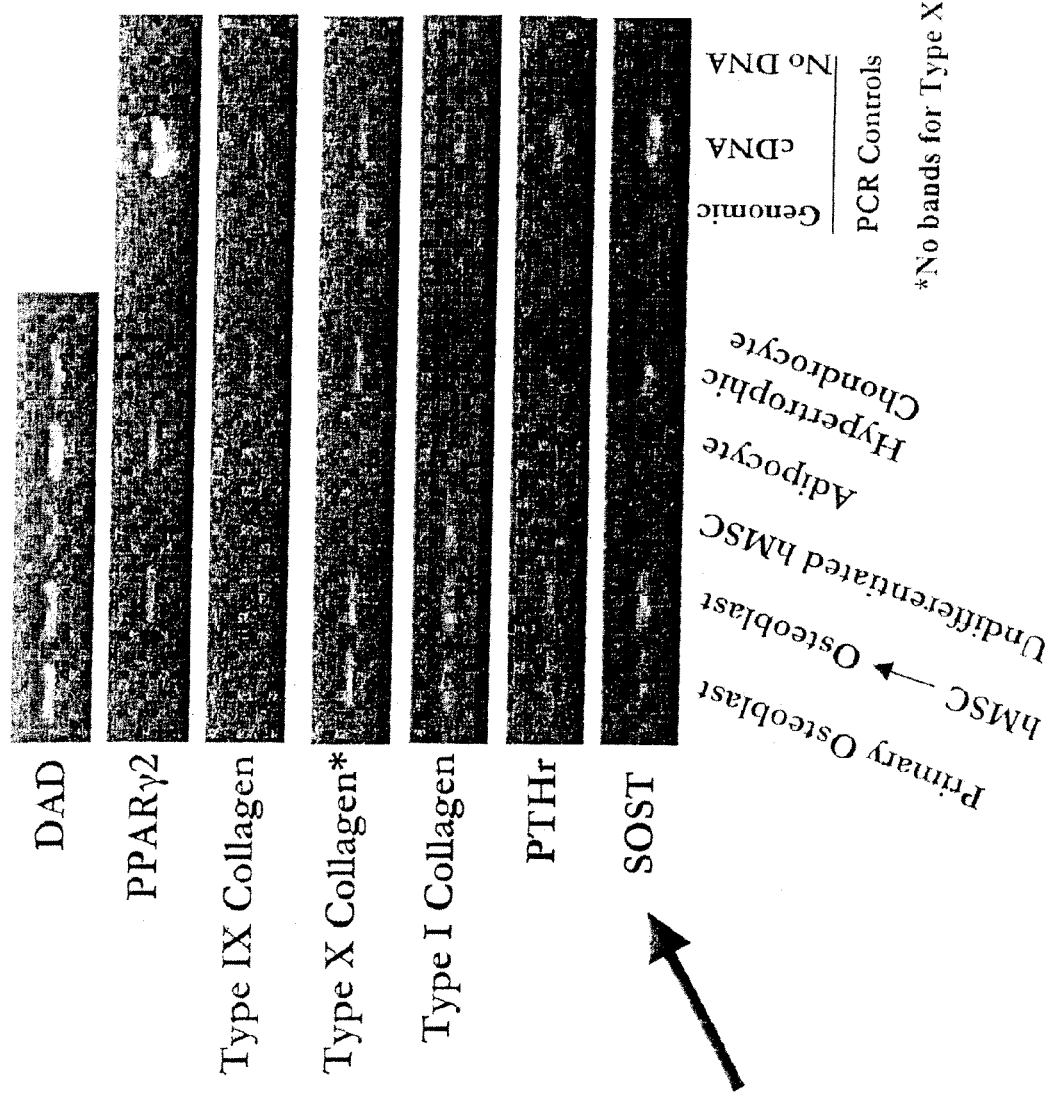
FIG. 1A provides a Reverse Transcriptase-Polymerase Chain Reaction (RT-PCR) analysis of SOST expression compared to the expression of other factors. The RNA used as a template for RT-PCR was prepared from primary human osteoblasts, undifferentiated hMSC cells and hMSC cells differentiated to yield osteoblasts, chondrocytes and adipocytes. RT-PCR amplification products were separated and visualized on an agarose gel. The cell type from which the RNA template was obtained is shown at the bottom of the gel shown in FIG. 1A. Several sets of primers were used in separate RT-PCR reactions to compare the level of SOST expression in the various cell types with the level of expression of characteristic phenotypic markers for various cell types, including parathyroid hormone receptor (PTHr), collagen (types I, X and IX), PPARγ2 (a characteristic phenotypic marker for adipocytes) and Defender Against Death (DAD, a housekeeping gene). As can be observed in FIG. 1A, undifferentiated hMSC cells and adipocytes expressed negligible levels of SOST. In contrast, the cell types capable of mineralization that express markers associated with the osteoblast and hypertrophic chondrocyte phenotype (e.g. type I collagen and type X collagen, respectively) did express SOST.

FIG. 1a provides an RT-PCR analyses of RNA prepared from primary human osteoblasts, undifferentiated hMSC cells and hMSC cells differentiated to yield osteoblastic, chondrocytic and adipocytic cells. The expression of characteristic phenotypic markers (e.g. PPARγ2 for adipocytes) in these cell types was compared with that of SOST. As can be observed in FIG. 1a, undifferentiated hMSC cells and adipocytes expressed negligible levels of SOST. In contrast, the cell types capable of mineralization that express markers associated with the osteoblast phenotype (type I collagen, type X collagen, parathyroid hormone receptor (PTHr)) expressed SOST. These included cultures of primary human osteoblasts, hMSC cells differentiated to yield osteoblastic cells and hypertrophic chondrocytes.

Figure 1B:
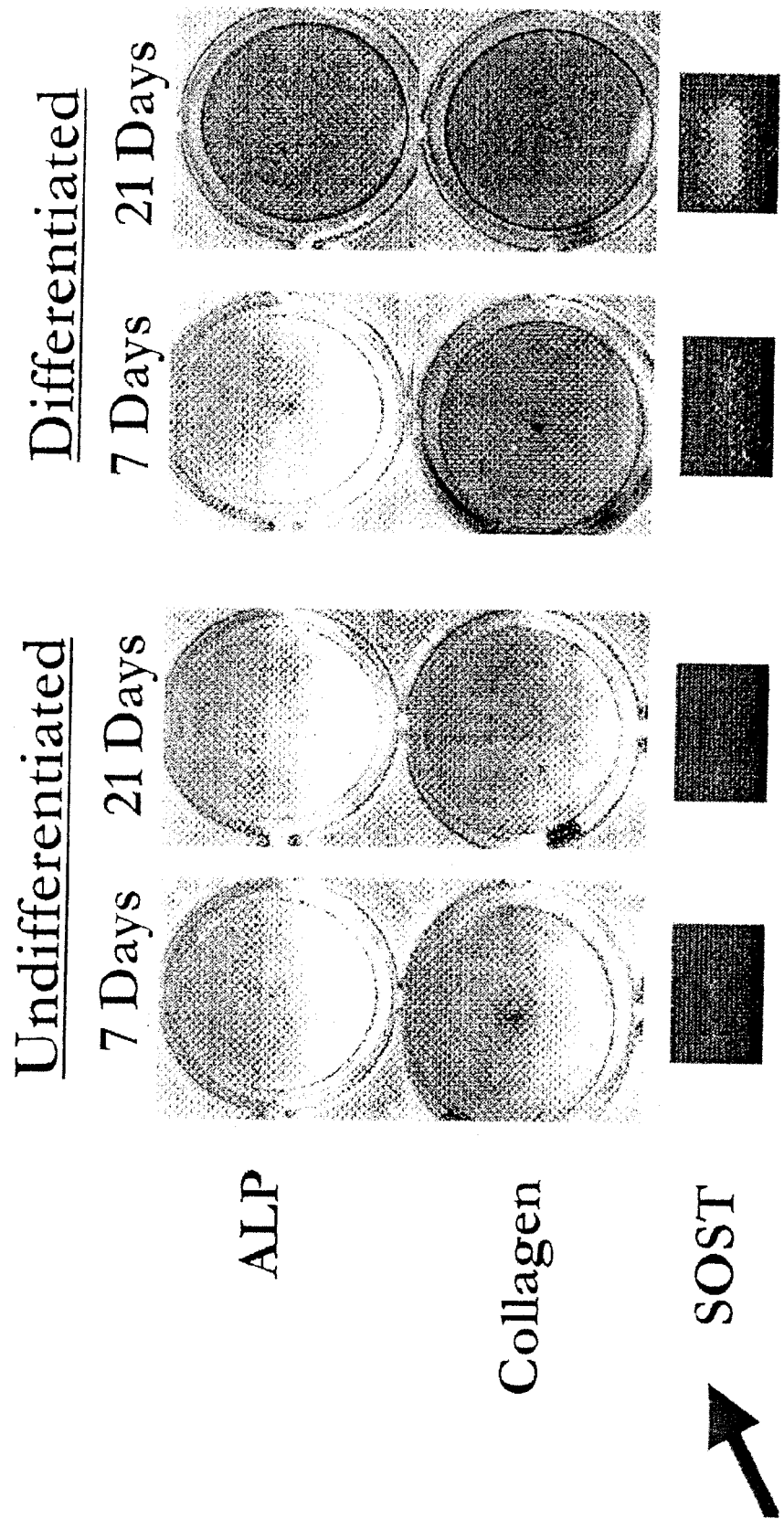
FIG. 1B illustrates that SOST is expressed at higher levels in mature osteoblasts. Human MSC cells were grown in regular growth medium (Undifferentiated) or Osteoblast-Inducing medium, (Differentiated) for 21 days. Matching cultures were stopped at 7 or 21 days and stained histochemically for alkaline phosphatase (ALP) or collagen (Masson Trichrome stain). Other cultures were processed for RT-PCR analysis of SOST expression. hMSC cells that had differentiated into osteoblasts were identified by enhanced histochemical staining for alkaline phosphatase (ALP) and collagen (FIG. 1B, purple and blue stains respectively in the original photographs of the differentiated cells in the right panel at 21 days) and deposition of mineral (negligible at Day 7 versus 437±60 μg calcium/mg protein at Day 28). Undifferentiated hMSC cells expressed negligible levels of SOST mRNA as well as negligible levels of alkaline phosphatase activity, and low collagen and, mineral deposition (FIG. 1B, left two panels). In contrast, the expression of alkaline phosphatase, collagen and SOST increased with time in cells grown in osteoblast-inducing media.

The expression of the SOST in hMSC cells that had differentiated into osteoblast-like cells was correlated with the stage of osteoblast differentiation by observing hMSC cells grown in osteoblast-inducing medium over a 21-day period. hMSC cells differentiated into osteoblasts as indicated by enhanced histochemical staining for ALP and collagen (FIG. 1b, darker stains in right panel at 21 days respectively) and deposition of mineral (negligible at Day 7 versus 437±60 µg calcium/mg protein at Day 28). Undifferentiated hMSC cells expressed negligible levels of SOST mRNA as well as negligible levels of mRNA correlating with alkaline phosphatase (ALP) activity, collagen and mineral deposition (FIG. 1b, left panel). In contrast, the expression of ALP, collagen and SOST increased with time in cells grown in osteoblast-inducing media.

These results indicate that SOST expression increases in cells committed to osteoblast differentiation.

Example 2

Regulation of SOST Expression by Growth Factors and Hormones in Human Bone Cells In this example, the effect of growth factors and hormones on SOST expression in hMSC cells or primary human osteoblasts was observed using RT-PCR. Prior to measuring SOST expression, these cells were treated for 72 hrs with BMP-2, BMP-4, BMP-6, insulin-like growth factor-1 (IGF-1), parathyroid hormone (PTH), transforming growth factor-β (TGF-β), dexamethasone (DEX), retinoic acid (RA), and 1,25-dihydroxyvitamin $D_3$ (vit D). As immature osteoblasts differentiate and become capable of mineralization, they express markers associated with the osteoblast phenotype (type I collagen and parathyroid hormone receptor (PTHr)). These markers were used to ascertain whether differentiation had occurred so that the influence of growth factors and hormones could be correlated with the stage differentiation as well as the level of SOST expression.

Methods

Human mesenchymal cells and primary human osteoblasts were plated in regular growth media containing 2% FCS at a density of 10,000 cells/cm². Test reagents ($10^{-7}$ M dexamethasone, $10^{-6}$ M retinoic acid, 10 ng/ml TGF-β1, PTH ($10^{-8}$ M), 10 or 50 ng/ml IGF-1, $10^{-7}$ M 1,25-dihydroxyvitamin $D_3$, and 50 to 300 ng/ml of bone morphogenetic proteins 2, 4 or 6) were added singly or in combination on the following day. Cultures were continued for 24 to 120 hrs after which the cells were harvested for RNA isolation.

Results

Figure 2:
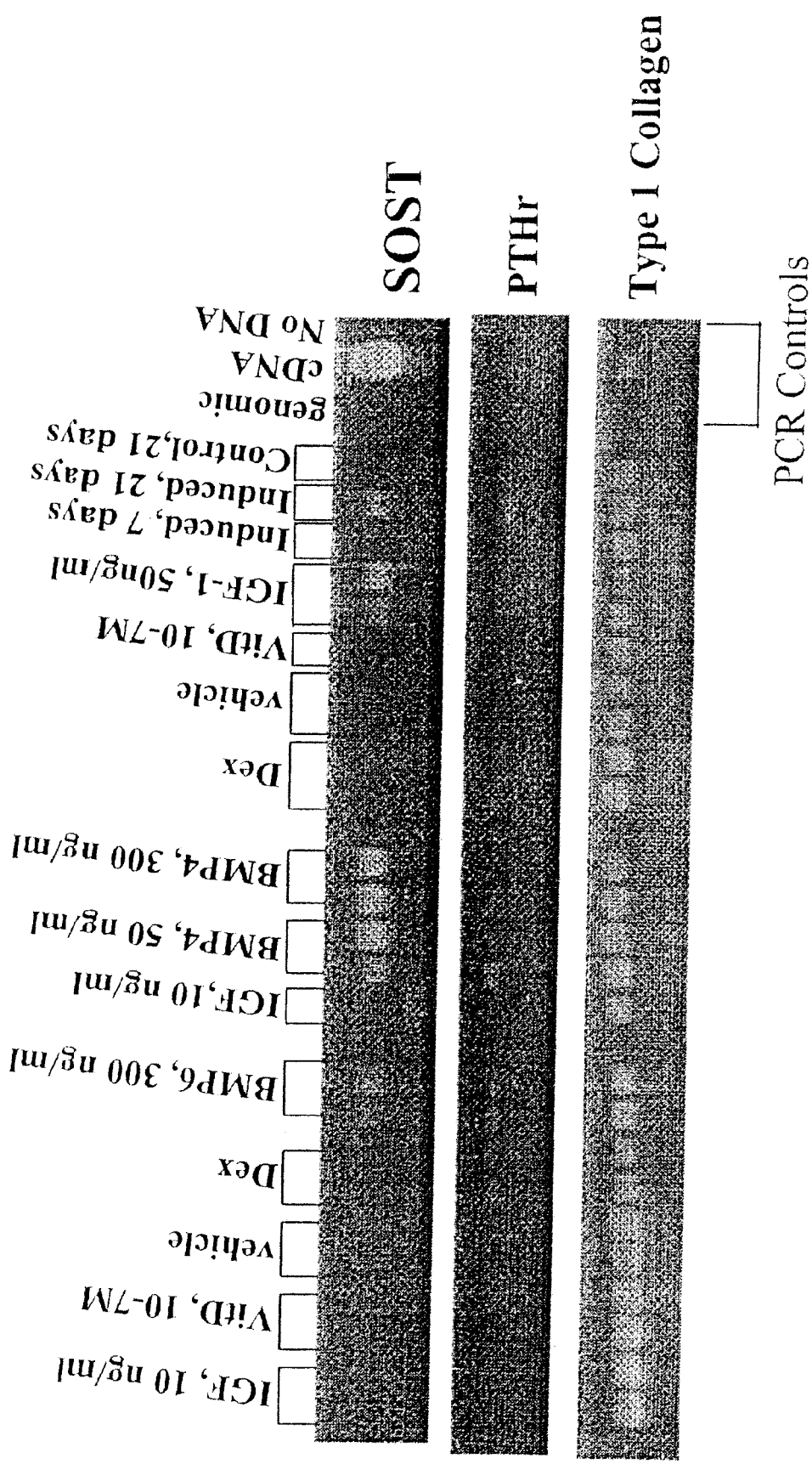

FIGS. 2 to 6 show the results of these experiments. As can be seen in FIG. 2, while untreated hMSC cells ("vehicle") strongly expressed type I collagen, they had negligible levels of PTHr and SOST (Vehicle and Control, 21 days). These results indicate that untreated hMSC cells are in an early stage of osteoblast lineage, but are committed to osteoblastogenesis. Treatment of these cells with dexamethasone, bone morphogenetic proteins, IGF-1 (IGF-1 at 50 ng/ml) or long-term culture in osteoblast-inducing media (Induced, 21 days) advanced the stage of differentiation and induced PTHr expression.

Several factors also enhanced the expression of SOST, including BMP-4, BMP-6, and IGF-1. Interestingly, factors such as vitamin D. PTH, TGF-β and dexamethasone by themselves had no effect on SOST expression. Bone morphogenetic proteins enhanced the expression of SOST in differentiating hMSC cells and in primary cultures of human osteoblasts.

Figure 3:
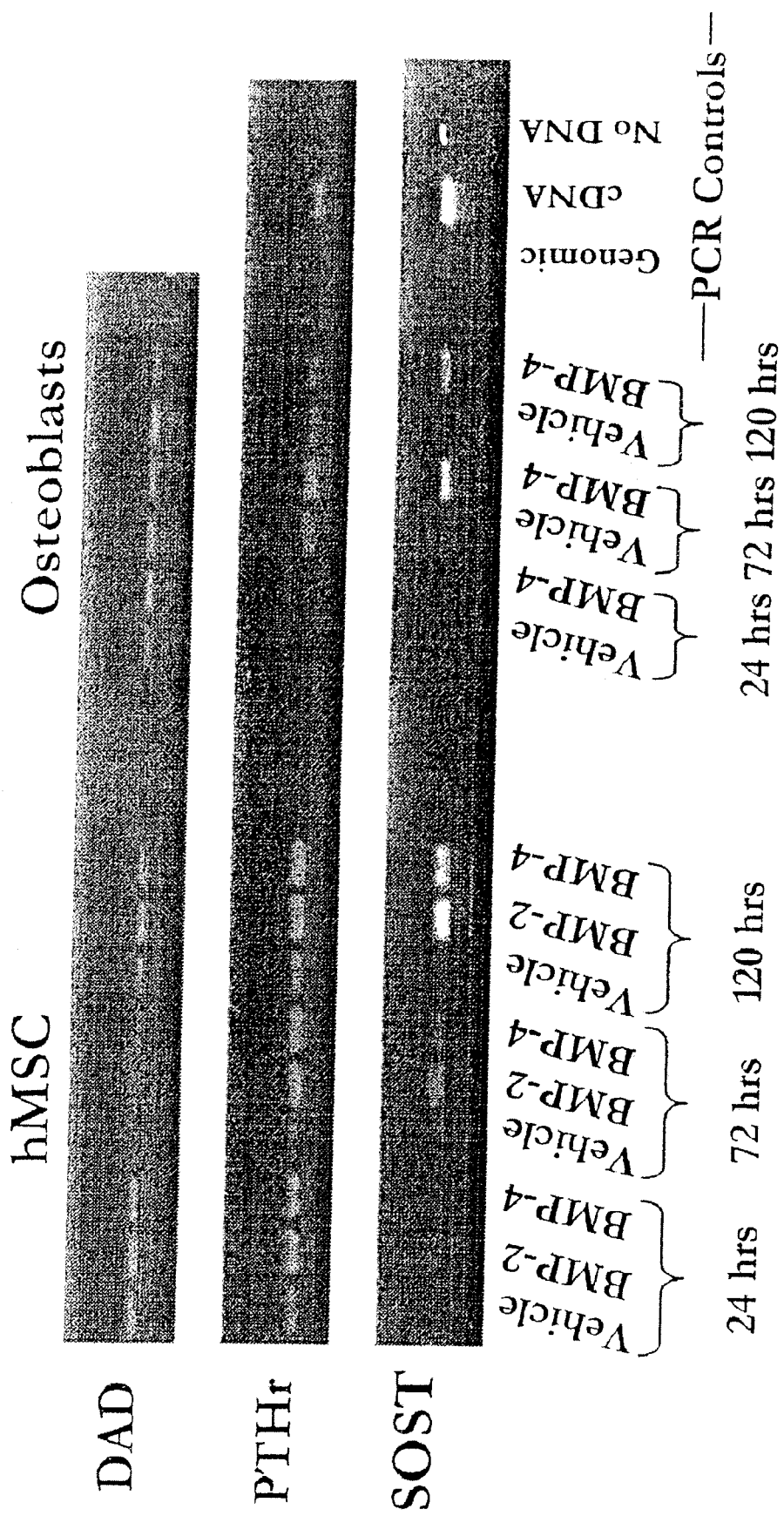

FIG. 3 provides a time course of BMP-induced expression of SOST in hMSC and primary human osteoblasts. As shown, maximum levels of SOST expression were achieved within 72 to 120 hrs after start of treatment (FIG. 3).

The proteins noggin and gremlin are thought to function as BMP antagonists by binding and inactivating bone morphogenetic proteins (Yamaguchi et al. 2000). Bone morphogenetic proteins are also thought to regulate the expressions of noggin and gremlin in osteoblastic cells in culture. See Gazzero et al. (1998); Pereira et al (2000); and Nifuji & Noda (1999). The effect of bone morphogenetic proteins on SOST expression was compared to the effect of bone morphogenetic proteins on noggin and gremlin expression.

Figure 4:
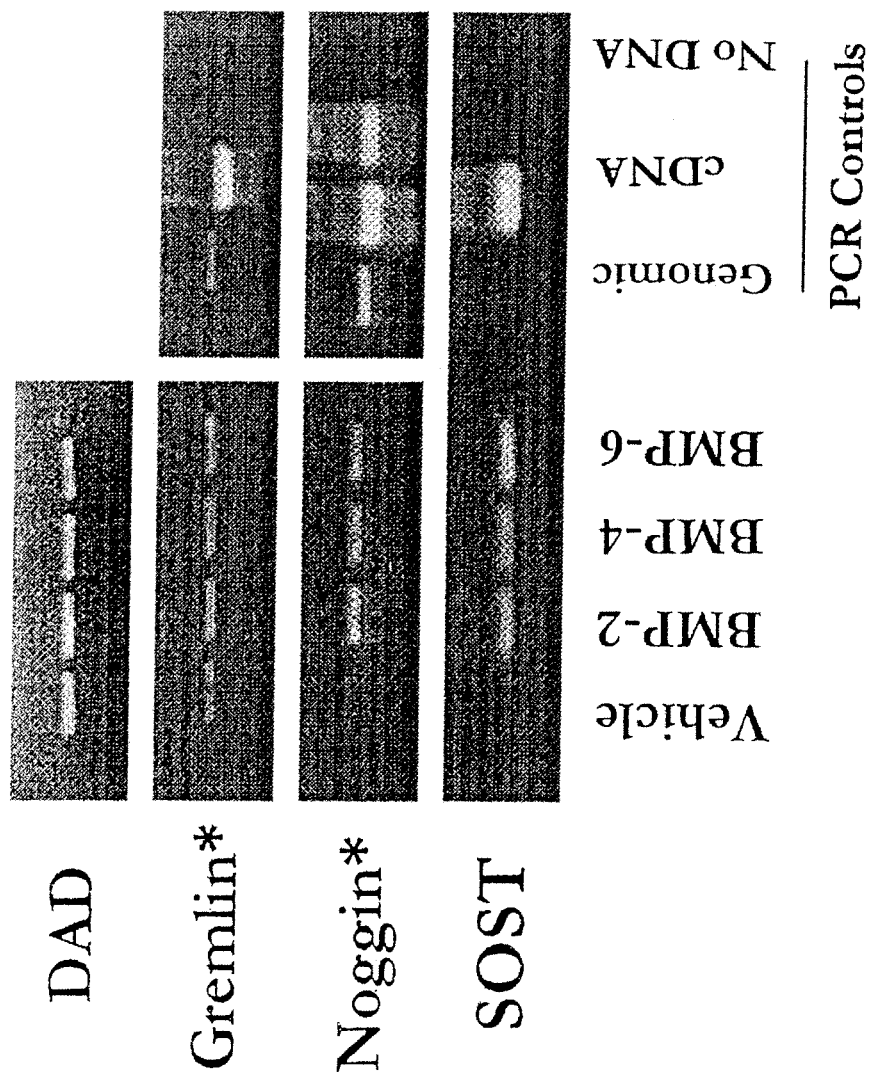

FIG. 4 shows that while the basal levels of SOST and noggin were negligible in undifferentiated hMSC cells, the levels of these genes were up-regulated by BMPs-2, 4 and 6. In contrast, gremlin was constitutively expressed in undifferentiated hMSC cells and its expression was only modestly increased by the bone morphogenetic proteins.

Steroids such as retinoids have been shown to regulate the differentiation of mesenchymal and osteoblastic cells (Gazit et al, 1999; Weston et al., 2000). The cellular response to steroids is modulated through interplay between the steroid hormone and TGF-β signaling pathways (Yanagi et al., 1999).

To determine whether steroids and/or the TGF-β signaling pathway affect BMP-mediated regulation of SOST expression, hMSC and osteoblastic cells were incubated with vitamin D, retinoic acid, and dexamethasone alone or in combination with BMP-4 for 72 hrs prior to RT-PCR analyses of SOST expression.

Figure 5:
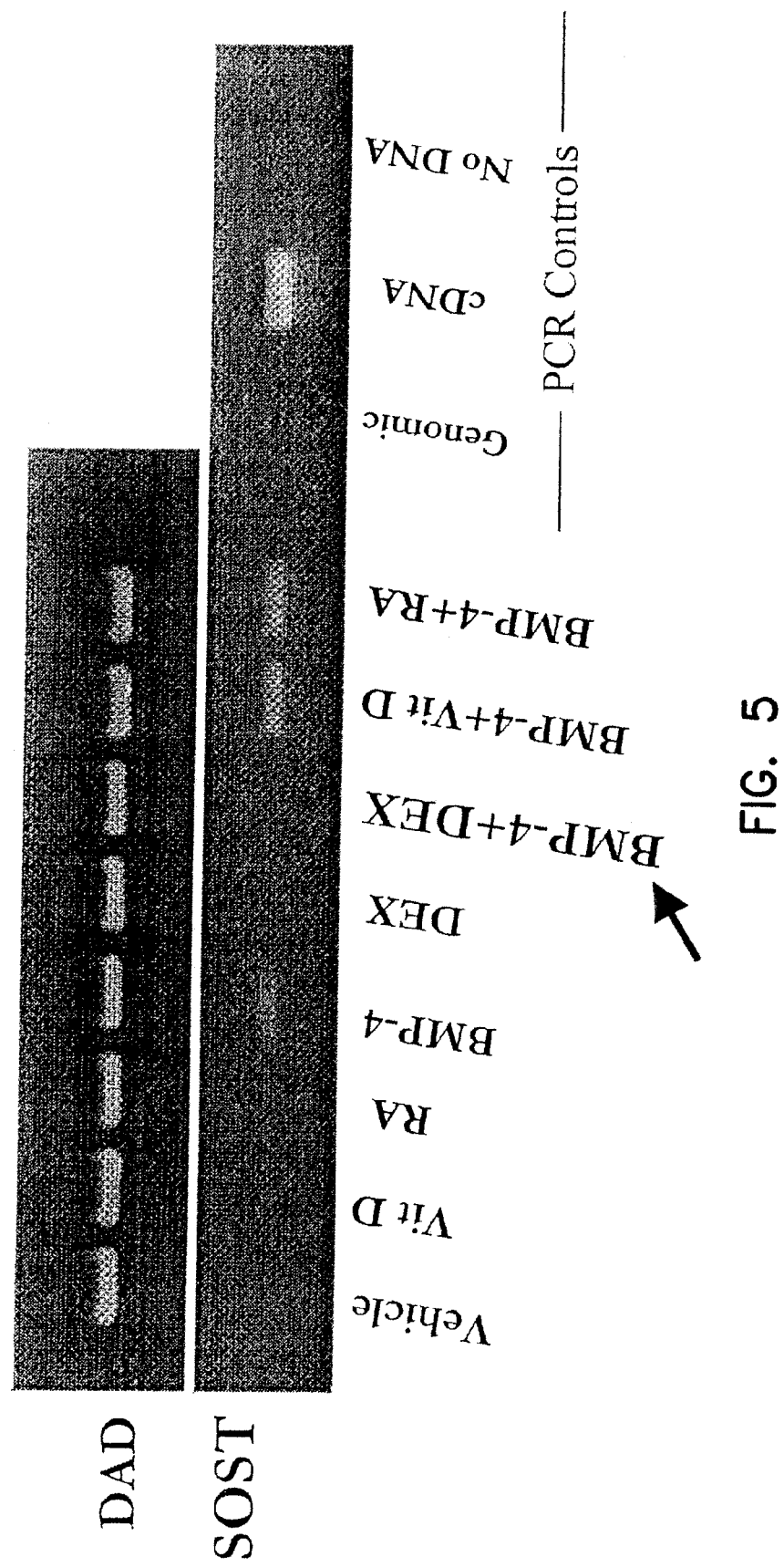

As shown in FIG. 5, steroids alone (vitamin D, retinoic acid, and dexamethasone) had no effect on the basal expression of SOST in hMSC or osteoblastic cells. However, BMP-4 enhanced SOST expression (FIG. 5). Interestingly, retinoic acid and vitamin D enhanced the levels of SOST when added in combination with BMP-4 such that the levels detected were greater than those found in cells treated with BMP-4 alone.

In contrast, there was a decrease in SOST expression levels when dexamethasone was added with BMP-4. Therefore, dexamethasone apparently abolished the stimulatory effect of BMP on SOST expression (FIG. 5).

Figure 6:
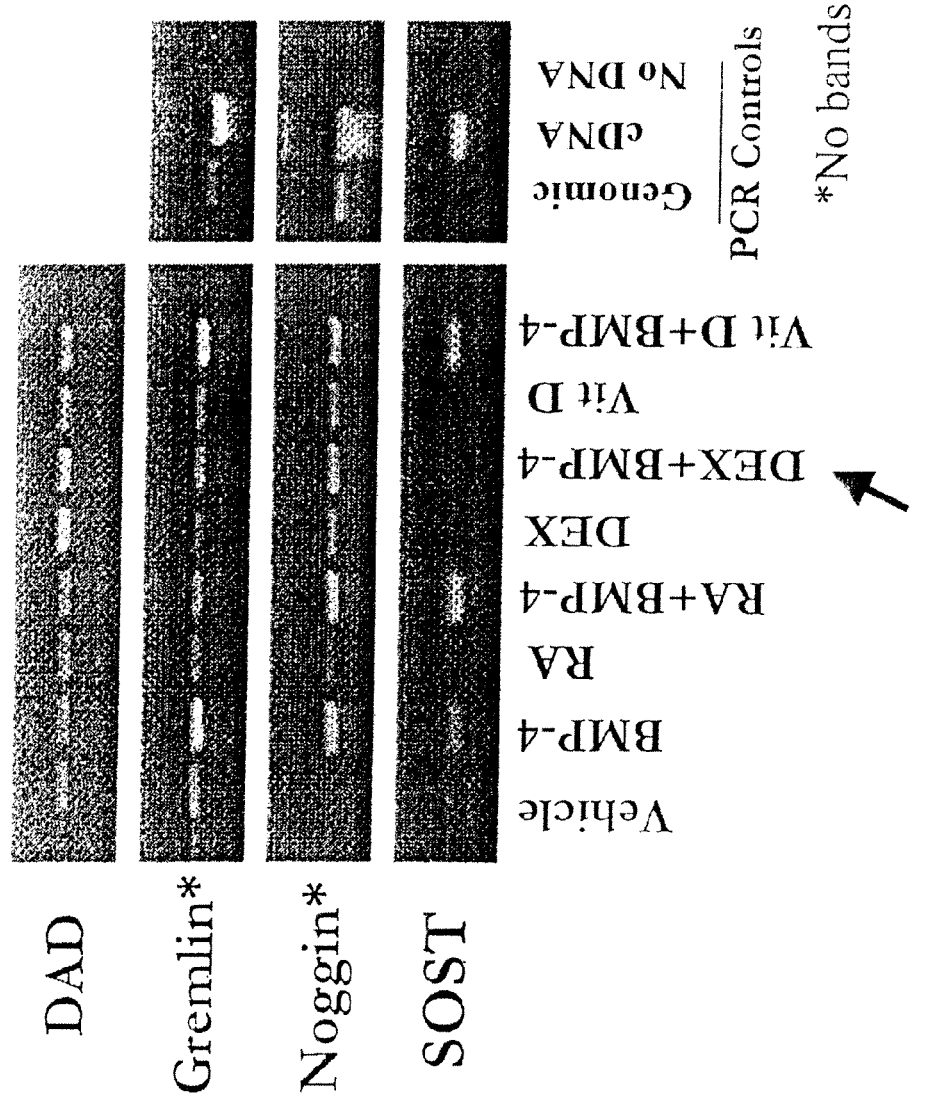

BMP-4 also enhanced gremlin and noggin expression (FIG. 6). However, steroids affected BMP-4 induced expression of gremlin and noggin somewhat differently than BMP-4 induced expression of SOST (FIG. 6). Like SOST, gremlin expression was unchanged in cells treated only with retinoic acid or vitamin D. Unlike SOST, basal levels of gremlin decreased when cells were treated with dexamethasone alone. But the stimulatory effect of BMP-4 on gremlin expression was diminished when retinoic acid and dexamethasone were added with BMP-4. Vitamin D did not alter the effect of BMP-4 on gremlin expression.

In contrast, BMP-4, retinoic acid, dexamethasone and vitamin D all appeared to increase the levels of noggin in hMSC cells. BMP-4 exerted the greatest effect. The stimulatory effect of BMP-4 on noggin was not greatly altered by steroids.

Therefore, the effects of steroids and BMP-4 on gremlin and noggin contrasted markedly with those on SOST (FIG. 6). BMP-4 significantly increased the levels of SOST expression and this effect was enhanced in the presence of vitamin D or retinoic acid but not with dexamethasone. In fact, dexamethasone significantly suppressed SOST expression.

Example 3

Compounds Affecting SOST Expression

The previous example illustrates that SOST expression was enhanced by bone morphogenetic proteins and modulated by steroids such as dexamethasone. In this example, human MSC cells were incubated with bone morphogenetic proteins in the presence of various test agents to determine whether other steroids and compounds could affect the BMP-induction of SOST. SOST expression was monitored by reverse transcriptase polymerase chain reaction (RT-PCR).

Materials and Methods

Human mesenchymal cells (hMSCs) were plated in regular growth media containing 2% FCS and treated with BMP-6 either alone or in combination with the test compounds. The cells were harvested 72 hrs later and RNA was prepared for RT-PCR analysis of SOST expression.

Results

The compounds tested and the results obtained for these compounds are summarized in Table 1.

TABLE 1

| Compound | Source | Compound Type | Concentration Tested | Results |
|---|---|---|---|---|
| Dexamethasone | SIGMA-Aldrich | Glucocorticoid analog | $1 \times 10^{-7}$ M | Inhibition |
| Triamcinolone | SIGMA-Aldrich | Glucocorticoid analog | $1 \times 10^{-7}$ M | Inhibition |
| Fluocinolone acetonide | SIGMA-Aldrich | Glucocorticoid analog | $1 \times 10^{-7}$ M | Inhibition |

TABLE 1-continued

| Compound | Source | Compound Type | Concentration Tested | Results |
|---|---|---|---|---|
| Ursodeoxycholic acid | SIGMA-Aldrich | Bile salt | $1 \times 10^{-6}$ M | Inhibition |
| | | | $3 \times 10^{-6}$ M | Inhibition |
| Tauroursodeoxycholic acid | SIGMA-Aldrich | Bile salt | $2 \times 10^{-7}$ M | No Effect |
| | | | $2 \times 10^{-6}$ M | No Effect |
| Prostaglandin E2 | Biomol | Eicosanoid | $1 \times 10^{-7}$ M | Inhibition |
| | | | $1 \times 10^{-6}$ M | Inhibition |
| Spironolactone | SIGMA-Aldrich | | $1 \times 10^{-7}$ M | No Effect |
| | | | $1 \times 10^{-6}$ M | No Effect |
| 1,2-napthoquinone-4-sulfate | SIGMA-Aldrich | | $1 \times 10^{-6}$ M | No Effect |
| | | | $5 \times 10^{-6}$ M | No Effect |
| 17β-estradiol | SIGMA-Aldrich | Estrogen | $1 \times 10^{-7}$ M | No Effect |
| | | | $1 \times 10^{-6}$ M | No Effect |
| ICI 182,780 | TOCRIS | Estrogen receptor-α antagonist | $1 \times 10^{-6}$ M | No Effect |
| Lovastatin/Mevinolin | SIGMA-Aldrich | Statin, HMG-CoA reductase inhibitor | $1 \times 10^{-7}$ M | No Effect |
| PD98059 | Calbiochem | MEK inhibitor | $2 \times 10^{-6}$ M | No Effect |
| SB203580 | Calbiochem | P38 inhibitor | $2 \times 10^{-6}$ M | No Effect |
| SB202474 | Calbiochem | MAPK inhibitor control | $2 \times 10^{-6}$ M | No Effect |
| Parathyroid Hormone (1-34) | Biomol | Calciotrophic Peptide | $1 \times 10^{-7}$ M | No Effect |

Figure 7:
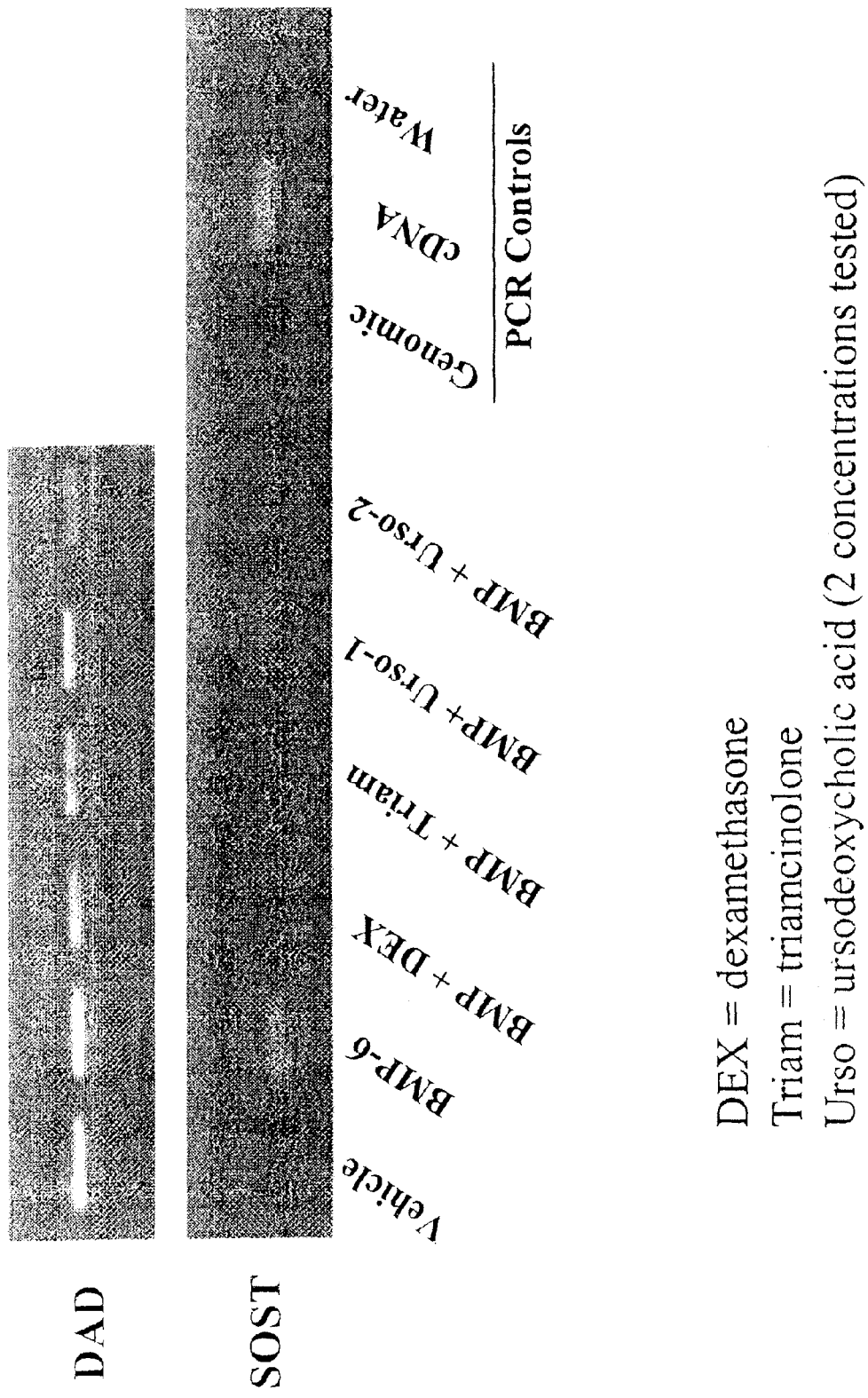
Figure 8:
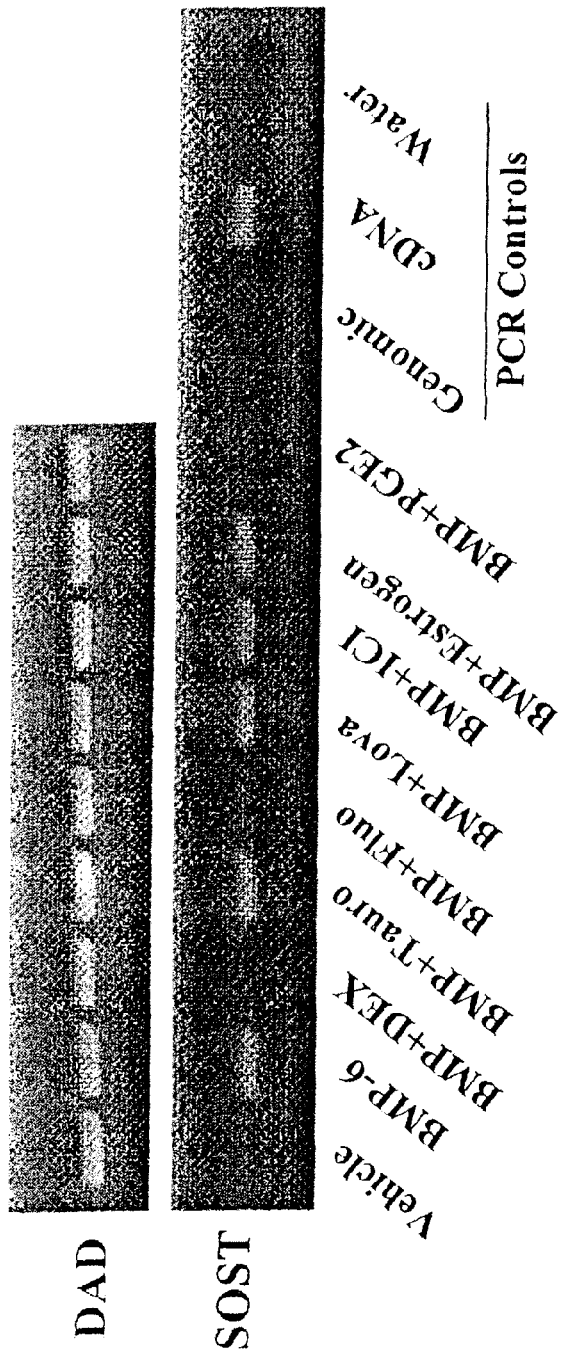

FIGS. 7 and 8 illustrate the results obtained for several compounds that blocked BMP-6 mediated induction of SOST expression in hMSC cells. Triamcinolone (Triam), a glucocorticoid analog similar to dexamethasone, blocked the stimulatory effect of BMP-6 on SOST (FIG. 7). Ursodeoxycholic acid (Urso), a bile acid used to treat primary biliary cirrhosis, also blocked the BMP-6 induction of SOST in a dose-dependent manner (FIG. 7). In particular, ursodeoxycholic acid at $3 \times 10^{-6}$ M (Urso-2) completely blocked the induction of SOST by BMP-6 (FIG. 7).

FIG. 8 shows the results of treatment of hMSC cells with fluocinolone acetonide (Fluo) and prostaglandin E2 (PGE2). Both compounds effectively blocked the induction of SOST by BMP-6 whereas other compounds (tauroursodeoxycholic acid, ICI 182,780, estrogen and lovastatin) had minimal effects.

The structures for the five compounds that effectively blocked the induction of SOST expression by BMP-6 are shown in FIG. 9.

These results indicate that 3 different types of glucocorticoid analogs were capable of blocking the induction of SOST expression by BMPs. Other compounds that also blocked SOST expression included bile salts (e.g. ursodeoxycholic acid), and prostaglandins.

Example 4

Exogenously Added Sclerostin Regulates Expression of Osteoblast Function

Individuals with heterozygous or homozygous SOST mutations have a skeletal phenotype characterized by denser and heavier bones (Beighton et al. 1976). In this example, the sclerostin gene product was added to in vitro cultures of osteoblasts. Osteoblastic phenotypic markers were used to monitor the stage of differentiation at which the sclerostin protein affected osteoblastic function.

Determining Effects of Sclerostin Protein on Human Mesenchymal Cells hMSC cells were plated in 96-well tissue culture dishes at a density of 10,000 cells/cm² in Osteoblast-Inducing medium. Partially purified preparations of baculovirus-expressed sclerostin protein were prepared in sterile PBS using NAP-5 columns prior to use. Human sclerostin protein (0 to 30 μg/ml) or an equal volume of Sf9 conditioned media (Control) was added to cultures of hMSC cells at various times after plating (1 day, 8 days, 15 days, or 21 days). The effects of sclerostin on osteoblastic differentiation were assessed by measuring alkaline phosphatase activity (ALP, determined in cell layers using DEAA buffer (Pierce) containing 0.5% NP-40 and 10 mM p-nitrophenylphosphate), synthesis of collagen type I (Prolagen C ELISA), and calcium deposition for mineralization (colorimetric assay of acid lysates of cell layers, Sigma).

Determining the Effects of Sclerostin Protein on Mouse Mesenchymal C3H10T1/2 Cells C3H10T1/2 cells (ATCC Deposit No. CCL-226) were plated in 96-well dishes at a density of 25,000 cells per well in complete growth medium (DMEM with high glucose and glutamine supplemented with 10% FCS, 1% penicillin/streptomycin, 0.1 mM non-essential amino acids, 1 mM sodium pyruvate, 55 μM β-mercaptoethanol, and 20 mM HEPES, pH 7.3). C3H10T1/2 cells were used in a short-term (72 hr) assay to determine the effects of human sclerostin protein on BMP-induced ALP activity. Partially purified preparations of baculovirus-expressed sclerostin protein were prepared in sterile PBS using NAP-5 columns prior to use. Sclerostin protein (0 to 50 μg/ml) or an equal volume of Sf9 conditioned media (control) was pre-incubated with 500 ng/ml BMP-6 for 1 hr prior to addition to cells: For comparison, similar incubations were carried out with anti-BMP-6 antibody and noggin. Cells were harvested 72 his later for determination of ALP activity.

To test the specificity of the sclerostin effect, human sclerostin that was synthesized with a FLAG tag, was pre-incubated for 2 hrs at 4° C. with an anti-FLAG antibody coupled to agarose beads. The mixture was then spun down at 10,000×g for 15 minutes at 4° C. and the supernatant treated as "sclerostin protein" in the above assay.

Results

Figure 10:
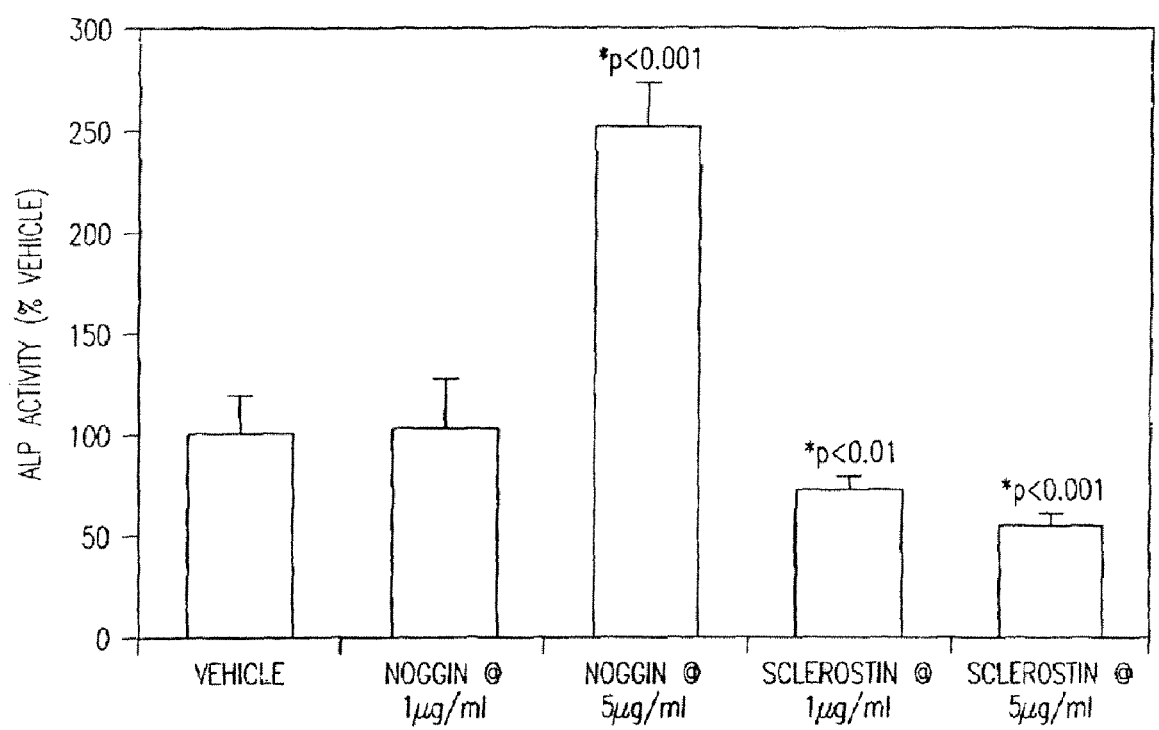
FIGS. 10 to 19 demonstrate the inhibitory effect of sclerostin on the activity of osteoblastic markers. Filially.

FIG. 10 provides a comparison of the effects of human sclerostin and mouse noggin proteins on alkaline phosphatase (ALP) activity in differentiating hMSC cells. Alkaline phosphatase activity is a phenotypic marker for osteoblast differentiation. After 7 days of treatment, noggin at 1 µg/ml had no effect on alkaline phosphatase activity whereas noggin at 5 µg/ml significantly increased alkaline phosphatase activity (p<0.001 to vehicle-treated cells).

In contrast, under the same conditions, partially purified preparations of human sclerostin consistently decreased alkaline phosphatase activity when administered at either 1 or 5 µg/ml (FIG. 10).

Sclerostin also decreased alkaline phosphatase activity in primary cultures of human osteoblasts (FIG. 11). Osteoblasts that were grown in regular growth media expressed basal levels of alkaline phosphatase (FIG. 11, far right panel); these levels increased significantly when cells were grown in Inducing media (middle panel, darker stain). When a similar group of cells were treated with human sclerostin, there was a marked decrease in the amount of alkaline phosphatase expressed, as evidenced by the reduction in stain (FIG. 11, Sclerostin+Inducing Media).

Sclerostin decreased alkaline phosphatase activity and mineralization in hMSC cells in a dose-dependent manner (FIG. 12). Alkaline phosphatase activity and deposition of mineral (as measured by calcium assay) were significantly decreased in cells treated with increasing concentrations of partially purified preparations of human sclerostin protein but not the control (proteins purified from conditioned Sf9 media) (FIG. 12). Alkaline phosphatase activity and mineral deposition were decreased by about 50% in cells treated with about 10 to 15 µg/ml of the protein (p<0.001 to control).

Synthesis of collagen type I was also decreased in a dose-dependent manner in sclerostin-treated cultures. Partially purified preparations of human sclerostin reduced the synthesis of type I collagen by about 50% in cells treated with 10 µg/ml of the protein (p<0.001 to control, FIG. 13).

To determine the effect of sclerostin protein on the expression of osteoblastic markers in cultures of differentiating hMSC cells, RNA was isolated a tier a 40-hr treatment and analyzed by RT-PCR (FIG. 14). As can be seen in FIG. 14, RNA levels of markers for adipocytes (PPARγ2) or undifferentiated mesenchymal cells (endoglin) were not affected by treatment with partially purified preparations of human sclerostin protein. On the other hand, RNA levels for osteoblast phenotypic markers such as PTHr, Type I collagen, BMP-2 and BMP-6 were significantly reduced in cells treated with partially purified preparations of human sclerostin protein compared to cells treated with proteins purified from conditioned Sf9 media (control).

BMPs modulate the activity of osteoblasts. Treatment of osteoprogenitor or pre-osteoblasts with BMPs can enhance the activity of markers such as ALP (Gazzero et al. 1998, Nifuji & Noda, 1999). In cultures of hMSC, BMP-6 increased the activity of ALP about 2-fold (FIG. 15). Sclerostin reduced this BMP-induced ALP activity in a dose-dependent manner (ANOVA, p<0.0001). ALP levels in cells treated with BMP-6+30 µg/ml sclerostin were significantly lower than that expressed in BMP-6 treated or vehicle-treated cells (p<0.0001). Indeed, sclerostin also significantly reduced the basal levels of ALP in a dose-dependent manner (ANOVA, p<0.0001).

In FIG. 16, increasing concentrations of BMP-6 partially reversed the inhibitory effect of sclerostin on alkaline phosphatase activity in hMSC cultures.

These findings show that sclerostin interacts with BMPs in regulating osteoblast function.

In mouse mesenchymal C3H10T1/2 cells, ALP activity was increased in a dose-dependent manner by BMP-6 (FIG. 17). The stimulatory effect of BMP-6 on alkaline phosphatase activity in these cells was antagonized by mouse noggin, by partially purified preparations of human sclerostin and by a neutralizing antibody to BMP-6. FIG. 17 shows that mouse noggin decreased BMP-6 stimulated alkaline phosphatase activity with an 1050 of 0.3 µg/ml, data that contrast with the findings of Abe et al (2000). The anti-BMP-6 antibodies decreased BMP-6 stimulated alkaline phosphatase activity by 50% with an IC50 of 0.49 µg/ml. In addition, the partially purified preparation of human sclerostin effectively decreased BMP-6 stimulated alkaline phosphatase activity in a dose-dependent manner, with an IC50 of 10 µg/ml (FIG. 17).

To verify the specificity of the sclerostin response, a human sclerostin fusion protein was prepared that had a FLAG tag fused to the sclerostin coding region. Before addition to mouse mesenchymal C3H10T1 cells, the human sclerostin-FLAG preparation was immuno-depleted with an anti-Flag M2 antibody/agarose complex. As can be seen in FIG. 17, pre-incubation of the sclerostin-FLAG preparation with an anti-Flag antibody/agarose bead complex completely abolished sclerostin antagonism of BMP-6 in the C3H10T1/2 cells. These data indicate that the diminution of BMP-6 induced alkaline phosphatase activity observed upon addition of partially purified sclerostin protein is specifically due to sclerostin, rather than to some unidentified co-purified substance.

Example 5

Sclerostin Causes Apoptosis

Apoptosis is mediated by the activation of a series of cysteine proteases known as caspases (Thornberry & Lazebnik, 1998). Caspases activate proteins such as Bax that promote apoptosis as well as proteins that exhibit protective properties (for example, I-TRAF and Survivin). The initiation of the apoptosis cascade can occur through a number of different mechanisms including the recruitment of; and the ligand binding to, cell surface Death receptors such as FAS (Vaughan et al. 2002; Budd, 2002). In the present example, the role of sclerostin in the survival of osteoblasts is investigated by incubating hMSC cells with sclerostin and measuring the levels of caspases and other pro-apoptotic factors.

Cell Viability and Apoptosis Assays

Human mesenchymal (hMSC) cells were plated in Osteoblast-inducing media (Biowhittaker's MSCGM medium supplemented with 100 nM dexamethasone, 50 µg/ml ascorbic acid, and 10 mM β-glycerophosphate) at a density of 10,000 cells/cm$^2$ in 96-well dishes.

For cell viability assays, cells were treated with a partially purified preparation of bacculovirus-expressed human sclerostin (0 to 20 µg/ml) or an equal volume of a protein preparation purified from Sf9 conditioned media (control) for 1 week. Sclerostin and control were refreshed upon media change. Cells were then lysed and processed using Promega's CellTiterGlo Luminescence Viability Assay.

For apoptosis assays, cells were treated with sclerostin or commercially available preparations of the BMP antagonists noggin, chordin, gremlin or twisted gastrulation (Tsg) for 24 hours prior to assay for caspase activity. In some experiments, cells were treated for various times with a partially purified preparation of bacculovirus-expressed human sclerostin (0 to 30 μg/ml) or an equal volume of a protein preparation purified from Sf9 conditioned media (control) in the absence or presence of Calbiochem's caspase inhibitors. Cells were harvested and processed for apoptosis assays using the Homogeneous Caspase ELISA (Roche) or Cell Death (Histone-Associated DNA Fragmentation, Roche).

For apoptosis determination by TUNEL staining, cells were treated for 24 hrs with a partially purified preparation of bacculovirus-expressed human sclerostin (20 μg/ml) or an equal volume of a protein preparation purified from Sf9 conditioned media (control). Cells were fixed with paraformaldehyde and processed using Roche's In Situ Cell Death Detection kit.

In another study, hMSC were treated with vehicle or sclerostin for 6 hrs or 48 hrs. Cells were harvested, RNA prepared and used for the analysis of a commercially available Apoptosis Gene Array (SuperArray, Bethesda, Md.).

Results

FIG. 20 shows the effect of a 7-day treatment of hMSC cells with a partially purified preparation of human sclerostin. Cells were lysed and processed with Promega's CellTiter Glo Viability assay. At this point in time, these cells represent committed osteoprogenitors/pre-osteoblasts. They express high levels of Type 1 collagen and low levels of alkaline phosphatase. Treatment with increasing concentrations of human sclerostin significantly reduced the number of hMSC cells remaining in the culture compared to cells treated with the control (proteins purified from Sf9 conditioned media).

Treatment of hSMC with sclerostin significantly increased caspase activity (FIG. 21). An inactive preparation of sclerostin (as determined by lack of effects in other biological and biochemical assays) did not significantly affect caspase activity. When commercially available BMP antagonists (noggin, chordin, gremlin, Tsg) were added to hSMC under the same conditions, no increase in caspase activity was observed. These findings show that sclerostin selectively increases the apoptosis of human bone cells.

FIG. 22 illustrates that increasing concentrations of partially purified human sclerostin significantly elevated the activities of caspases as well as the amounts of histone-associated DNA fragments. DNA fragmentation can also be detected by TUNEL staining using commercially available reagents. Increased staining for apoptotic nuclei can be seen in sclerostin-treated as compared to control (proteins purified from Sf9 conditioned media)-treated cells in FIG. 23 (see arrows). Sclerostin decreases the survival of osteoblastic cells by promoting their apoptosis.

Sclerostin treatment of hMSC cells elevated caspase activity for up to 72 hrs (FIG. 24a). Rat sclerostin also increased the apoptosis of hMSC cells but to a lesser extent that the human protein (FIG. 24b).

The induction of caspase activity by sclerostin in hMSC cells could be effectively decreased by commercially available caspase inhibitors (FIG. 25). Caspase-1 inhibitor and Caspase-3 inhibitor effectively blocked the induction of caspase activity by human sclerostin. The combination of the two inhibitors was more potent than either one alone.

To further investigate the effects of sclerostin on the apoptosis of hMSC, RNA was harvested from vehicle and sclerostin-treated cells and used the RNA to probe a cDNA expression array containing apoptosis genes. The results for vehicle and sclerostin-treated samples were compared and data (corrected for background) were expressed as a ratio of sclerostin to vehicle. The data is summarized in the table below.

| Incubation Time | Gene | Function | Ratio |
|---|---|---|---|
| 6 hrs | BAX | Proapoptotic | 1.53 ± 0.2 |
| | Bcl10 | Proapoptotic | 4.09 ± 2.13 |
| | Hrk | Proapoptotic | 1.59 ± 0.39 |
| | Myd88 | Proapoptotic | 1.4 ± 0.31 |
| | Caspase 3 | Proapoptotic | 2.46 ± 0.69 |
| | Caspase 4 | Proapoptotic | 1.83 ± 1.12 |
| | Caspase 7 | Proapoptotic | 1.76 ± 0.18 |
| | XIAP | Anti-apoptotic | 2.01 ± 0.64 |
| | Survivin, IAP2 | Anti-apoptotic | 1.32 ± 0.48 |
| | Bruce | Anti-apoptotic | 1.45 ± 0.75 |
| 48 hrs | Bak1 | Proapoptotic | 2.36 ± 0.74 |
| | Blk | Proapoptotic | 1.83 ± 0.12 |
| | Myd88 | Proapoptotic | 2.64 ± 1.3 |
| | Bax | Proapoptotic | 1.64 ± 0.3 |
| | Bcl10 | Proapoptotic | 1.84 ± 0.76 |
| | I-TRAF | Anti-apoptotic | 2.05 ± 0.54 |
| | Casper | Anti-apoptotic | 2.68 ± 0.28 |
| | Mdm2 | Anti-apoptotic | 1.66 ± 0.34 |

In hMSC treated for 6 hrs with sclerostin, there was a significant 2 to 4-fold increase in the expression of apoptosis-associated genes such as caspase 3, caspase 4, caspase 7 and the Bcl-2 family members, Bax and Hrk as well as genes involved in cell survival (XIAP, survivin, and Bruce which have been reported to inhibit caspases 3, 7 and 9). By 48 hrs, there was increased expression of proapoptotic members of the Bcl-2 family as well as anti-apoptotic genes (Casper, I-TRAF). Thus treatment of hSMC with sclerostin triggers the induction of proapoptotic as well as anti-apoptotic genes.

In FIG. 25, two commercially available caspase inhibitors (Calbiochem's Caspase-1, Inhibitor VI which blocks caspases 1 and 4, and Caspase-3, Inhibitor I which blocks caspases 3, 6, 7, 8 and 10) blocked sclerostin-induced caspase activities in hMSC cultures. These findings, in addition to those from the apoptosis array, suggest that sclerostin enhances the apoptosis of osteoblastic cells via a FAS-mediated pathway.

Summary

The data shown in these examples demonstrate that sclerostin interacts with BMPs to modulate the activity of osteoblastic cells. This ability of sclerostin to interact with important growth factors is also likely the basis by which it modulates the survival of osteoblasts. By making the growth factors unavailable for cell function, sclerostin may increase the apoptosis of bone cells. Thus agents that block the ability of sclerostin to decrease cell survival and osteoblastic activity offer promise as agents useful in restoring lost bone.

Example 6

Small Interfering RNAs (SiRNAs) to Block Expression of SOST

SiRNAs were designed using the guidelines provided by Ambion (Austin, Tex.). Briefly, the SOST cDNA sequence was scanned for target sequences that had AA dinucleotides. Sense and anti-sense oligonucleotides were generated to these targets (AA+3' adjacent 19 nucleotides) that contained a G/C content of 35 to 55%. These sequences were then compared to others in the human genome database to minimize homology to other known coding sequences (Blast search).

The target and siRNA sequences designed are provided below.

Target sequence 1: AAGAATGATGCCACGGAAATC (SEQ ID NO: 9)
Position in gene sequence: 140
GC content: 42.9%
Sense strand siRNA: GAAUGAUGCCACGGAAAUCtt (SEQ ID NO: 10)
Antisense strand siRNA: GAUUUCCGUGGCAUCAUUCtt (SEQ ID NO: 11)

Target sequence 3: AATGATGCCACGGAAATCATC (SEQ ID NO: 12)
Position in gene sequence: 143
GC content: 42.9%
Sense strand siRNA: UGAUGCCACGGAAAUCAUCtt (SEQ ID NO: 13)
Antisense strand siRNA: GAUGAUUUCCGUGGCAUCAtt (SEQ ID NO: 14)

Target sequence 5: AACAACAAGACCATGAACCGG (SEQ ID NO: 15)
Position in gene sequence: 209
GC content: 47.6%
Sense strand siRNA: CAACAAGACCAUGAACCGGtt (SEQ ID NO: 16)
Antisense strand siRNA: CCGGUUCAUGGUCUUGUUGtt (SEQ ID NO: 17)

Target sequence 27: AATTGAGAGTCACAGACACTG (SEQ ID NO: 18)
Position in gene sequence: 950
GC content: 42.9%
Sense strand siRNA: UUGAGAGUCACAGACACUGtt (SEQ ID NO: 19)
Antisense strand siRNA: CAGUGUCUGUGACUCUCAAtt (SEQ ID NO: 20)

Target sequence 28: AAATGGAAGCATTTTCACCGC (SEQ ID NO: 21)
Position in gene sequence: 1035
GC content: 42.9%
Sense strand siRNA: AUGGAAGCAUUUUCACCGCtt (SEQ ID NO: 22)
Antisense strand siRNA: GCGGUGAAAAUGCUUCCAUtt (SEQ ID NO: 23)

Target sequence 30: AAAGTCCAGGGACTGGTTAAG (SEQ ID NO: 24)
Position in gene sequence: 1093
GC content: 47.6%
Sense strand siRNA: AGUCCAGGGACUGGUUAAGtt (SEQ ID NO: 25)
Antisense strand siRNA: CUUAACCAGUCCCUGGACUtt (SEQ ID NO: 26)

Target sequence 31: AAGAAAGTTGGATAAGATTCC (SEQ ID NO: 27)
Position in gene sequence: 1111
GC content: 33.3%
Sense strand siRNA: GAAAGUUGGAUAAGAUUCCtt (SEQ ID NO: 28)
Antisense strand siRNA: GGAAUCUUAUCCAACUUUCtt (SEQ ID NO: 29)

Target sequence 36: AACTGTAGATGTGGTTTCTAG (SEQ ID NO: 30)
Position in gene sequence: 1201
GC content: 38.1%
Sense strand siRNA: CUGUAGAUGUGGUUUCUAGtt (SEQ ID NO: 31)
Antisense strand siRNA: CUAGAAACCACAUCUACAGtt (SEQ ID NO: 32)

Target sequence 40: AATTCTCCTTCGGGACCTCAA (SEQ ID NO: 33)
Position in gene sequence: 1269
GC content: 47.6%
Sense strand siRNA: UUCUCCUUCGGGACCUCAAtt (SEQ ID NO: 34)
Antisense strand siRNA: UUGAGGUCCCGAAGGAGAAtt (SEQ ID NO: 35)

Target sequence 47: AAAGAGAGAGAATGAATGCAG (SEQ ID NO: 36)
Position in gene sequence: 1414
GC content: 38.1%
Sense strand siRNA: AGAGAGAGAAUGAAUGCAGtt (SEQ ID NO: 37)
Antisense strand siRNA: CUGCAUUCAUUCUCUCUCUtt (SEQ ID NO: 38)

Target sequence 63: AAGAAGCTATGCTGCTTCCCA (SEQ ID NO: 39)
Position in gene sequence: 1590
GC content: 47.6%
Sense strand siRNA: GAAGCUAUGCUGCUUCCCAtt (SEQ ID NO: 40)
Antisense strand siRNA: UGGGAAGCAGCAUAGCUU (SEQ ID NO: 41)

Target sequence 70: AAATCACATCCGCCCCAACTT (SEQ ID NO: 42)
Position in gene sequence: 1726
GC content: 47.6%
Sense strand siRNA: AUCACAUCCGCCCCAACUUtt (SEQ ID NO: 43)
Antisense strand siRNA: AAGUUGGGGCGGAUGUGAUtt (SEQ ID NO: 44)

These siRNAs will be tested in vitro and in vivo to ascertain how well they modulate SOST RNA levels.

REFERENCES

Abe, E et al. 2000 J Bone Min Res 15:663
Beighton, P et al. 1976 Ann Int Med 84:393
Beresford & Owen, 1998 Marrow Stromal Cell Culture, Cambridge University Press
Boden, S et al., 1997 Endocrinology 138: 2820
Bostrom et al., J. Orthopaed. Res. 13, 357, 1995.
Brunkow, M et al. 2001 Amer J Hum Genet. 68: 577-589.
Budd, R C 2002 J Clin Invest 109: 437.
Cooper, M S et al. J Endocrinology 1999, 163: 159.
Fang et al., Pro. Natl. Acad. Sci. USA. 93, 5753, 1996.
Gazzero, E et al. 1998 J Clin Invest 102:2106.
Gazit, D et al., 1999 Mol Endocrinol 7: 189.
Gitelman, S E et al., 1995 Cell Growth & Differ 6: 827.
Hofmann et al. FEBS Letters 1998, 441: 441.
Lian, J B et al. 1999 in *Primer on the Metabolic Bone Diseases and Disorders of Mineral Metabolism*, 4th edition, M J Favus (ed), Lippincott, Philadelphia, pg. 14.
Lu, T T et al. 3 Biol Chem 2001, 276: 37735.
Katagiri, T et al., 1990 Biochem Biophys Res Commun 172: 295.
Manolagas, S C 2000 Endocrine Rev 21: 115.
Martinez, L A et al. 2002 PNAS 99: 14849.
Miura et al J. Biol Chem 2001, 276: 47371.
Nakase et al., J. Bone Miner. Res. 9, 651, 1994.
Nifuji, A & Noda, M 1999 J Bone Min Res 14: 2057.
Oreffo, R O C et al. 1999 J Cell Biochem 75: 382.
Pelletier, J P et al. Am J Ther 1996, 3:115.
Pereira, R et al. 2000 Endocrinology 141: 4558.
Pittenger, M F et al. 1999 Science 284: 143.
Pockwinse, S et al., 1992 J Cell Biochem 49:310.
Scherr, M et al. Curr Med Chem 2003 10:245.
Song, C Z et al. Proc Natl Acad Sci USA 1999, 96:11776.
Suzawa, M et al., 1999 Endocrinology 140: 2125.
Takiguchi, T et al. J Periodontal Res 1999, 34:431.
Tanaka, H & Makino, I. BBRC 1992, 188: 942.
Thornberry, N A & Lazebnik, Y 1998 Science 281: 1312.
Vaughan, A T M et al. 2002 Apoptosis 7: 173
Wang, Trends Biotechnol. 11, 379, 1993.
Weston, A. et al. 2000 J'Cell Biol 148: 679.

Winkler, D G et al. 2000 J Bone Min Res 16 (Suppl. 1): S322.
Yanagi, Y et al., 1999 J Biol Chem 7: 12971.
Yamaguchi, A et al. 2000 Endocrine Rev 21: 393

All patent and literature references cited in the present specification are hereby incorporated by reference in their entirety.

What is claimed is:

1. A pharmaceutical composition comprising a carrier and a siRNA comprising SEQ ID NO: 11, wherein the siRNA can decrease SOST expression.

2. A pharmaceutical composition comprising a carrier and a siRNA comprising a strand that is selectively hybridizable under stringent conditions to the complement of SEQ ID NO: 9, wherein the siRNA can decrease SOST expression, and wherein the stringent hybridization conditions comprise hybridization in a solution of 1 mM EDTA, 0.25 M $Na_2HPO4$ and 7% SDS at 42° C., followed by washing at 42° C. in 1 mM EDTA, 40 mM $NaPO_4$, 5% SDS.

3. A method for decreasing SOST expression in a mammal that comprises administering the composition of claim 1 to the mammal in an amount effective to decrease SOST expression.

4. A method for decreasing SOST expression in a mammal that comprises administering the composition of claim 2 to the mammal in an amount effective to decrease SOST expression.

5. A method for increasing bone density in a mammal that comprises administering the composition of claim 1 to the mammal in an amount effective to increase bone density in the mammal.

6. A method for increasing bone density in a mammal that comprises administering the composition of claim 2 to the mammal in an amount effective to increase bone density in the mammal.

7. A method for decreasing apoptosis of bone cells in a mammal that comprises administering the composition of claim 1 to the mammal in an amount effective to decrease apoptosis of bone cells in the mammal.

8. A method for decreasing apoptosis of bone cells in a mammal that comprises administering the composition of claim 2 to the mammal in an amount effective to decrease apoptosis of bone cells in the mammal.

\* \* \* \* \*